US008563691B2

(12) United States Patent
LeBowitz et al.

(10) Patent No.: US 8,563,691 B2
(45) Date of Patent: *Oct. 22, 2013

(54) LYSOSOMAL TARGETING PEPTIDES AND USES THEREOF

(75) Inventors: Jonathan LeBowitz, Novato, CA (US); John Maga, Whitefish Bay, WI (US)

(73) Assignee: Biomarin Pharmaceutical, Inc., Novato, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/399,844

(22) Filed: Feb. 17, 2012

(65) Prior Publication Data

US 2012/0213762 A1 Aug. 23, 2012

Related U.S. Application Data

(63) Continuation of application No. 12/991,104, filed as application No. PCT/US2009/043207 on May 7, 2009.

(60) Provisional application No. 61/051,336, filed on May 7, 2008, provisional application No. 61/144,106, filed on Jan. 12, 2009.

(51) Int. Cl.
*C07K 1/00* (2006.01)
*A61K 38/00* (2006.01)

(52) U.S. Cl.
USPC .......................................... 530/350; 514/17.5

(58) Field of Classification Search
USPC .......................................................... 530/350
See application file for complete search history.

(56) References Cited

U.S. PATENT DOCUMENTS

| | | | |
|---|---|---|---|
| 4,309,776 | A | 1/1982 | Berguer |
| 4,522,811 | A | 6/1985 | Eppstein et al. |
| 4,749,570 | A | 6/1988 | Poznansky |
| 4,801,575 | A | 1/1989 | Pardridge |
| 4,902,505 | A | 2/1990 | Pardridge et al. |
| 5,236,838 | A | 8/1993 | Rasmussen et al. |
| 5,258,453 | A | 11/1993 | Kopecek et al. |
| 5,356,804 | A | 10/1994 | Desnick et al. |
| 5,399,346 | A | 3/1995 | Anderson et al. |
| 5,405,942 | A | 4/1995 | Bell et al. |
| 5,470,828 | A | 11/1995 | Ballard et al. |
| 5,476,779 | A | 12/1995 | Chen et al. |
| 5,549,892 | A | 8/1996 | Friedman et al. |
| 5,561,119 | A | 10/1996 | Jacquesy et al. |
| 5,580,757 | A | 12/1996 | Desnick et al. |
| 5,633,234 | A | 5/1997 | August et al. |
| 5,633,235 | A | 5/1997 | Townsend et al. |
| 5,704,910 | A | 1/1998 | Humes |
| 5,736,363 | A | 4/1998 | Edwards et al. |
| 5,798,366 | A | 8/1998 | Platt et al. |
| 5,817,623 | A | 10/1998 | Ishii |
| 5,817,789 | A | 10/1998 | Heartlein et al. |
| 5,827,703 | A | 10/1998 | Debs et al. |
| 5,854,025 | A | 12/1998 | Edwards et al. |
| 5,977,307 | A | 11/1999 | Friden et al. |
| 5,981,194 | A | 11/1999 | Jefferies et al. |
| 6,020,144 | A | 2/2000 | Gueiros-Filho et al. |
| 6,027,921 | A | 2/2000 | Heartlein et al. |
| 6,066,626 | A | 5/2000 | Yew et al. |
| 6,083,725 | A | 7/2000 | Selden et al. |
| 6,118,045 | A | 9/2000 | Reuser et al. |
| 6,226,603 | B1 | 5/2001 | Freire et al. |
| 6,235,874 | B1 | 5/2001 | Wu et al. |
| 6,262,026 | B1 | 7/2001 | Heartlein et al. |
| 6,270,989 | B1 | 8/2001 | Treco et al. |
| 6,273,598 | B1 | 8/2001 | Keck et al. |
| 6,281,010 | B1 | 8/2001 | Gao et al. |
| 6,284,875 | B1 | 9/2001 | Turpen et al. |
| 6,310,040 | B1 | 10/2001 | Bozyczko-Coyne et al. |
| 6,329,501 | B1 | 12/2001 | Smith et al. |
| 6,344,436 | B1 | 2/2002 | Smith et al. |
| 6,348,194 | B1 | 2/2002 | Huse et al. |
| 6,441,147 | B1 | 8/2002 | Turpen et al. |
| 6,451,600 | B1 | 9/2002 | Rasmussen et al. |
| 6,455,494 | B1 | 9/2002 | Jefferies et al. |
| 6,472,140 | B1 | 10/2002 | Tanzi et al. |
| 6,534,300 | B1 | 3/2003 | Canfield |
| 6,537,785 | B1 | 3/2003 | Canfield |
| 6,566,099 | B1 | 5/2003 | Selden et al. |
| 6,569,661 | B1 | 5/2003 | Qin et al. |
| 6,596,500 | B1 | 7/2003 | Kang et al. |
| 6,610,299 | B1 | 8/2003 | Kolar et al. |

(Continued)

FOREIGN PATENT DOCUMENTS

| | | | |
|---|---|---|---|
| EP | 0196056 | A2 | 10/1986 |
| EP | 0466222 | A1 | 1/1992 |

(Continued)

OTHER PUBLICATIONS

Otte et al., Gen. Comp. endcorinol., 96, 270-275, 1994.*
"Purification", The QIAexpressionist, pp. 63-107 (2001).
"QIAexpress Protein Purification System" QIAexpress—The Complete System for 6xHis Technology, pp. 7-12 (available before Feb. 19, 2009).
Achord et al., Human β-glucoronidase. II. Fate of infused human placental β-glucuronidase in the rat, Pediat. Res., 11:816-22 (1977).
Achord et al., Human β-glucuronidase: In vivo clearance and in vitro uptake by a glycoprotein recognition system on reticuloendothelial cells, Cell, 15:269-78 (1978).

(Continued)

*Primary Examiner* — Maryam Monshipouri
(74) *Attorney, Agent, or Firm* — Marshall, Gerstein & Borun LLP

(57) ABSTRACT

The present invention provides further improved compositions and methods for efficient lysosomal targeting based on the GILT technology. Among other things, the present invention provides methods and compositions for targeting lysosomal enzymes to lysosomes using furin-resistant lysosomal targeting peptides. The present invention also provides methods and compositions for targeting lysosomal enzymes to lysosomes using a lysosomal targeting peptide that has reduced or diminished binding affinity for the insulin receptor.

21 Claims, 11 Drawing Sheets

(56) References Cited

U.S. PATENT DOCUMENTS

| | | | | |
|---|---|---|---|---|
| 6,642,038 | B1 | 11/2003 | Canfield | |
| 6,670,165 | B2 | 12/2003 | Canfield | |
| 6,770,468 | B1 | 8/2004 | Canfield | |
| 6,800,472 | B2 | 10/2004 | Canfield et al. | |
| 6,828,135 | B2 | 12/2004 | Canfield | |
| 6,861,242 | B2 | 3/2005 | Canfield | |
| 6,905,856 | B2 | 6/2005 | Canfield et al. | |
| 7,067,127 | B2 | 6/2006 | Canfield | |
| 7,135,322 | B2 | 11/2006 | Canfield et al. | |
| 7,351,410 | B2 | 4/2008 | van Bree et al. | |
| 7,354,576 | B2 | 4/2008 | Kakkis | |
| 7,371,366 | B2 | 5/2008 | Canfield | |
| 7,396,811 | B2 | 7/2008 | LeBowitz et al. | |
| 7,442,372 | B2 | 10/2008 | Kakkis | |
| 7,485,314 | B2 | 2/2009 | Kakkis et al. | |
| 7,514,398 | B2 | 4/2009 | Upton et al. | |
| 7,560,424 | B2 | 7/2009 | LeBowitz et al. | |
| 7,629,309 | B2 | 12/2009 | LeBowitz et al. | |
| 7,658,916 | B2 | 2/2010 | Zhu et al. | |
| 2001/0006635 | A1 | 7/2001 | Bennett et al. | |
| 2001/0025026 | A1 | 9/2001 | Heartlein et al. | |
| 2002/0013953 | A1 | 1/2002 | Reuser et al. | |
| 2002/0081654 | A1 | 6/2002 | Sandrin et al. | |
| 2002/0110551 | A1 | 8/2002 | Chen | |
| 2002/0142299 | A1 | 10/2002 | Davidson et al. | |
| 2003/0004236 | A1 | 1/2003 | Meade | |
| 2003/0021787 | A1 | 1/2003 | Hung et al. | |
| 2003/0072761 | A1 | 4/2003 | LeBowitz | |
| 2003/0077806 | A1 | 4/2003 | Selden et al. | |
| 2003/0082176 | A1 | 5/2003 | LeBowitz et al. | |
| 2004/0005309 | A1 | 1/2004 | LeBowitz et al. | |
| 2004/0006008 | A1 | 1/2004 | LeBowitz et al. | |
| 2004/0029779 | A1 | 2/2004 | Zhu et al. | |
| 2004/0081645 | A1 | 4/2004 | Van Bree et al. | |
| 2004/0248262 | A1 | 12/2004 | Koeberl et al. | |
| 2005/0003486 | A1 | 1/2005 | Canfield et al. | |
| 2005/0026823 | A1 | 2/2005 | Zankel et al. | |
| 2005/0058634 | A1 | 3/2005 | Zhu | |
| 2005/0142141 | A1 | 6/2005 | Pardridge | |
| 2005/0170449 | A1 | 8/2005 | Canfield et al. | |
| 2005/0244400 | A1 | 11/2005 | LeBowitz et al. | |
| 2005/0281805 | A1 | 12/2005 | LeBowitz et al. | |
| 2006/0051317 | A1 | 3/2006 | Batrakova et al. | |
| 2006/0078542 | A1 | 4/2006 | Mah et al. | |
| 2006/0166328 | A1 | 7/2006 | Glass et al. | |
| 2006/0286087 | A1 | 12/2006 | Kakkis et al. | |
| 2006/0287224 | A1 | 12/2006 | DeFrees et al. | |
| 2008/0003626 | A1 | 1/2008 | White et al. | |
| 2008/0176285 | A1 | 7/2008 | Canfield | |
| 2009/0029467 | A1 * | 1/2009 | LeBowitz et al. | 435/375 |
| 2009/0041741 | A1 | 2/2009 | Sly et al. | |
| 2010/0143297 | A1 | 6/2010 | Zhu et al. | |

FOREIGN PATENT DOCUMENTS

| | | | |
|---|---|---|---|
| EP | 0599303 | A2 | 6/1994 |
| EP | 1436316 | A2 | 7/2004 |
| WO | WO-91/04014 | A1 | 4/1991 |
| WO | WO-91/14438 | A1 | 10/1991 |
| WO | WO-92/22332 | A2 | 12/1992 |
| WO | WO-93/06216 | A1 | 4/1993 |
| WO | WO-93/10819 | A1 | 6/1993 |
| WO | WO-94/02178 | A1 | 2/1994 |
| WO | WO-95/02421 | A1 | 1/1995 |
| WO | WO-00/53730 | A2 | 9/2000 |
| WO | WO-01/19955 | A2 | 3/2001 |
| WO | WO-01/53730 | A1 | 7/2001 |
| WO | WO-02/044355 | A2 | 6/2002 |
| WO | WO-02/056907 | A2 | 7/2002 |
| WO | WO-02/087510 | A2 | 11/2002 |
| WO | WO-03/032727 | A1 | 4/2003 |
| WO | WO-03/032913 | A2 | 4/2003 |
| WO | WO-03/057179 | A2 | 7/2003 |
| WO | WO-03102583 | A1 | 12/2003 |
| WO | WO-2005/077093 | | 8/2005 |
| WO | WO-2005/078077 | A2 | 8/2005 |

OTHER PUBLICATIONS

Aeed et al., Glycosylation of recombinant prorenin in insect cells: the insect cell line Sf9 does not express the mannose 6-phosphate recognition signal, Biochemistry, 33:8793-7 (1994).

Aerts et al., Efficient routing of glucocerebrosidase to lysosomes requires complex oligosaccharide chain formation, Biochem. Biophys. Res. Commun., 141:452-8 (1986).

Allen et al., Metabolic correction of fucosidosis lymphoid cells by galaptin-alpha-L-fucosidase conjugates, Biochem. Biophys. Res. Commun., 172:335-40 (1990).

Amalfitano et al., Recombinant human acid alpha-glucosidase enzyme therapy for infantile glycogen storage disease type II: results of a phase I/II clinical trial, Genet. Med., 3(2):132-8 (2001).

Anand, The Cure, Chapter 23, pp. 257-68, New York, NY: Harper Collins (2006).

Arai et al., Conformations of variably linked chimeric proteins evaluated by synchrotron X-ray small-angle scattering, Proteins, 57(4):829-38 (2004).

Armstrong et al., Uptake of circulating insulin-like growth factor-I into the cerebrospinal fluid of normal and diabetic rats and normalization of IGF-II mRNA content in diabetic rat brain, J. Neurosci. Res., 59(5):649-60 (2000).

Auletta et al., Receptor-mediated endocytosis and degradation of insulin-like growth factor I and II in neonatal rat astrocytes, J. Neurosci. Res., 31(1):14-20 (1992).

Authier et al., In vitro endosome-lysosome transfer of dephosphorylated EGF receptor and Shc in rat liver, FEBS Lett., 461(1-2):25-31 (1999).

Bach et al., Binding of mutants of human insulin-like growth factor II to insulin-like growth factor binding proteins 1-6, J. Biol. Chem., 268(13):9246-54 (1993).

Bartlett et al., CAVEAT: A program to facilitate the structure-derived design of biologically active molecules, Molecular Recognition: Chemical and Biological Problems, pp. 182-196 (1989).

Barton et al., Therapeutic response to intravenous infusions of glucocerebrosidase in a patient with Gaucher disease, Proc. Natl. Acad. Sci. USA, 87(5):1913-6 (1990).

Baxter, Insulin-like growth factor (IGF)-binding proteins: interactions with IGFs and intrinsic bioactivities, Am. J. Physiol. Endocrinol. Metab., 278(6):E967-76 (2000).

Becker et al., HLA and mate choice, J. Hum. Genet., 62:991 (1998).

Beljaars et al., Characteristics of the hepatic stellate cell-selective carrier mannose 6-phosphate modified albumin (M6P(28)-HSA), Liver, 21:320-8 (2001).

Beutler et al., Gaucher Disease, IN: Scriver et al., The Metabolic and Molecular Bases of Inherited Diseases, 8th ed., McGraw-Hill Professional, pp. 3635-3668 (2000).

Bickel et al., Delivery of peptides and proteins through the blood-brain barrier, Adv. Drug Deliv. Rev., 46(1-3):247-79 (2001).

Bijsterbosch et al., Native and modified lipoproteins as drug delivery systems, Adv. Drug Deliv. Rev., 5:231-51 (1990).

Bijvoet et al., Expression of cDNA-encoded human acid alpha-glucosidase in milk of transgenic mice, Biochim. Biophys. Acta, 1308(2):93-6 (1996).

Bijvoet et al., Human acid alpha-glucosidase from rabbit milk has therapeutic effect in mice with glycogen storage disease type II, Hum. Mol. Genet., 8(12):2145-53 (1999).

Bijvoet et al., Recombinant human acid alpha-glucosidase: high level production in mouse milk, biochemical characteristics, correction of enzyme deficiency in GSDII KO mice, Hum. Mol. Genet., 7(11):1815-24 (1998).

Birkenmeier et al., Increased life span and correction of metabolic defects in murine mucopolysaccharidosis type VII after syngeneic bone marrow transplantation, Blood, 78(11):3081-92 (1991).

Birkenmeier et al., Murine mucopolysaccharidosis type VII. Characterization of a mouse with beta-glucuronidase deficiency, J. Clin. Invest., 83(4):1258-66 (1989).

(56) References Cited

OTHER PUBLICATIONS

Bishop et al., Human a-galactosidase characterization and eukaryotic expression of the full-length cDNA and structural organization of the gene, IN: Lipid Storage Disorders Biological and Medical Aspects, vol. 150, pp. 809-822 (1987).
Blakey et al., Effect of chemical deglycosylation of ricin A chain on the in vivo fate and cytotoxic activity of an immunotoxin composed of ricin A chain and anti-Thy 1.1 antibody, Cancer Res., 47:947-52 (1987).
Borch et al., The cyanohydridoborate anion as a selective reducing agent. J. Am. Chem. Soc., 93:2897 (1971).
Brady et al., Enzyme replacement therapy in Fabry disease, J. Inherit. Metab. Dis., 24 Suppl 2:18-24 (2001).
Braulke et al., Insulin-like growth factors I and II stimulate endocytosis but do not affect sorting of lysosomal enzymes in human fibroblasts, J. Biol. Chem., 265(12):6650-5 (1990).
Braulke, Type-2 IGF receptor: a multi-ligand binding protein, Horm. Metab. Res., 31:242-6 (1999).
Brooks et al., Functional correction of established central nervous system deficits in an animal model of lysosomal storage disease with feline immunodeficiency virus-based vectors, Proc. Natl. Acad. Sci. USA, 99(9):6216-21 (2002).
Brooks, Immune response to enzyme replacement therapy in lysosomal storage disorder patients and animal models, Mol. Genet. Metab., 68:268-75 (1999).
Brown et al., Structure of a functional IGF2R fragment determined from the anomalous scattering of sulfur, EMBO J., 21:1054-62 (2002).
Bungard, Design of Prodrugs, pp. 7-9 and 21-24, Elsevier (1985).
Burgisser et al., Mutants of human insulin-like growth factor II with altered affinities for the type 1 and type 2 insulin-like growth factor receptor, J. Biol. Chem., 266:1029-33 (1991).
Cacciari et al., Somatomedin C in pediatric pathophysiology, Pediatrician, 14(3):146-53 (1987).
Calhoun et al., Fabry disease: isolation of a cDNA clone encoding human alpha-galactosidase A, Proc. Natl. Acad. Sci. USA, 82:7364-8 (1985).
Carter et al., Improved oligonucleotide site-directed mutagenesis using M13 vectors. *Nucleic Acids Res.,* 13:4331 (1986).
Cascieri et al., Structural analogs of human insulin-like growth factor (IGF) I with altered affinity for type 2 IGF receptors, J. Biol. Chem., 264(4):2199-202 (1989).
Chodobski et al., Choroid plexus: target for polypeptides and site of their synthesis, Microsc. Res. Tech., 52:65-82 (2001).
Chothia, The nature of the accessible and buried surfaces in proteins, J. Mol. Biol., 105:1-12 (1976).
Dahms et al., Mannose 6-phosphate receptors and lysosomal enzyme targeting, J. Biol. Chem., 264(21):12115-8 (1989).
Daly et al., Neonatal gene transfer leads to widespread correction of pathology in a murine model of lysosomal storage disease, Proc. Natl. Acad. Sci. USA, 96(5):2296-300 (1999).
Desnick et al., Enzyme replacement and enhancement therapies: lessons from lysosomal disorders, Nat. Rev. Genet., 3(12):954-66 (2002).
Devedijan et al., Transgenic mice overexpressing insulin-like growth factor-II in beta cells develop type 2 diabetes, J. Clin. Invest., 105(6):731-40 (2000).
Devi et al., An insulin-like growth factor II (IGF-II) affinity-enhancing domain localized within extracytoplasmic repeat 13 of the IGF-II/mannose 6-phosphate receptor, Mol. Endocrinol., 12:1661-72 (1998).
Difalco et al., Efficacy of an insulin-like growth factor-interleukin-3 fusion protein in reversing the hematopoietic toxicity associated with azidothymidine in mice, J. Pharmacol. Exp. Ther., 284:449-54 (1998).
Difalco et al., Preparation of a recombinant chimaera of insulin-like growth factor II and interleukin 3 with high proliferative potency for haemopoietic cells, Biochem. J., 326(Pt. 2):407-13 (1997).
Diment et al., Generation of macrophage variants with 5-azacytidine: selection for mannose receptor expression, J. Leukoc. Biol., 42:485-90 (1987).
Dixon, Computer-aided drug design: getting the best results, Trends Biotechnol., 10(10):357-63 (1992).
Dobrenis et al., Neuronal lysosomal enzyme replacement using fragment C of tetanus toxin, Proc. Natl. Acad. Sci. USA, 89(6):2297-301 (1992).
Douglass et al., Chemical deglycosylation can induce methylation, succinimide formation, and isomerization, J. Protein Chem., 20(7);571-6 (2001).
Duffy et al., Human blood-brain barrier insulin-like growth factor receptor, Metabolism, 37(2):136-40 (1988).
Duguay et al., Post-translational processing of the insulin-like growth factor-2 precursor. Analysis of O-glycosylation and endoproteolysis, J. Biol. Chem., 273:18443-51 (1998).
Dziegielewska et al., The ins and outs of brain-barrier mechanisms, Trends Neurosci., 25(2):69-71 (2002).
Eisen et al., HOOK: a program for finding novel molecular architectures that satisfy the chemical and steric requirements of a macromolecule binding site, Proteins, 19(3):199-221 (1994).
European search report for EP08000935 (2008).
European supplementary partial search report for European application No. EP03736779 (mailing date Apr. 5, 2007).
Europen search report for EP02801739 (2005).
Extended European Search Report for corresponding European application No. EP09743707.3, dated Aug. 17, 2011.
Forbes et al., Contribution of residues A54 and L55 of the human insulin-like growth factor-II (IGF-II) A domain to Type 2 IGF receptor binding specificity, Growth Factors, 19(3):163-73 (2001).
Foxwell et al., The preparation of deglycosylated ricin by recombination of glycosidase-treated A- and B-chains: effects of deglycosylation on toxicity and in vivo distribution, Biochim. Biophys. Acta, 923(1);59-65 (1987).
Francis et al., Insulin-like growth factor (IGF)-II binding to IGF-binding proteins and IGF receptors is modified by deletion of the N-terminal hexapeptide or substitution of arginine for glutamate-6 in IGF-II, Biochem. J., 293(Pt. 3):713-9 (1993).
Frank et al., Binding and internalization of insulin and insulin-like growth factors by isolated brain microvessels, Diabetes, 35(6):654-61 (1986).
Friden et al, Anti-transferrin receptor antibody and antibody-drug conjugates cross the blood-brain barrier, Proc. Natl. Acad. Sci. USA, 88(11):4771-5 (1991).
Fukuda et al., Autophagy and lysosomes in Pompe disease, Autophagy, 2(4):318-20 (2006).
Fukuda et al., Autophagy and mistargeting of therapeutic enzyme in skeletal muscle in Pompe disease, Mol. Ther., 14(6):831-9 (2006).
Fukuda et al., Dysfunction of endocytic and autophagic pathways in a lysosomal storage disease, Ann. Neurol., 59(4):700-8 (2006).
Fukuta et al., Insulin fragments as a carrier for peptide delivery across the blood-brain barrier, Pharm. Res., 11:1681-8 (1994).
Godar et al., M6P/IGFII-receptor complexes urokinase receptor and plasminogen for activation of transforming growth factor-beta1, Eur. J. Immunol., 29(3):1004-13 (1999).
Golden et al., Human blood-brain barrier leptin receptor. Binding and endocytosis in isolated human brain microvessels, J. Clin. Invest., 99(1):14-8 (1997).
Gordon et al., A role for PACE4 in the proteolytic activation of anthrax toxin protective antigen, Infect. Immun., 65(8):3370-5 (1997).
Gozes et al., Neuropeptides: brain messengers of many faces, Trends Neurosci., 24(12):687-90 (2001).
Graham et al., Characteristics of a human cell line transformed by DNA from human adenovirus type 5, J. Gen. Virol., 36(1): 59-74 (1977).
Grimme et al., Endocytosis of insulin-like growth factor II by a mini-receptor based on repeat 11 of the mannose 6-phosphate/insulin-like growth factor II receptor, J. Biol. Chem., 275(43):33697-703 (2000).
Grubb et al., Chemically modified beta-glucuronidase crosses blood-brain barrier and clears neuronal storage in murine mucopolysaccharidosis VII, Proc. Natl. Acad. Sci. USA, 105(7):2616-21 (2008).

(56) References Cited

OTHER PUBLICATIONS

Grubb et al., Large scale purification of phosphorylated recombinant β-glucuronidase from over-expressing mouse L cells, FASEB J., 7:1255a (1993).
Hashimoto et al., Binding sites and binding properties of binary and ternary complexes of insulin-like growth factor-II (IGF-II), IGF-binding protein-3, and acid-labile subunit, J. Biol. Chem., 272:27936-42 (1997).
Hashimoto et al., N-terminal deletion mutants of insulin-like growth factor-II (IGF-II) show Thr7 and Leu8 important for binding to insulin and IGF-I receptors and Leu8 critical for all IGF-II functions, J. Biol. Chem., 270(30):18013-8 (1995).
Haskell et al., Intracellular trafficking of the JNCL protein CLN3, Mol. Genet. Metab., 66:253-60 (1999).
Henikoff et al., Amino acid substitution matrices from protein blocks, Proc. Natl. Acad. Sci. USA, 89:10915-9 (1992).
Hickman et al., A recognition marker required for uptake of a lysosomal enzyme by cultured fibroblasts, Biochem. Biophys. Res. Commun., 57:55-61 (1974).
Hirschhorn et al., Glycogen storage disease type II: Acid alpha-glucosidase (acid maltase) deficiency, IN: Schriver et al. (eds.), *The Metabolic and Molecular Basis of Inherited Disease,* 8th Ed., New York: McGraw-Hill, pp. 3389-3420 (2001).
Hoefsloot et al., Expression and routeing of human lysosomal alpha-glucosidase in transiently transfected mammalian cells, Biochem. J., 272:485-92 (1990).
Houba et al., Improved characteristics of a human beta-glucuronidase-antibody conjugate after deglycosylation for use in antibody-directed enzyme prodrug therapy, Bioconjug. Chem., 7:606-11 (1996).
International Preliminary Report on Patentability for corresponding International application No. PCT/US2009/043207, dated Nov. 9, 2010.
International Search Report for corresponding International application No. PCT/US2009/043207, mailing date Feb. 16, 2010.
International Search Report for PCT/US02/13835 (2002).
International Search Report for PCT/US02/32968 (2002).
International Search Report for PCT/US02/32996 (2002).
International Search Report for PCT/US03/17211 (2003).
International Search Report for PCT/US07/23881 (2009).
Ishibashi et al., Asialoglycoprotein receptor deficiency in mice lacking the minor receptor subunit, J. Biol. Chem., 269:27803-6 (1994).
Islam et al., C-terminal processing of human beta-glucuronidase. The propeptide is required for full expression of catalytic activity, intracellular retention, and proper phosphorylation, J. Biol. Chem., 268(30):22627-33 (1993).
Jacob et al., Sucrase is an intramolecular chaperone located at the C-terminal end of the sucrase-isomaltase enzyme complex, J. Biol. Chem., 277(35):32141-8 (2002).
Journet et al., Proteomic analysis of human lysosomes: application to monocytic and breast cancer cells, Proteomics, 2(8):1026-40 (2002).
Juuti-Uusitalo et al., Selective targeting of avidin/mannose 6-phosphate receptor chimeras to early or late endosomes, Eur. J. Cell Biol., 79(7):458-68 (2000).
Kang et al., Mannose 6-phosphate/insulin-like growth factor II receptor mediates the growth-inhibitory effects of retinoids, Cell Growth Differ., 10(8):591-600 (1999).
Kang et al., Mannose-6-phosphate/insulin-like growth factor-II receptor is a receptor for retinoic acid, Proc. Natl. Acad. Sci. USA, 94(25):13671-6 (1997).
Kang et al., Retinoic acid alters the intracellular trafficking of the mannose-6-phosphate/insulin-like growth factor II receptor and lysosomal enzymes, Proc. Natl. Acad. Sci. USA, 95:13687-91 (1998).
Kerr et al., Comparison of recombinant and synthetically formed monoclonal antibody-beta-lactamase conjugates for anticancer prodrug activation, Bioconjug. Chem., 10(6)1 084-9 (1999).
Kiess et al., Biochemical evidence that the type II insulin-like growth factor receptor is identical to the cation-independent mannose 6-phosphate recetor, J. Biol. Chem., 263:9339-44 (1988).
Kiess et al., Insulin-like growth factor II (IGF-II) and the IGF-II/mannose-6-phosphate receptor: the myth continues, Horm. Res., 41 Suppl 2:66-73 (1994).
Kiess et al., Insulin-like growth factor-II (IGF-II) inhibits both the cellular uptake of beta-galactosidase and the binding of beta-galactosidase to purified IGF-II/mannose 6-phosphate receptor, J. Biol. Chem., 264(8):4710-4 (1989).
Kikuchi et al., Clinical and metabolic correction of pompe disease by enzyme therapy in acid maltase-deficient quail, J. Clin. Invest, 101(4):827-33 (1998).
Kim et al., High-level expression and simple purification of recombinant human insulin-like growth factor I, J. Biotechnol., 48(1-2):97-105 (1996).
Kishnani et al., A retrospective, multinational, multicenter study on the natural history of infantile-onset Pompe disease, J. Pediatr., 148:671-6 (2006).
Kishnani et al., Chinese hamster ovary cell-derived recombinant human acid alpha-glucosidase in infantile-onset Pompe disease, J. Pediatr., 149:89-97 (2006).
Kishnani et al., Recombinant human acid [alpha]-glucosidase: major clinical benefits in infantile-onset Pompe disease, Neurology, 68:99-109 (2007).
Korner et al., Mannose 6-phosphate/insulin-like growth factor II receptor fails to interact with G-proteins. Analysis of mutant cytoplasmic receptor domains, J. Biol. Chem., 270:287-95 (1995).
Kundra et al., Asparagine-linked oligosaccharides protect Lamp-1 and Lamp-2 from intracellular proteolysis, J. Biol. Chem., 274:31039-46 (1999).
Langford et al., Leishmania: codon utilization of nuclear genes, Exp. Parasitol., 74:360-1 (1992).
Lau et al., Loss of the imprinted IGF2/cation-independent mannose 6-phosphate receptor results in fetal overgrowth and perinatal lethality, Genes Dev., 8:2953-64 (1994).
Lebowitz et al., A breach in the blood-brain barrier, Proc. Natl. Acad. Sci. USA, 102:14485-6 (2005).
Lebowitz et al., Glycosylation-independent targeting enhances enzyme delivery to lysosomes and decreases storage in mucopolysaccharidosis type VII mice, PNAS, 101 (9):3083-8 (2004).
Lee et al., Mannose receptor-mediated regulation of serum glycoprotein homeostasis, Science, 295:1898-901 (2002).
Lemansky et al., Synthesis and processing of alpha-galactosidase A in human fibroblasts. Evidence for different mutations in Fabry disease, J. Biol. Chem., 262:2062-5 (1987).
Linnell et al., Real time kinetics of insulin-like growth factor II (IGF-II) interaction with the IGF-II/mannose 6-phosphate receptor: the effects of domain 13 and pH, J. Biol. Chem., 276:23986-91 (2001).
Liu et al., Intranasal administration of insulin-like growth factor-I bypasses the blood-brain barrier and protects against focal cerebral ischemic damage, J. Neurol. Sci., 187:91-7 (2001).
Ludwig et al., Mouse mutants lacking the type 2 IGF receptor (IGF2R) are rescued from perinatal lethality in Igf2 and Igf1r null backgrounds, Dev. Biol., 177:517-35 (1996).
Ludwig et al., Roles for mannose-6-phosphate receptors in lysosomal enzyme sorting, IGF-II binding and clathrin-coat assembly, Trends Cell Biol., 5:202-6 (1995).
Luthi et al., Mutants of human insulin-like growth factor II (IGF II). Expression and characterization of truncated IGF II and of two naturally occurring variants, Eur. J. Biochem., 205(2):483-90 (1992).
Lynch et al., High-resolution light microscopy (HRLM) and digital analysis of Pompe disease pathology, J. Histochem. Cytochem., 53:63-73 (2005).
Magee et al., Insulin-like growth factor I and its binding proteins: a study of the binding interface using B-domain analogues, Biochemistry, 38(48):15863-70 (1999).
Mah et al., Physiological correction of pompe disease by systemic delivery of adeno-associated virus serotype I vectors, Molecular Therapy, 15:501-7 (2007).
Mahuran et al., Proteolytic processing of pro-alpha and pro-beta precursors from human beta-hexosaminidase. Generation of the mature alpha and beta a beta b subunits, J. Biol. Chem., 263:4612-8 (1988).

(56) References Cited

OTHER PUBLICATIONS

Martin, Computer-assisted rational drug design, Methods Enzymol., 203:487-613 (1991).
Martiniuk et al., Correction of glycogen storage disease type II by enzyme replacement with a recombinant human acid maltase produced by over-expression in a CHO-DHFR(neg) cell line, Biochem. Biophys. Res. Commun., 276:917-23 (2000).
Martiniuk et al., Recombinant human acid alpha-glucosidase generated in bacteria: antigenic, but enzymatically inactive, DNA Cell Biol., 11:701-6 (1992).
Mather et al., Culture of testicular cells in hormone-supplemented serum-free medium, Ann. NY Acad. Sci., 383:44-68 (1982).
Mather, Establishment and characterization of two distinct mouse testicular epithelial cell lines, Biol. Reprod., 23(1):243-52 (1980).
Mazzolla et al., Enhanced resistance to Cryptococcus neoformans infection induced by chloroquine in a murine model of meningoencephalitis, Antimicrob. Agents Chemother., 41:802-7 (1997).
Meynial-Salles et al., In vitro glycosylation of proteins: an enzymatic approach, J. Biotechnol., 46:1-14 (1996).
Moehring et al., Strains of CHO-K1 cells resistant to Pseudomonas exotoxin A and cross-resistant to diphtheria toxin and viruses, Infect. Immun., 41(3):998-1009 (1983).
Molloy et al., Human furin is calcium-dependent serine endoprotease that recognizes the sequence ARG-X-X-ARG and efficiently cleaves anthrax toxin protective antigen, J. Biol. Chem., 267:16396-402 (1992).
Moreland et al., Lysosomal acid alpha-glucosidase consists of four different peptides processed from a single chain precursor, J. Biol. Chem., 280:6780-91 (2005).
Morgan et al., Insulin-like growth factor II receptor as a multifunctional binding protein, Nature, 329:301-7 (1987).
Myszka et al., Kinetic, equilibrium, and thermodynamic analysis of macromolecular interactions with BIACORE, Methods Enzymol., 323:325-40 (2000).
Newrzella et al., Functional analysis of the glycosylation of murine acid sphingomyelinase, J. Biol. Chem., 271:32089-95 (1996).
Nilsson et al., Induction of immune tolerance in patients with hemophilia and antibodies to factor VIII by combined treatment with intravenous IgG, cyclophosphamide, and factor VIII, N. Engl. J. Med., 318:947-50 (1988).
Nissley et al., Reciprocal modulation of binding of lysosomal enzymes and insulin-like growth factor-II (IGF-II) to the mannose 6-phosphate/IGF-II receptor, Adv. Exp. Med. Biol., 293:311-24 (1991).
Niwa et al., Efficient selection for high-expression transfectants with a novel eukaryotic vector, Gene, 108:193-9 (1991).
Nolan et al., Binding of insulin-like growth factor II (IGF-II) by human cation-independent mannose 6-phosphate receptor/IGF-II receptor expressed in receptor-deficient mouse L cells, Cell Regul., 1(2):197-213 (1990).
Novazyme Website printouts (2001).
Nykjaer et al., Mannose 6-phosphate/insulin-like growth factor-II receptor targets the urokinase receptor to lysosomes via a novel binding interaction, J. Cell Biol., 141:815-28 (1998).
O'Connor et al., Enzyme replacement therapy for murine mucopolysaccharidosis type VII leads to improvements in behavior and auditory function, J. Clin. Invest., 101:1394-400 (1998).
O'Dell et al., Insulin-like growth factor II (IGF-II), Int. J. Biochem. Cell Biol., 30:767-71 (1998).
Oksche et al., Late endosomal/lysosomal targeting and lack of recycling of the ligand-occupied endothelin B receptor, Mol. Pharmacol., 57(6):1104-13 (2000).
Paasche et al., Mechanisms of endothelin receptor subtype-specific targeting to distinct intracellular trafficking pathways, J. Biol. Chem., 276:34041-50 (2001).
Pardridge et al., Drug delivery to the brain, J. Cereb. Blood Flow Metab., 17:713-31 (1997).
Pardridge, Targeting neurotherapeutic agents through the blood-brain barrier, Arch. Neurol., 59:35-40 (2002).
Pauly et al., Complete correction of acid alpha-glucosidase deficiency in Pompe disease fibroblasts in vitro, and lysosomally targeted expression in neonatal rat cardiac and skeletal muscle, Gene Ther., 5(4):473-80 (1998).
PCT International Preliminary report on Patentability for International Application No. PCT/US05/004286) (Date of issuance Aug. 14, 2006).
PCT International Search Report for International Application No. PCT/US05/004286 (Date of mailing Aug. 31, 2005).
Pine, Organic Chemistry, 5th ed., McGraw Hill, p. 770 (1987).
Polychronakos et al., Effects of mannose-6-phosphate on receptor-mediated endocytosis of insulin-like growth factor-II, Endocrinology, 127(4):1861-6 (1990).
Poznansky et al., Enzyme replacement therapy in fibroblasts from a patient with cholesteryl ester storage disease, FASEB J., 3:152-6 (1989).
Prince et al., Lipoprotein receptor binding, cellular uptake, and lysosomal delivery of fusions between the receptor-associated protein (RAP) and alpha-L-iduronidase or acid alpha-glucosidase, J. Biol. Chem., 279(33):35037-46 (2004).
Pulford et al., Uptake of circulating insulin-like growth factors (IGFs) into cerebrospinal fluid appears to be independent of the IGF receptors as well as IGF-binding proteins, Endocrinology, 142(1):213-20 (2001).
Raben et al., Acid alpha-glucosidase deficiency (glycogenosis type II, Pompe disease), Curr. Mol. Med., 2(2):145-66 (2002).
Raben et al., Targeted disruption of the acid alpha-glucosidase gene in mice causes an illness with critical features of both infantile and adult human glycogen storage disease type II, J. Biol. Chem., 273(30):19086-92 (1998).
Ramalingam et al., Binding to the transferrin receptor is required for endocytosis of HFE and regulation of iron homeostasis, Nat. Cell Biol., 2(12):953-7 (2000).
Reinhardt et al., Insulin-like growth factors cross the blood-brain barrier, Endocrinology, 135(5):1753-61 (1994).
Reuser et al., Biochemical, immunological, and cell genetic studies in glycogenosis type II, Am. J. Hum. Genet., 30(2):132-43 (1978).
Rhee et al., High-level expression of human insulin-like growth factor II in *Escherichia coli,* J. Biotechnol., 13(4):293-304 (1990).
Robyt, Essentials of Carbohydrate Chemistry, pp. 34-35 and p. 350, Springer (1998).
Rocca et al., Involvement of the ubiquitin/proteasome system in sorting of the interleukin 2 receptor beta chain to late endocytic compartments, Mol. Biol. Cell, 12(5):1293-301 (2001).
Rosenberg et al., Immunosurveillance of alglucerase enzyme therapy for Gaucher patients: induction of humoral tolerance in seroconverted patients after repeat administration, Blood, 93(6):2081-8 (1999).
Roth et al., Mutants of human insulin-like growth factor II: expression and characterization of analogs with a substitution of TYR27 and/or a deletion of residues 62-67, Biochem. Biophys. Res. Commun., 181(2):907-14 (1991).
Russell et al., Recombinant proteins for genetic disease, Clin. Genet., 55:389-94 (1999).
Sakano et al., The design, expression, and characterization of human insulin-like growth factor II (IGF-II) mutants specific for either the IGF-II/cation-independent mannose 6-phosphate receptor or IGF-I receptor, J. Biol. Chem., 266(31):20626-35 (1991).
Samoylova et al., Elucidation of muscle-binding peptides by phage display screening, Muscle Nerve, 22(4):460-6 (1999).
Sandoval et al., Enhanced proliferative effects of a baculovirus-produced fusion protein of insulin-like growth factor and alpha(1)-proteinase inhibitor and improved anti-elastase activity of the inhibitor with glutamate at position 351, Protein Eng., 15(5):413-8 (2002).
Sandoval et al., The fusion of IGF I with stromal cell-derived factor I or alpha1 proteinase inhibitor alters their mitogenic or chemotactic activities while keeping their ability to inhibit HIV-1-gp120 binding, Biochem. Pharmacol., 65(12):2055-63 (2003).
Sands et al., Biodistribution, kinetics, and efficacy of highly phosphorylated and non-phosphorylated beta-glucuronidase in the murine model of mucopolysaccharidosis VII, J. Biol. Chem., 276:43160-5 (2001).

(56) References Cited

OTHER PUBLICATIONS

Sands et al., Enzyme replacement therapy for murine mucopolysaccharidosis type VII, J. Clin. Invest., 93:2324-31 (1994).
Sands et al., Murine mucopolysaccharidosis type VII: long term therapeutic effects of enzyme replacement and enzyme replacement followed by bone marrow transplantation, J. Clin. Invest., 99:1596-605 (1997).
Shin et al., Functional properties of antibody insulin-like growth factor fusion proteins, J. Biol. Chem., 269(7):4979-85 (1994).
Shipley et al., The role of glycosylation and phosphorylation in the expression of active human beta-glucuronidase, J. Biol. Chem., 268(16):12193-8 (1993).
Silverman, The Organic Chemistry of Drug Design and Drug Action, pp. 352-401, San Diego, CA: Academic Press (1992).
Sly et al., Active site mutant transgene confers tolerance to human beta-glucuronidase without affecting the phenotype of MPS VII mice, Proc. Natl. Acad. Sci. USA, 98(5):2205-10 (2001).
Smith et al., Identification of common molecular subsequences, J. Mol. Biol., 147:195-7 (1981).
Smith et al., Structure and activity dependence of recombinant human insulin-like growth factor II on disulfide bond pairing, J. Biol. Chem., 264:9314-21 (1989).
Sohar et al., Mouse mutants lacking the cation-independent mannose 6-phosphate/insulin-like growth factor II receptor are impaired in lysosomal enzyme transport: comparison of cation-independent and cation-dependent mannose 6-phosphate receptor-deficient mice, Biochem. J., 330(Pt. 2):903-8 (1998).
Sojar et al., Characterization of rat ovarian lutropin receptor. Role of thiol groups in receptor association, J. Biol. Chem., 264:2552-9 (1989).
Sojar et al., Chemical deglycosylation of glycoproteins, Methods Enzymol., 138:341-50 (1987).
Soper et al., Enzyme replacement therapy improves reproductive performance in mucopolysaccharidosis type VII mice but does not prevent postnatal losses, Pediatr. Res., 45(2):180-6 (1999).
Souriau et al., Direct selection of EGF mutants displayed on filamentous phage using cells overexpressing EGF receptor, Biol. Chem., 380:451-8 (1999).
Sperr et al., Rituximab for the treatment of acquired antibodies to factor VIII, Haematologica, 92:66-71 (2007).
Spiro et al., Characterization of carbohydrate units of glycoproteins, Methods Enzymol., 8:44-9 (1966).
Spodsberg et al., Molecular basis of aberrant apical protein transport in an intestinal enzyme disorder, J. Biol. Chem., 276:23506-10 (2001).
Stahl et al., Evidence for specific recognition sites mediating clearance of lysosomal enzymes in vivo, Proc. Natl. Acad. Sci. USA, 73(11):4045-9 (1976).
Standley et al., The role of glycosylation in ionotropic glutamate receptor ligand binding, function, and trafficking, Cell Mol. Life Sci., 57(11):1508-16 (2000).
Stanley et al., Chinese hamster ovary cells selected for resistance to the cytotoxicity of phytohemagglutinin are deficient in a UDP-N-acetylglucosamine—glycoprotein N-acetylglucosaminyltransferase activity, Proc. Natl. Acad. Sci. USA, 72(9):3323-7 (1975).
Stanley et al., Selection and characterization of eight phenotypically distinct lines of lectin-resistant Chinese hamster ovary cell, Cell, 6(2):121-8 (1975).
Summary of the Boston IPA Board Meeting, Apr. 16-17, 2002, Association for Glycogen Storage Disease (UK) Bulletin, Issue 9, p. 14 (May 2002).
Supplementary European Search Report for EP 02725886 (2004).
Terasawa et al., Solution structure of human insulin-like growth factor II; recognition sites for receptors and binding proteins, EMBO J., 13(23):5590-7 (1994).
The Cytokine Facts Book, 2nd ed., pp. 301-305, Academic Press (2001).
Thim, A new family of growth factor-like peptides. 'Trefoil' disulphide loop structures as a common feature in breast cancer associated peptide (pS2), pancreatic spasmolytic polypeptide (PSP), and frog skin peptides (spasmolysins), FEBS Lett., 250(1):58-90 (1989).
Thorpe et al., Modification of the carbohydrate in ricin with metaperiodate-cyanoborohydride mixtures. Effects on toxicity and in vivo distribution, Eur. J. Biochem., 147(1):197-206 (1985).
Thotakura et al., Enzymatic deglycosylation of glycoproteins, Methods Enzymol., 138:350-9 (1987).
Thurberg et al., Characterization of pre- and post-treatment pathology after enzyme replacement therapy for Pompe disease, Lab Invest., 86(12):1208-20 (2006).
Timmermans et al., Characterization of pre- and post-treatment pathology after enzyme replacement therapy for Pompe disease, Pharmacol. Rev., 45(2):205-51 (1993).
Tong et al., The cation-independent mannose 6-phosphate receptor binds insulin-like growth factor II, J. Biol. Chem., 263(6):2585-8 (1988).
Torres et al., Solution structure of human insulin-like growth factor II. Relationship to receptor and binding protein interactions, J. Mol. Biol., 248(2):385-401 (1995).
Tschinke et al., The NEWLEAD program: a new method for the design of candidate structures from pharmacophoric hypotheses, J. Med. Chem., 36(24):3863-70 (1993).
Tsuji et al., Intracellular transport of acid alpha-glucosidase in human fibroblasts: evidence for involvement of phosphomannosyl receptor-independent system, J. Biochem., 104(2):276-8 (1988).
Tsuji et al., Lysosomal enzyme replacement using alpha 2-macroglobulin as a transport vehicle, J. Biochem., 115:937-44 (1994).
Tsuji et al., The precursor of acid α-glycosidase is synthesized as a membrane-bound enzyme, Biochem., Int., 15(5):945-52 (1987).
Ulmasov et al., Purification and kinetic analysis of recombinant CA XII, a membrane carbonic anhydrase overexpressed in certain cancers, Proc. Natl. Acad. Sci. USA, 97(26):14212-7 (2000).
Urayama et al., Developmentally regulated mannose 6-phosphate receptor-mediated transport of a lysosomal enzyme across the blood-brain barrier, Proc. Natl. Acad. Sci. USA, 101(34):12658-63 (2004).
Urlaub et al., Isolation of Chinese hamster cell mutants deficient in dihydrofolate reductase activity, Proc. Natl. Acad. Sci. USA, 77(7):4216-20 (1980).
Vaccaro, Karen, email dated Feb. 20, 2002.
Valenzano et al., Biophysical and biological properties of naturally occurring high molecular weight insulin-like growth factor II variants, J. Biol. Chem., 272(8):4804-13 (1997).
Valenzano et al., Soluble insulin-like growth factor II/mannose 6-phosphate receptor carries multiple high molecular weight forms of insulin-like growth factor II in fetal bovine serum, J. Biol. Chem., 270(27):16441-8 (1995).
Van den Hout et al., Enzyme therapy for pompe disease with recombinant human alpha-glucosidase from rabbit milk, J. Inherit Metab. Dis., 24:266-74 (2001).
Van den Hout et al., Recombinant human alpha-glucosidase from rabbit milk in Pompe patients, Lancet, 356(9227):397-8 (2000).
Van der Ploeg et al., Intravenous administration of phosphorylated acid alpha-glucosidase leads to uptake of enzyme in heart and skeletal muscle of mice, J. Clin. Invest., 87(2):513-8 (1991).
Van Doorn et al., Antibodies directed against the E region of pro-insulin-like growth factor-II used to evaluate non-islet cell tumor-induced hypoglycemia, Clin. Chem., 48(10):1739-50 (2002).
Van Hove et al., High-level production of recombinant human lysosomal acid alpha-glucosidase in Chinese hamster ovary cells which targets to heart muscle and corrects glycogen accumulation in fibroblasts from patients with Pompe disease, Proc. Natl. Acad. Sci. USA, 93(1):65-70 (1996).
Vogler et al., A murine model of mucopolysaccharidosis VII. Gross and microscopic findings in beta-glucuronidase-deficient mice, Am. J. Pathol., 136(1):207-17 (1990).
Vogler et al., Enzyme replacement with recombinant beta-glucuronidase in the newborn mucopolysaccharidosis type VII mouse, Pediatr. Res., 34(6):837-40 (1993).
Vogler et al., Overcoming the blood-brain barrier with high-dose enzyme replacement therapy in murine mucopolysaccharidosis VII, Proc. Natl. Acad. Sci. USA, 102(41):14777-82 (2005).

(56) References Cited

OTHER PUBLICATIONS

Vyas et al., Ligand-receptor-mediated drug delivery: an emerging paradigm in cellular drug targeting, Crit. Rev. Ther. Drug Carrier Syst., 18(1):1-76 (2001).
Wadensten et al., Purification and characterization of recombinant human insulin-like growth factor II (IGF-II) expressed as a secreted fusion protein in *Escherichia coli,* Biotechnol. Appl. Biochem., 13(3):412-21 (1991).
Waheed et al., Human lysosomal acid phosphatase is transported as a transmembrane protein to lysosomes in transfected baby hamster kidney cells, EMBO J., 7(8):2351-8 (1988).
Waheed et al., Regulation of transferrin-mediated iron uptake by HFE, the protein defective in hereditary hemochromatosis, Proc. Natl. Acad. Sci. USA, 99(5):3117-22 (2002).
Wang et al., A study of protein-protein interactions in living cells using luminescence resonance energy transfer (LRET) from Renilla luciferase to Aequorea GFP, Mol. Gen. Genet., 264(5):578-87 (2001).
Wang et al., Regulation of embryonic growth and lysosomal targeting by the imprinted Igf2/Mpr gene, Nature, 372(6505):464-7 (1994).
Wang et al., The insulin A and B chains contain sufficient structural information to form the native molecule, Trends Biochem. Sci., 16(8):279-81 (1991).
Waszkowycz et al., PRO_LIGAND: an approach to de novo molecular design. 2. Design of novel molecules from molecular field analysis (MFA) models and pharmacophores, J. Med. Chem., 37(23):3994-4002 (1994).
Wells et al., Importance of hydrogen-bond formation in stabilizing the transition state of subtilisin. *Philos. Trans. R. Soc. London,* A:317:415-23 (1986).
Wilczak et al., Insulin-like growth factor system in serum and cerebrospinal fluid in patients with multiple sclerosis, Neurosci. Lett., 257(3):168-70 (1998).
Williams et al., Enzyme replacement in Pompe disease with an alpha-glucosidase-low density lipoprotein complex, Birth Defects Orig. Artic. Ser., 16(1):415-23 (1980).
Willingham et al., The receptosome: an intermediate organelle of receptor mediated endocytosis in cultured fibroblasts, Cell, 21(1):67-77 (1980).
Wisselaar et al., Structural and functional changes of lysosomal acid alpha-glucosidase during intracellular transport and maturation, J. Biol. Chem., 268(3):2223-31 (1993).
Wolfe et al., Murine Mucopolysaccharidosis type VII: a model system for somatic gene therapy of the central nervous system, chapter 20 (pp. 263-274) IN: Lowenstein et al. (eds.), Protocols for Gene Transfer in Neuroscience: Towards Gene Therapy of Neurological Disorders, John Wiley & Sons Ltd. (1996).
Written Opinion for PCT/US2005/004286 (2005).
Written Opinion for PCT/US2007/023881 (2009).
Yamashiro et al., Acidification of endocytic compartments and the intracellular pathways of ligands and receptors, J. Cell. Biochem., 26:231-46 (1984).
Yang et al., Probing the folding pathways of long R(3) insulin-like growth factor-I (LR(3)IGF-I) and IGF-I via capture and identification of disulfide intermediates by cyanylation methodology and mass spectrometry, J. Biol. Chem., 274(53):37598-604 (1999).
York et al., The rate of internalization of the mannose 6-phosphate/insulin-like growth factor II receptor is enhanced by multivalent ligand binding, J. Biol. Chem., 274(2):1164-71 (1999).
Yu et al., Insulin-like growth factors (IGF-I, free IGF-I and IGF-II) and insulin-like growth factor binding proteins (IGFBP-2, IGFBP-3, IGFBP-6, and ALS) in blood circulation, J. Clin. Lab Anal., 13(4):166-72 (1999).
Zarn et al., A mutant of human insulin-like growth factor II (IGF II) with the processing sites of proinsulin. Expression and binding studies of processed IGF II, Eur. J. Biochem., 210(3):665-9 (1992).
Zhu et al., Carbohydrate-remodelled acid alpha-glucosidase with higher affinity for the cation-independent mannose 6-phosphate receptor demonstrates improved delivery to muscles of Pompe mice, Biochem. J., 389 (Pt. 3):619-28 (2005).
Zhu et al., Conjugation of mannose 6-phosphate-containing oligosaccharides to acid alpha-glucosidase improves the clearance of glycogen in pompe mice, J. Biol. Chem., 279(48):50336-41 (2004).
Zoller et al., Oligonucleotide-directed mutagenesis using M13-derived vectors: an efficient and general procedure for the production of point mutations in any fragment of DNA, Nucleic Acids Res., 10(20):6487-500 (1982).
Zubieta et al., Response: Measuring our natural painkiller, Trends Neurosci., 25(2):69 (2002).
Restriction Requirement issued in parent application, U.S. Appl. No. 12/991,104 dated Jul. 25, 2012.
Office Action issued in parent application, U.S. Appl. No. 12/991,104 dated Oct. 12, 2012.
Amendment filed in U.S. Appl. No. 12/991,104 dated Jun. 11, 2013.
Advisory Action issued in U.S. Appl. No. 12/991,104 on Jun. 24, 2013.
Supplemental Response filed in U.S. Appl. No. 12/991,104, filed Aug. 12, 2013.
Office Action dated Mar. 14, 2013, issued in related U.S. Appl. No. 12/991,104.
Amendment filed on Jan. 9, 2013, in related U.S. Appl. No. 12/991,104.

* cited by examiner

Figure 2. SDS-PAGE of ZC-701 after treatment with PNGase F. The lane on the right has been additionally treated with furin.

Figure 3. Left. Schematic of ZC-701 mutants in which furin cleavage site is modified. Center. SDS-PAGE analysis of PNGase treated mutants after 3-7 days of cell culture. Right. SDS-PAGE analysis of PNGase-treated mutants treated with furin.

| Competitor | IGF2 | ZC-701 | 1751 | 1752 |
|---|---|---|---|---|
| $IC_{50}$ | 6.9 | 57.7 | 106.0 | 65.3 |

| Competitor | IGF2 | ZC-701 | 1763 |
|---|---|---|---|
| IC50 | 7.7 | 135.4 | 207.9 |

| | Insulin | ZC-1487-B26 | ZC-1487-B28 | ZC-701-GMP1 |
|---|---|---|---|---|
| IC50 | 40.5 | N/A | N/A | 607 |

LYSOSOMAL TARGETING PEPTIDES AND USES THEREOF

REFERENCE TO RELATED APPLICATIONS

This application is a continuation of U.S. patent application Ser. No. 12/991,104, filed Apr. 25, 2011, pending which is the U.S. national stage of International Application No. PCT/US09/43207, filed May 7, 2009, which claims the benefit of U.S. Provisional Patent Application No. 61/051,336, filed May 7, 2008 and U.S. Provisional Patent Application No. 61/144,106, filed Jan. 12, 2009, the contents of each of which are hereby incorporated by reference in their entireties.

BACKGROUND

Normally, mammalian lysosomal enzymes are synthesized in the cytosol and traverse the ER where they are glycosylated with N-linked, high mannose type carbohydrate. In the golgi, the high mannose carbohydrate is modified on lysosomal proteins by the addition of mannose-6-phosphate (M6P) which targets these proteins to the lysosome. The M6P-modified proteins are delivered to the lysosome via interaction with either of two M6P receptors. The most favorable form of modification is when two M6Ps are added to a high mannose carbohydrate.

More than forty lysosomal storage diseases (LSDs) are caused, directly or indirectly, by the absence of one or more lysosomal enzymes in the lysosome Enzyme replacement therapy for LSDs is being actively pursued. Therapy generally requires that LSD proteins be taken up and delivered to the lysosomes of a variety of cell types in an M6P-dependent fashion. One possible approach involves purifying an LSD protein and modifying it to incorporate a carbohydrate moiety with M6P. This modified material may be taken up by the cells more efficiently than unmodified LSD proteins due to interaction with M6P receptors on the cell surface.

The inventors of the present application have previously developed a peptide-based targeting technology that allows more efficient delivery of therapeutic enzymes to the lysosomes. This proprietary technology is termed Glycosylation Independent Lysosomal Targeting (GILT) because a peptide tag replaces M6P as the moiety targeting the lysosomes. Details of the GILT technology are described in U.S. Application Publication Nos. 2003-0082176, 2004-0006008, 2003-0072761, 2005-0281805, 2005-0244400, and international publications WO 03/032913, WO 03/032727, WO 02/087510, WO 03/102583, WO 2005/078077, the disclosures of all of which are hereby incorporated by reference.

SUMMARY OF THE INVENTION

The present invention provides further improved compositions and methods for efficient lysosomal targeting based on the GILT technology. Among other things, the present invention provides methods and compositions for targeting lysosomal enzymes to lysosomes using furin-resistant lysosomal targeting peptides. The present invention also provides methods and compositions for targeting lysosomal enzymes to lysosomes using a lysosomal targeting peptide that has reduced or diminished binding affinity for the insulin receptor. The present invention encompasses unexpected discovery that furin-resistant lysosomal targeting peptides according to the invention have reduced binding affinity for the insulin receptor.

In some embodiments, the present invention provides a furin-resistant IGF-II mutein. In some embodiments, the present invention provides a furin-resistant IGF-II mutein having an amino acid sequence at least 70% identical to mature human IGF-II (SEQ ID NO:1) and a mutation that abolishes at least one furin protease cleavage site.

In some embodiments, the present invention provides an IGF-II mutein comprising an amino acid sequence at least 70% identical to mature human IGF-II (SEQ ID NO:1) and a mutation that reduces or diminishes the binding affinity for the insulin receptor as compared to the wild-type human IGF-II.

In some embodiments, the furin-resistant IGF-II mutein has diminished binding affinity for the IGF-I receptor relative to the affinity of naturally-occurring human IGF-II for the IGF-I receptor.

In some embodiments, the present invention provides a targeted therapeutic fusion protein containing a lysosomal enzyme; and an IGF-II mutein having an amino acid sequence at least 70% identical to mature human IGF-II (SEQ ID NO:1), wherein the IGF-II mutein is resistant to furin cleavage and binds to the human cation-independent mannose-6-phosphate receptor in a mannose-6-phosphate-independent manner.

In some embodiments, the present invention provides a targeted therapeutic fusion protein containing a lysosomal enzyme; and an IGF-II mutein having an amino acid sequence at least 70% identical to mature human IGF-II (SEQ ID NO:1), and having diminished binding affinity for the insulin receptor relative to the affinity of naturally-occurring human IGF-II for the insulin receptor; wherein the IGF-II mutein binds to the human cation-independent mannose-6-phosphate receptor in a mannose-6-phosphate-independent manner.

In some embodiments, the present invention provides a targeted therapeutic fusion protein containing a lysosomal enzyme; and an IGF-II mutein having an amino acid sequence at least 70% identical to mature human IGF-II (SEQ ID NO:1), and having diminished binding affinity for the insulin receptor relative to the affinity of naturally-occurring human IGF-II for the insulin receptor; wherein the IGF-II mutein is resistant to furin cleavage and binds to the human cation-independent mannose-6-phosphate receptor in a mannose-6-phosphate-independent manner.

In some embodiments, an IGF-II mutein suitable for the invention includes a mutation within a region corresponding to amino acids 30-40 of SEQ ID NO:1. In some embodiments, an IGF-II mutein suitable for the invention includes a mutation within a region corresponding to amino acids 34-40 of SEQ ID NO:1 such that the mutation abolishes at least one furin protease cleavage site. In some embodiments, a suitable mutation is an amino acid substitution, deletion and/or insertion. In some embodiments, the mutation is an amino acid substitution at a position corresponding to Arg37 or Arg40 of SEQ ID NO:1. In some embodiments, the amino acid substitution is a Lys or Ala substitution.

In some embodiments, a suitable mutation is a deletion or replacement of amino acid residues corresponding to positions selected from the group consisting of 31-40, 32-40, 33-40, 34-40, 30-39, 31-39, 32-39, 34-37, 32-39, 3-39, 34-39, 35-39, 36-39, 37-40, 34-40 of SEQ ID NO:1, and combinations thereof.

In some embodiments, an IGF-II mutein according to the invention further contains a deletion or a replacement of amino acids corresponding to positions 2-7 of SEQ ID NO:1. In some embodiments, an IGF-II mutein according to the invention further includes a deletion or a replacement of amino acids corresponding to positions 1-7 of SEQ NO:1. In some embodiments, an IGF-II mutein according to the invention further contains a deletion or a replacement of amino acids corresponding to positions 62-67 of SEQ ID NO:1. In some embodiments, an IGF-II mutein according to the invention further contains an amino acid substitution at a position corresponding to Tyr27, Leu43, or Ser26 of SEQ ID NO:1. In some embodiments, an IGF-II mutein according to the invention contains at least an amino acid substitution selected from the group consisting of Tyr27Leu, Leu43Val, Ser26Phe and combinations thereof. In some embodiments, an IGF-II mutein according to the invention contains amino acids corresponding to positions 48-55 of SEQ ID NO:1. In some embodiments, an IGF-II mutein according to the invention contains at least three amino acids selected from the group consisting of amino acids corresponding to positions 8, 48, 49, 50, 54, and 55 of SEQ ID NO:1. In some embodiments, an IGF-II mutein of the invention contains, at positions corresponding to positions 54 and 55 of SEQ ID NO:1, amino acids each of which is uncharged or negatively charged at pH 7.4. In some embodiments, the IGF-II mutein has diminished binding affinity for the IGF-I receptor relative to the affinity of naturally-occurring human IGF-II for the IGF-I receptor.

In some embodiments, a lysosomal enzyme suitable for the invention is human acid alpha-glucosidase (GAA), or a functional variant thereof. In some embodiments, a lysosomal enzyme suitable for the invention includes amino acids 70-952 of human GAA.

In some embodiments, a targeted therapeutic fusion protein of the invention further includes a spacer between the lysosomal enzyme and the furin-resistant IGF-II mutein. In some embodiments, the spacer contains an amino acid sequence Gly-Ala-Pro.

The present invention also provides nucleic acids encoding the IGF-II mutein or the targeted therapeutic fusion protein as described in various embodiments above. The present invention further provides various cells containing the nucleic acid of the invention.

The present invention provides pharmaceutical compositions suitable for treating lysosomal storage disease containing a therapeutically effective amount of a targeted therapeutic fusion protein of the invention. The invention further provides methods of treating lysosomal storage diseases comprising administering to a subject in need of treatment a targeted therapeutic fusion protein according to the invention. In some embodiments, the lysosomal storage disease is Pompe Disease. In some embodiments, the lysosomal storage disease is Fabry Disease. In some embodiments, the lysosomal storage disease is Gaucher Disease.

In another aspect, the present invention provides a method of producing a targeted therapeutic fusion protein including a step of culturing mammalian cells in a cell culture medium, wherein the mammalian cells carry the nucleic acid of the invention, in particular, as described in various embodiments herein; and the culturing is performed under conditions that permit expression of the targeted therapeutic fusion protein.

In yet another aspect, the present invention provides a method of producing a targeted therapeutic fusion protein including a step of culturing furin-deficient cells (e.g., furin-deficient mammalian cells) in a cell culture medium, wherein the furin-deficient cells carry a nucleic acid encoding a fusion protein comprising a lysosomal enzyme and an IGF-II mutein having an amino acid sequence at least 70% identical to mature human IGF-II (SEQ ID NO:1), wherein the IGF-II mutein binds to the human cation-independent mannose-6-phosphate receptor in a mannose-6-phosphate-independent manner; and wherein the culturing is performed under conditions that permit expression of the targeted therapeutic fusion protein.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION ION OF THE DRAWINGS

The drawings are for illustration purposes only, not for limitation.

FIG. 1 illustrates a map of N-terminus of ZC-701. Two amino acid residues boxed are sites of cleavage events. The first is the site of signal peptide cleavage, the second is the site of a furin cleavage.

FIG. 2 illustrates an exemplary SDS-PAGE analysis of ZC-701 after ea ent with PNGase F. The lane on the right has been additionally treated with furin.

FIG. 3 Left: Schematic illustration of exemplary ZC-701 mutants in which furin cleavage site is modified. Center: Exemplary SDS-PAGE analysis of PNGase treated mutants after 3-7 days of cell culture. Right: Exemplary SDS-PAGE analysis of PNGase-treated mutants treated with furin.

Figure 10:
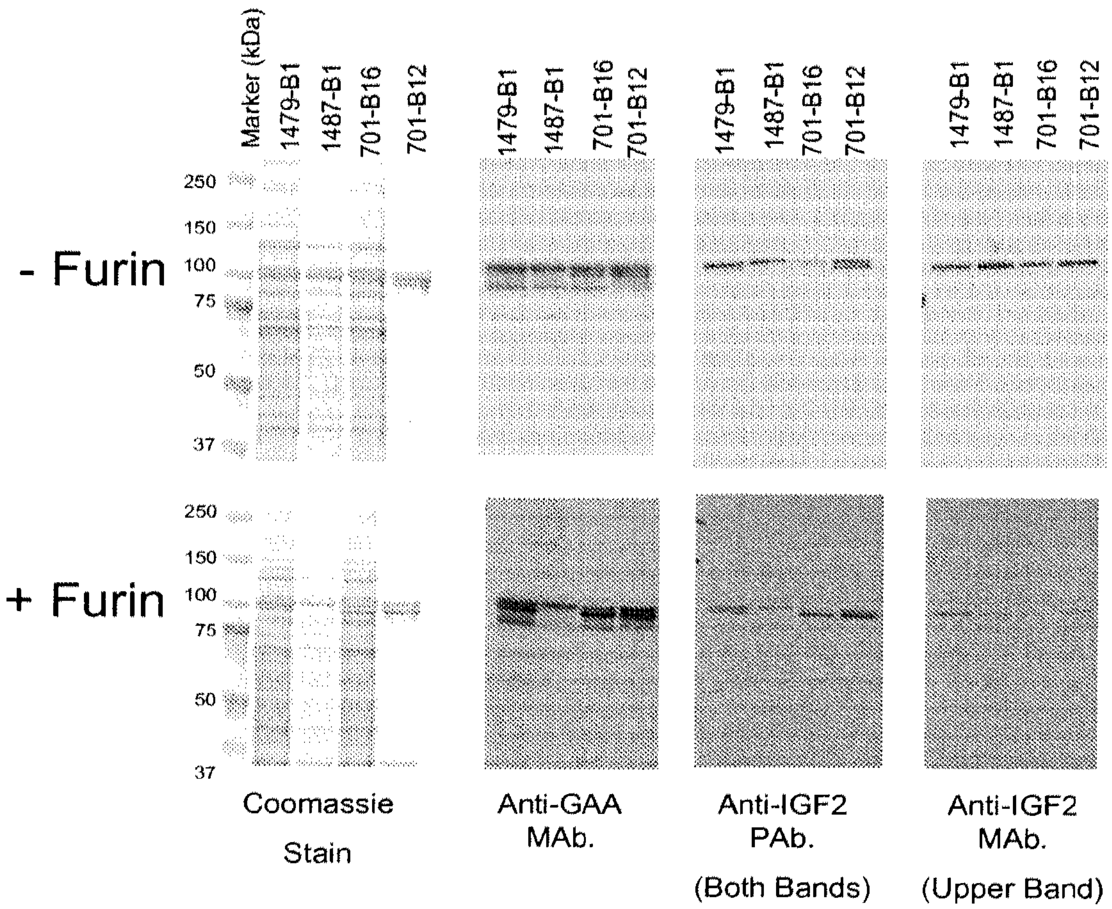

FIG. 10 illustrates exemplary analysis of partially purified GILT-tagged GAA from transient transfections. HEK293 cells were transfected with constructs 1479, 1487 or ZC-701. After harvest, culture supernatants were partially purified by Hydrophobic Interaction Chromatography (HIC). All samples were treated with PNGase prior to electrophoresis. Left panels: SDS-PAGE of partially purified proteins. Purified ZC-701 B12 is shown as a control. Right panels: Immunoblot analysis of the partially purified proteins. The indicated primary antibody was used. Bottom panels were additionally treated with exogenous furin. The protein encoded by construct 1487 is identical in sequence to that encoded by construct 1461 (R37A). The protein encoded by construct 1479 is identical to that encoded by construct 1459 (R37K).

Figure 11:
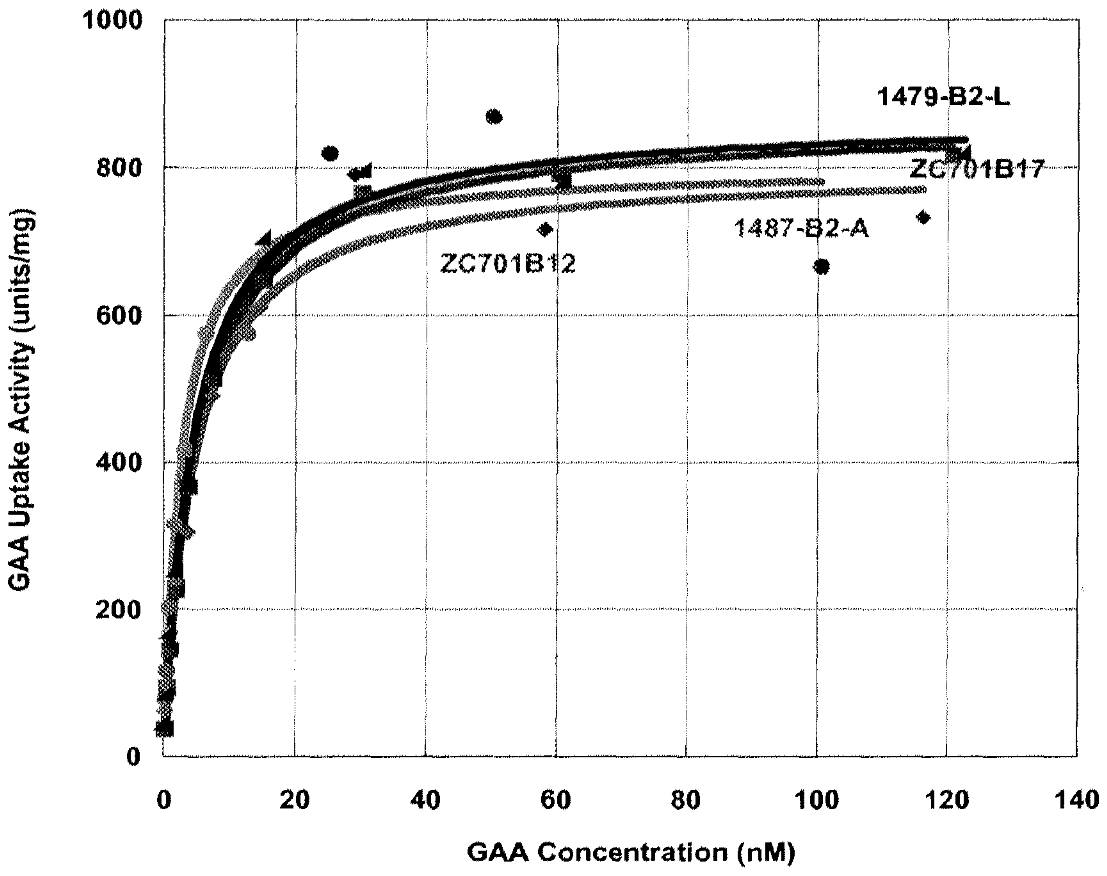

FIG. 11 illustrates exemplary uptake results of exemplary furin resistant GILT-tagged GAA into rat L6 myoblasts. $K_{uptakes}$ for protein 1479, 1487, ZC-701, and purified ZC-701 are 4.5 nM, 4.4 nM, 5.0 nM and 2.6 nM respectively. The protein encoded by construct 1487 is identical in sequence to that encoded by construct 1461 in FIG. 3 (R37A). The protein encoded by construct 1479 is identical to that encoded by construct 1459 in FIG. 3 (R37K).

DEFINITIONS

Amelioration: As used herein, the term "amelioration" is meant the prevention, reduction or palliation of a state, or improvement of the state of a subject. Amelioration includes, but does not require complete recovery or complete prevention of a disease condition. In some embodiments, amelioration includes reduction of accumulated materials inside lysosomes of relevant diseases tissues.

Furin-resistant IGF-II mutein: As used herein, the term "furin-resistant IGF-II mutein" refers to an IGF-II-based peptide containing an altered amino acid sequence that abolishes at least one native furin protease cleavage site or changes a sequence close or adjacent to a native furin protease cleavage site such that the furin cleavage is prevented, inhibited, reduced, or slowed down as compared to a wild-type human IGF-II peptide. As used herein, a furin-resistant IGF-II mutein is also referred to as an IGF-II mutein that is resistant to furin.

Furin protease cleavage site: As used herein, the term "furin protease cleavage site" (also referred to as "furin cleavage site" or "furin cleavage sequence") refers to the amino acid sequence of a peptide or protein that serves as a recognition sequence for enzymatic protease cleavage by furin or furin-like proteases. Typically, a furin protease cleavage site has a consensus sequence Arg-X-X-Arg (SEQ ID NO: 2), X is any amino acid. The cleavage site is positioned after the carboxy-terminal arginine (Arg) residue in the sequence. In some embodiments, a furin cleavage site may have a consensus sequence Lys/Arg-X-X-X-Lys/Arg-Arg (SEQ ID NO: 3), X is any amino acid. The cleavage site is positioned after the carboxy-terminal arginine (Arg) residue in the sequence.

Furin: As used herein, the term "furin" refers to any protease that can recognize and cleave the furin protease cleavage site as defined herein, including furin or furin-like protease. Furin is also known as paired basic amino acid cleaving enzyme (PACE). Furin belongs to the subtilisin-like proprotein convertase family. The gene encoding furin was known as FUR (FES Upstream Region).

Furin-de lent cells: As used herein, the term "furin-deficient cells" refers to any cells whose furin protease activity is inhibited, reduced or eliminated. Furin-deficient cells include both mammalian and non-mammalian cells that do not produce furin or produce reduced amount of furin or defective furin protease.

Glycosylation Independent Lysosomal Targeting: As used herein, the term "glycosylation independent lysosomal targeting" (also referred to as "GILT") refer to lysosomal targeting that is mannose-6-phosphate-independent.

Human acid alpha-glucosidase: As used herein, the term "human acid alpha-glucosidase" (also referred to as "GAA") refers to precursor wild-type form of human GAA or a functional variant that is capable of reducing glycogen levels in mammalian lysosomes or that can rescue or ameliorate one or more Pompe disease symptoms.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of lysosomal storage disease (e.g., Pompe disease) as the individual being treated, who is about the same age as the individual being treated (to ensure that the stages of the disease in the treated individual and the control individual(s) are comparable).

Individual, subject, patient: As used herein, the terms "subject," "individual" or "patient" refer to a human or a non-human mammalian subject. The individual (also referred to as "patient" or "subject") being treated is an individual (fetus, infant, child, adolescent, or adult human) suffering from a lysosomal storage disease, for example, Pompe disease (i.e., either infantile-, juvenile-, or adult-onset Pompe disease) or having the potential to develop a lysosomal storage disease (e.g., Pompe disease).

Lysosomal storage diseases: As used herein, "lysosomal storage diseases" refer to a group of genetic disorders that result from deficiency in at least one of the enzymes (e.g., acid hydrolases) that are required to break macromolecules down to peptides, amino acids, monosaccharides, nucleic acids and fatty acids in lysosomes. As a result, individuals suffering from lysosomal storage diseases have accumulated materials in lysosomes. Exemplary lysosomal storage diseases are listed in Table 1.

Lysosomal enzyme: As used herein, the term "lysosomal enzyme" refers to any enzyme that is capable of reducing accumulated materials in mammalian lysosomes or that can rescue or ameliorate one or more lysosomal storage disease symptoms. Lysosomal enzymes suitable for the invention include both wild-type or modified lysosomal enzymes and can be produced using recombinant and synthetic methods or purified from nature sources. Exemplary lysosomal enzymes are listed in Table 1.

Spacer: As used herein, the term "spacer" (also referred to as "linker") refers to a peptide sequence between two protein moieties in a fusion protein. A spacer is generally designed to be flexible or to interpose a structure, such as an alpha-helix, between the two protein moieties. A spacer can be relatively short, such as the sequence Gly-Ala-Pro (SEQ ID NO: 4) or Gly-Gly-Gly-Gly-Gly-Pro (SEQ ID NO: 5), or can be longer, such as, for example, 10-25 amino acids in length.

Therapeutically effective amount: As used herein, the term "therapeutically effective amount" refers to an amount of a targeted therapeutic fusion protein which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic fusion protein or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic fusion protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Treatment: As used herein, the term "treatment" (also "treat" or "treating") refers to any administration of a therapeutic fusion protein that partially or completely alleviates, ameliorates, relieves, inhibits, delays onset of, reduces severity of and/or reduces incidence of one or more symptoms or features of a particular disease, disorder, and/or condition.

Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. For example, treatment can refer to improvement of cardiac status (e.g., increase of end-diastolic and/or end-systolic volumes, or reduction, amelioration or prevention of the progressive cardiomyopathy that is typically found in Pompe disease) or of pulmonary function (e.g., increase in crying vital capacity over baseline capacity, and/or normalization of oxygen desaturation during crying); improvement in neurodevelopment and/or motor skills (e.g., increase in AIMS score); reduction of glycogen levels in tissue of the individual affected by the disease; or any combination of these effects. In some embodiments, treatment includes improvement of glycogen clearance, particularly in reduction or prevention of Pompe disease-associated cardiomyopathy.

As used in this application, the terms "about" and "approximately" are used as equivalents. Any numerals used in this application with or without about/approximately are meant to cover any normal fluctuations appreciated by one of ordinary skill in the relevant art.

DETAILED DESCRIPTION OF THE INVENTION

The present invention provides improved methods and compositions for targeting lysosomal enzymes based on the glycosylation-independent lysosomal targeting (GILT) technology. Among other things, the present invention provides IGF-II muteins that are resistant to furin and/or has reduced or diminished binding affinity for the insulin receptor and targeted therapeutic fusion proteins containing an IGF-II mutein of the invention. The present invention also provides methods of making and using the same.

Various aspects of the invention are described in detail in the following sections. The use of sections is not meant to limit the invention. Each section can apply to any aspect of the invention. In this application, the use of "or" means "and/or" unless stated otherwise.

Lysosomal Enzymes

A lysosomal enzyme suitable for the invention includes any enzyme that is capable of reducing accumulated materials in mammalian lysosomes or that can rescue or ameliorate one or more lysosomal storage disease symptoms. Suitable lysosomal enzymes include both wild-type or modified lysosomal enzymes and can be produced using recombinant or synthetic methods or purified from nature sources. Exemplary lysosomal enzymes are listed in Table 1.

TABLE 1

Lysosomal Storage Diseases and associated enzyme defects

| Disease Name | Enzyme Defect | Substance Stored |
|---|---|---|
| A. Glycogenosis Disorders | | |
| Pompe Disease | Acid-a1,4-Glucosidase | Glycogen α1-4 linked Oligosaccharides |
| B. Glycolipidosis Disorders | | |
| GM1 Gangliodsidosis | β-Galactosidase | $GM_1$ Gangliosides |
| Tay-Sachs Disease | β-Hexosaminidase A | $GM_2$ Ganglioside |
| GM2 Gangliosidosis: AB Variant | $GM_2$ Activator Protein | $GM_2$ Ganglioside |
| Sandhoff Disease | β-Hexosaminidase A&B | $GM_2$ Ganglioside |
| Fabry Disease | α-Galactosidase A | Globosides |
| Gaucher Disease | Glucocerebrosidase | Glucosylceramide |
| Metachromatic Leukodystrophy | Arylsulfatase A | Sulphatides |
| Krabbe Disease | Galactosylceramidase | Galactocerebroside |
| Niemann-Pick, Types A and B | Acid Sphingomyelinase | Sphingomyelin |
| Niemann-Pick, Type C | Cholesterol Esterification Defect | Sphingomyelin |
| Niemann-Pick, Type D | Unknown | Sphingomyelin |
| Farber Disease | Acid Ceramidase | Ceramide |
| Wolman Disease | Acid Lipase | Cholesteryl Esters |
| C. Mucopolysaccharide Disorders | | |
| Hurler Syndrome (MPS IH) | α-L-Iduronidase | Heparan & Dermatan Sulfates |
| Scheie Syndrome (MPS IS) | α-L-Iduronidase | Heparan & Dermatan, Sulfates |
| Hurler-Scheie (MPS IH/S) | α-L-Iduronidase | Heparan & Dermatan Sulfates |
| Hunter Syndrome (MPS II) | Iduronate Sulfatase | Heparan & Dermatan Sulfates |
| Sanfilippo A (MPS IIIA) | Heparan N-Sulfatase | Heparan Sulfate |
| Sanfilippo B (MPS IIIB) | α-N-Acetylglucosaminidase | Heparan Sulfate |
| Sanfilippo C (MPS IIIC) | Acetyl-CoA-Glucosaminide Acetyltransferase | Heparan Sulfate |
| Sanfilippo D (MPS IIID) | N-Acetylglucosamine-6-Sulfatase | Heparan Sulfate |
| Morquio A (MPS IVA) | Galactosamine-6-Sulfatase | Keratan Sulfate |
| Morquio B (MPS IVB) | β-Galactosidase | Keratan Sulfate |
| Maroteaux-Lamy (MPS VI) | Arylsulfatase B | Dermatan Sulfate |
| Sly Syndrome (MPS VII) | β-Glucuronidase | |
| D. Oligosaccharide/Glycoprotein Disorders | | |
| α-Mannosidosis | α-Mannosidase | Mannose/Oligosaccharides |
| β-Mannosidosis | β-Mannosidosis | Mannose/Oligosaccharides |
| Fucosidosis | α-L-Fucosidase | Fucosyl Oligosaccharides |
| Aspartylglucosaminuria | N-Aspartyl-β-Glucosaminidase | Aspartylglucosamine Asparagines |
| Sialidosis (Mucolipidosis I) | α-Neuraminidase | Sialyloligosaccharides |
| Galactosialidosis (Goldberg Syndrome) | Lysosomal Protective Protein Deficiency | Sialyloligosaccharides |
| Schindler Disease | α-N-Acetyl-Galactosaminidase | |
| E. Lysosomal Enzyme Transport Disorders | | |
| Mucolipidosis II (I-Cell Disease) | N-Acetylglucosamine-1-Phosphotransferase | Heparan Sulfate |
| Mucolipidosis III (Pseudo-Hurler Polydystrophy) | Same as ML II | |
| F. Lysosomal Membrane Transport Disorders | | |
| Cystinosis | Cystine Transport Protein | Free Cystine |
| Salla Disease | Sialic Acid Transport Protein | Free Sialic Acid and Glucuronic Acid |

TABLE 1-continued

Lysosomal Storage Diseases and associated enzyme defects

| Disease Name | Enzyme Defect | Substance Stored |
|---|---|---|
| Infantile Sialic Acid Storage Disease | Sialic Acid Transport Protein | Free Sialic Acid and Glucuronic Acid |
| | G. Other | |
| Batten Disease (Juvenile Neuronal Ceroid Lipofuscinosis) | Unknown | Lipofuscins |
| Infantile Neuronal Ceroid Lipofuscinosis | Palmitoyl-Protein Thioesterase | Lipofuscins |
| Mucolipidosis IV | Unknown | Gangliosides & Hyaluronic Acid |
| Prosaposin | Saposins A, B, C or D | |

In some embodiments, a lysosomal enzyme suitable for the invention includes a polypeptide sequence having 50-100%, including 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100%, sequence identity to the naturally-occurring polynucleotide sequence of a human enzyme shown in Tables 1, while still encoding a protein that is capable of reducing accumulated materials in mammalian lysosomes or that can rescue or ameliorate one or more lysosomal storage disease symptoms.

"Percent (%) amino acid sequence identity" with respect to the lysosomal enzyme sequences is defined as the percentage of amino acid residues in a candidate sequence that are identical with the amino acid residues in the naturally-occurring human enzyme sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. Preferably, the WU-BLAST-2 software is used to determine amino acid sequence identity (Altschul et al., *Methods in Enzymology* 266, 460-480 (1996); http://blast.wustUedu/blast/README.html). WU-BLAST-2 uses several search parameters, most of which are set to the default values. The adjustable parameters are set with the following values; overlap span=1, overlap fraction=0.125, world threshold (T)=11. HSP score (S) and HSP S2 parameters are dynamic values and are established by the program itself, depending upon the composition of the particular sequence, however, the minimum values may be adjusted and are set as indicated above.

Pompe Disease

One exemplary lysosomal storage disease is Pompe disease. Pompe disease is a rare genetic disorder caused by a deficiency in the enzyme acid alpha-glucosidase (GAA), which is needed to break down glycogen, a stored form of sugar used for energy. Pompe disease is also known as glycogen storage disease type II, GSD II, type II glycogen storage disease, glycogenosis type II, acid maltase deficiency, alpha-1,4-glucosidase deficiency, cardiomegalia glycogenic diffusa, and cardiac form of generalized glycogenosis. The build-up of glycogen causes progressive muscle weakness (myopathy) throughout the body and affects various body tissues, particularly in the heart, skeletal muscles, liver, respiratory and nervous system.

The presenting clinical manifestations of Pompe disease can vary widely depending on the age of disease onset and residual GAA activity. Residual GAA activity correlates with both the amount and tissue distribution of glycogen accumulation as well as the severity of the disease. Infantile-onset Pompe disease (less than 1% of normal GAA activity) is the most severe form and is characterized by hypotonia, generalized muscle weakness, and hypertrophic cardiomyopathy, and massive glycogen accumulation in cardiac and other muscle tissues. Death usually occurs within one year of birth due to cardiorespiratory failure. Hirschhorn et al. (2001) "Glycogen Storage Disease Type II: Acid Alpha-glucosidase (Acid Maltase) Deficiency," in Scriver et al., eds., *The Metabolic and Molecular Basis of Inherited Disease,* 8th Ed., New York: McGraw-Hill, 3389-3420. Juvenile-onset (1-10% of normal GAA activity) and adult-onset (10-40% of normal GAA activity) Pompe disease are more clinically heterogeneous, with greater variation in age of onset, clinical presentation, and disease progression. Juvenile- and adult-onset Pompe disease are generally characterized by lack of severe cardiac involvement, later age of onset, and slower disease progression, but eventual respiratory or limb muscle involvement results in significant morbidity and mortality. While life expectancy can vary, death generally occurs due to respiratory failure. Hirschhorn et al. (2001) "Glycogen Storage Disease Type II: Acid Alpha-glucosidase (Acid Maltase) Deficiency," in Scriver et al., eds., *The Metabolic and Molecular Basis of Inherited Disease,* 8th Ed., New York: McGraw-Hill, 3389-3420.

A GAA enzyme suitable for treating Pompe disease includes a wild-type human GAA, or a fragment or sequence variant thereof which retains the ability to cleave α1-4 linkages in linear oligosaccharides.

Enzyme Replacement Therapy

Enzyme replacement therapy (ERT) is a therapeutic strategy to correct an enzyme deficiency by infusing the missing enzyme into the bloodstream. As the blood perfuses patient tissues, enzyme is taken up by cells and transported to the lysosome, where the enzyme acts to eliminate material that has accumulated in the lysosomes due to the enzyme deficiency. For lysosomal enzyme replacement therapy to be effective, the therapeutic enzyme must be delivered to lysosomes in the appropriate cells in tissues where the storage defect is manifest. Conventional lysosomal enzyme replacement therapeutics are delivered using carbohydrates naturally attached to the protein to engage specific receptors on the surface of the target cells. One receptor, the cation-independent M6P receptor (CI-MPR), is particularly useful for targeting replacement lysosomal enzymes because the CI-MPR is present on the surface of most cell types.

The terms "cation-independent mannose-6-phosphate receptor (CI-MPR)," "M6P/IGF-II receptor," "CI-MPR/IGF-II receptor," "IGF-II receptor" or "IGF2 Receptor," or abbreviations thereof, are used interchangeably herein, referring to the cellular receptor which binds both M6P and IGF-II.

Glycosylation Independent Lysosomal Targeting

We have developed a Glycosylation Independent Lysosomal Targeting (GILT) technology to target therapeutic enzymes to lysosomes. Specifically, the GILT technology uses a peptide tag instead of M6P to engage the CI-MPR for lysosomal targeting. Typically, a GILT tag is a protein, peptide, or other moiety that binds the CI-MPR in a mannose-6-phosphate-independent mariner. Advantageously, this technology mimics the normal biological mechanism for uptake of lysosomal enzymes, yet does so in a manner independent of mannose-6-phosphate.

A preferred GILT tag is derived from human insulin-like growth factor II (IGF-II). Human IGF-II is a high affinity ligand for the CI-MPR, which is also referred to as IGF-II receptor. Binding of GILT-tagged therapeutic enzymes to the M6P/IGF-II receptor targets the protein to the lysosome via the endocytic pathway. This method has numerous advantages over methods involving glycosylation including simplicity and cost effectiveness, because once the protein is isolated, no further modifications need be made.

Detailed description of the GILT technology and GILT tag can be found in U.S. Publication Nos. 20030082176, 20040006008, 20040005309, and 20050281805, the teachings of all of which are hereby incorporated by references in their entireties.

Furin-Resistant GILT Tag

During the course of development of GILT-tagged lysosomal enzymes for treating lysosomal storage disease, it has become apparent that the IGF-II derived GILT tag may be subjected to proteolytic cleavage by furin during production in mammalian cells (see the examples section). Furin protease typically recognizes and cleaves a cleavage site having a consensus sequence Arg-X-X-Arg (SEQ ID NO: 2), X is any amino acid. The cleavage site is positioned after the carboxy-terminal arginine (Arg) residue in the sequence. In some embodiments, a furin cleavage site has a consensus sequence Lys/Arg-X-X-X-Lys/Arg-Arg (SEQ ID NO: 3), X is any amino acid. The cleavage site is positioned after the carboxy-terminal arginine (Arg) residue in the sequence. As used herein, the term “furin” refers to any protease that can recognize and cleave the furin protease cleavage site as defined herein, including furin or furin-like protease. Furin is also known as paired basic amino acid cleaving enzyme (PACE). Furin belongs to the subtilisin-like proprotein convertase family that includes PC3, a protease responsible for maturation of proinsulin in pancreatic islet cells. The gene encoding furin was known as FUR (FES Upstream Region).

The mature human IGF-II peptide sequence is shown below.

```
                                          (SEQ ID NO: 1)
                                        ↓  ↓
AYRPSETLCGGELVDTLQFVCGDRGFYFSRPASRVSRRSRGIVEECCFRS

CDLALLETYCATPAKSE
```

As can be seen, the mature human IGF-II contains two potential overlapping furin cleavage sites between residues 34-40 (bolded and underlined). Arrows point to two potential furin cleavage positions.

We have developed modified GILT tags that are resistant to cleavage by furin and still retain ability to bind to the CI-MPR in a mannose-6-phosphate-independent manner. Specifically, furin-resistant GILT tags can be designed by mutating the amino acid sequence at one or more furin cleavage sites such that the mutation abolishes at least one furin cleavage site. Thus, in some embodiments, a furin-resistant GILT tag is a furin-resistant IGF-II mutein containing a mutation that abolishes at least one furin protease cleavage site or changes a sequence adjacent to the furin protease cleavage site such that the furin cleavage is prevented, inhibited, reduced or slowed down as compared to a wild-type IGF-II peptide (e.g., wild-type human mature IGF-II). Typically, a suitable mutation does not impact the ability of the furin-resistant GILT tag to bind to the human cation-independent mannose-6-phosphate receptor. In particular, a furin-resistant IGF-II mutein suitable for the invention binds to the human cation-independent mannose-6-phosphate receptor in a mannose-6-phosphate-independent manner with a dissociation constant of $10^{-7}$ M or less (e.g., $10^{-8}$, $10^{-9}$, $10^{-10}$, $10^{-11}$, or less) at pH 7.4. In some embodiments, a furin-resistant IGF-II mutein contains a mutation within a region corresponding to amino acids 30-40 (e.g., 31-40, 32-40, 33-40, 34-40, 30-39, 31-39, 32-39, 34-37, 32-39, 33-39, 34-39, 35-39, 36-39, 37-40, 34-40) of SEQ ID NO:1. In some embodiments, a suitable mutation abolishes at least one furin protease cleavage site. A mutation can be amino acid substitutions, deletions, insertions. For example, any one amino acid within the region corresponding to residues 30-40 (e.g., 31-40, 32-40, 33-40, 34-40, 30-39, 31-39, 32-39, 34-37, 32-39, 33-39, 34-39, 35-39, 36-39, 37-40, 34-40) of SEQ ID NO:1 can be substituted with any other amino acid or deleted. For example, substitutions at position 34 may affect furin recognition of the first cleavage site. Insertion of one or more additional amino acids within each recognition site may abolish one or both furin cleavage sites. Deletion of one or more of the residues in the degenerate positions may also abolish both furin cleavage sites.

In some embodiments, a furin-resistant IGF-II mutein contains amino acid substitutions at positions corresponding to Arg37 or Arg40 of SEQ ID NO:1. In some embodiments, a furin-resistant IGF-II mutein contains a Lys or Ala substitution at positions Arg37 or Arg40. Other substitutions are possible, including combinations of Lys and/or Ala mutations at both positions 37 and 40, or substitutions of amino acids other than Lys or Ala.

In some embodiments, the furin-resistant IGF-II mutein suitable for the invention may contain additional mutations. For example, up to 30% or more of the residues of SEQ ID NO:1 may be changed (e.g., up to 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30% or more residues may be changed). Thus, a furin-resistant IGF-II mutein suitable for the invention may have an amino acid sequence at least 70%, including at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99%, identical to SEQ ID NO:1.

In some embodiments, a furin-resistant IGF-II mutein suitable for the invention is targeted specifically to the CI-MPR. Particularly useful are mutations in the IGF-II polypeptide that result in a protein that binds the CI-MPR with high affinity (e.g., with a dissociation constant of $10^{-7}$ M or less at pH 7.4) while binding other receptors known to be bound by IGF-II with reduced affinity relative to native IGF-II. For example, a furin-resistant mutein suitable for the invention can be modified to have diminished binding affinity for the IGF-I receptor relative to the affinity of naturally-occurring human IGF-II for the IGF-I receptor. For example, substitution of IGF-II residues Tyr 27 with Leu, Leu 43 with Val or Ser 26 with Phe diminishes the affinity of IGF-II for the IGF-I receptor by 94-, 56-, and 4-fold respectively (Torres et al. (1995) *J. Mol. Biol.* 248(2):385-401). Deletion of residues 1-7 of human IGF-II resulted in a 30-fold decrease in affinity for the human IGF-I receptor and a concomitant 12 fold increase in affinity for the rat IGF-II receptor (Hashimoto et al. (1995) *J. Biol. Chem.* 270(30):18013-8). The NMR structure of IGF-II shows that Thr 7 is located near residues 48 Phe and 50 Ser as well as near the 9 Cys-47 Cys disulfide bridge. It is thought that interaction of Thr 7 with these residues can stabilize the flexible N-terminal hexapeptide required for IGF-I receptor binding (Terasawa et al. (1994) *EMBO J.* 13(23)5590-7). At the same time this interaction can modulate binding to the IGF-II receptor. Truncation of the C-terminus of IGF-II (residues 62-67) also appear to lower the affinity of IGF-II for the IGF-I receptor by 5 fold (Roth et al. (1991) *Biochem. Biophys. Res. Commun.* 181(2):907-14).

The binding surfaces for the IGF-I and cation-independent M6P receptors are on separate faces of IGF-II. Based on structural and mutational data, functional cation-independent M6P binding domains can be constructed that are substantially smaller than human IGF-II. For example, the amino terminal amino acids (e.g., 1-7 or 2-7) and/or the carboxy terminal residues 62-67 can be deleted or replaced. Additionally, amino acids 29-40 can likely be eliminated or replaced without altering the folding of the remainder of the polypeptide or binding to the cation-independent M6P receptor. Thus, a targeting moiety including amino acids 8-28 and 41-61 can be constructed. These stretches of amino acids could perhaps be joined directly or separated by a linker. Alternatively, amino acids 8-28 and 41-61 can be provided on separate polypeptide chains. Comparable domains of insulin, which is homologous to IGF-II and has a tertiary structure closely related to the structure of IGF-II, have sufficient structural information to permit proper refolding into the appropriate tertiary structure, even when present in separate polypeptide chains (Wang et al. (1991) *Trends Biochem. Sci.* 279-281). Thus, for example, amino acids 8-28, or a conservative substitution variant thereof, could be fused to a lysosomal enzyme; the resulting fusion protein could be admixed with amino acids 41-61, or a conservative substitution variant thereof, and administered to a patient.

IGF-II can also be modified to minimize binding to serum IGF-binding proteins (Baxter (2000) *Am. J. Physiol Endocrinol Metab.* 278(6):967-76) to avoid sequestration of IGF-II/GILT constructs. A number of studies have localized residues in IGF-II necessary for binding to IGF-binding proteins. Constructs with mutations at these residues can be screened for retention of high affinity binding to the M6P/IGF-II receptor and for reduced affinity for IGF-binding proteins. For example, replacing Phe 26 of IGF-II with Ser is reported to reduce affinity of IGF-II for IGFBP-1 and -6 with no effect on binding to the M6P/IGF-II receptor (Bach et al. (1993) *J. Biol. Chem.* 268(13):9246-54). Other substitutions, such as Lys for Glu 9, can also be advantageous. The analogous mutations, separately or in combination, in a region of IGF-I that is highly conserved with IGF-II result in large decreases in IGF-BP binding (Magee et al. (1999) Biochemistry 38(48): 15863-70).

An alternate approach is to identify minimal regions of IGF-II that can bind with high affinity to the M6P/IGF-II receptor. The residues that have been implicated in IGF-II binding to the M6P/IGF-II receptor mostly cluster on one face of IGF-II (Terasawa et al. (1994) EMBO J. 13(23):5590-7). Although IGF-II tertiary structure is normally maintained by three intramolecular disulfide bonds, a peptide incorporating the amino acid sequence on the M6P/IGF-II receptor binding surface of IGF-II can be designed to fold properly and have binding activity. Such a minimal binding peptide is a highly preferred lysosomal targeting domain. For example, a preferred lysosomal targeting domain is amino acids 8-67 of human IGF-II. Designed peptides, based on the region around amino acids 48-55, which bind to the M6P/IGF-II receptor, are also desirable lysosomal targeting domains. Alternatively, a random library of peptides can be screened for the ability to bind the M6P/IGF-II receptor either via a yeast two hybrid assay, or via a phage display type assay.

Binding Affinity for the Insulin Receptor

The inventors of the present application discovered unexpectedly that many furin-resistant IGF-II muteins described herein have reduced or diminished binding affinity for the insulin receptor. Thus, in some embodiments, a peptide tag suitable for the invention has reduced or diminished binding affinity for the insulin receptor relative to the affinity of naturally-occurring human IGF-II for the insulin receptor. In some embodiments, peptide tags with reduced or diminished binding affinity for the insulin receptor suitable for the invention include peptide tags having a binding affinity for the insulin receptor that is more than 1.5-fold, 2-fold, 3-fold, 4-fold, 5-fold, 6-fold, 7-fold, 8-fold, 9-fold, 10-fold, 12-fold, 14-fold, 16-fold, 18-fold, 20-fold, 50-fold, 100-fold less than that of the wild-type mature human IGF-II. The binding affinity for the insulin receptor can be measured using various in vitro and in vivo assays known in the art. Exemplary binding assays are described in the Examples section.

Mutagenesis

IGF-II muteins can be prepared by introducing appropriate nucleotide changes into the IGF-II DNA, or by synthesis of the desired IGF-II polypeptide. Variations in the IGF-II sequence can be made, for example, using any of the techniques and guidelines for conservative and non-conservative mutations set forth, for instance, in U.S. Pat. No. 5,364,934. Variations may be a substitution, deletion or insertion of one or more codons encoding IGF-II that results in a change in the amino acid sequence of IGF-II as compared with a naturally-occurring sequence of mature human IGF-II. Amino acid substitutions can be the result of replacing one amino acid with another amino acid having similar structural and/or chemical properties, such as the replacement of a leucine with a serine, i.e., conservative amino acid replacements. Amino acid substitutions can also be the result of replacing one amino acid with another amino acid having dissimilar structural and/or chemical properties, i.e., non-conservative amino acid replacements. Insertions or deletions may optionally be in the range of 1 to 5 amino acids. The variation allowed may be determined by systematically making insertions, deletions or substitutions of amino acids in the sequence and testing the resulting variants for activity in the in vivo or in vitro assays known in the art (such as binding assays to the CI-MPR or furin cleavage assays).

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions [Creighton, The Proteins, (W. H. Freeman & Co., N.Y.); Chothia, *J. Mol. Biol.,* 150:1 (1976)]. If alanine substitution does not yield adequate amounts of variant, an isoteric amino acid can be used.

The variations can be made using methods known in the art such as oligonucleotide-mediated (site-directed) mutagenesis, alanine scanning, and PCR mutagenesis. Site-directed mutagenesis [Carter et al., *Nucl. Acids Res.,* 13:4331 (1986); Zoller et al., *Nucl. Acids Res.,* 10:6487 (1987)], cassette mutagenesis [Wells et al., *Gene,* 34:315 (1985)], restriction selection mutagenesis [Wells et al., *Philos. Trans. R. Soc.* London SerA, 317:415 (1986)] or other known techniques can be performed on the cloned DNA to produce IGF-II muteins.

Spacer

A furin-resistant GILT tag can be fused to the N-terminus or C-terminus of a polypeptide encoding a lysosomal enzyme. The GILT tag can be fused directly to the lysosomal enzyme polypeptide or can be separated from the lysosomal enzyme polypeptide by a linker or a spacer. An amino acid linker or spacer is generally designed to be flexible or to interpose a structure, such as an alpha-helix, between the two protein moieties. A linker or spacer can be relatively short, such as the sequence Gly-Ala-Pro (SEQ ID NO: 4) or Gly-Gly-Gly-Gly-Gly-Pro (SEQ ID NO: 5), or can be longer, such as, for example, 10-25 amino acids in length. The site of a fusion junction should be selected with care to promote proper folding and activity of both fusion partners and to prevent premature separation of a peptide tag from a GAA polypeptide. In a preferred embodiment, the linker sequence is Gly-Ala-Pro (SEQ ID NO: 4).

Additional constructs of GILT-tagged GAA proteins that can be used in the methods and compositions of the present invention were described in detail in U.S. Publication No. 20050244400, the entire disclosure of which is incorporated herein by reference.

Cells

Any mammalian cell or cell type susceptible to cell culture, and to expression of polypeptides, may be utilized in accordance with the present invention, such as, for example, human embryonic kidney (HEK) 293, Chinese hamster ovary (CHO), monkey kidney (COS), HT1080, C10, HeLa, baby hamster kidney (BHK), 3T3, C127, CV-1, HaK, NS/0, and L-929 cells. Non-limiting examples of mammalian cells that may be used in accordance with the present invention include, but are not limited to, BALB/c mouse myeloma line (NSO/1, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells +/−DHFR (CHO, Urlaub and Chasin, Proc. Natl. Acad. Sci. USA, 77:4216 (1980)); mouse sertoli cells (TM4, Mather, Biol. Reprod., 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.*, 383:44-68 (1982)); MRC 5 cells; FS4 cells; and a human hepatoma line (Hep G2). In some embodiments, the fusion protein of the present invention is produced from CHO cell lines.

The fusion protein of the invention can also be expressed in a variety of non-mammalian host cells such as, for example, insect (e.g., Sf-9, Sf-21, Hi5), plant (e.g., *Leguminosa*, cereal, or tobacco), yeast (e.g., *S. cerivisae, P. pastoris*), prokaryote (e.g., *E. Coli, B. subtilis* and other *Bacillus* spp., *Pseudomonas* spp., *Streptomyces* spp), or fungus.

In some embodiments, a fusion protein with or without a furin-resistant GILT tag can be produced in furin-deficient cells. As used herein, the term "furin-deficient cells" refers to any cells whose furin protease activity is inhibited, reduced or eliminated. Furin-deficient cells include both mammalian and non-mammalian cells that do not produce furin or produce reduced amount or defective furin protease. Exemplary furin deficient cells that are known and available to the skilled artisan, including but not limited to FD11 cells (Gordon et al (1997) Infection and Immunity 65(8):3370 3375), and those mutant cells described in Moebring and Moehring (1983) Infection and Immunity 41(3):998 1009. Alternatively, a furin deficient cell may be obtained by exposing the above-described mammalian and non-mammalian cells to mutagenesis treatment, e.g., irradiation, ethidium bromide, bromidated uridine (BrdU) and others, preferably chemical mutagenesis, and more preferred ethyl methane sulfonate mutagenesis, recovering the cells which survive the treatment and selecting for those cells which are found to be resistant to the toxicity of *Pseudomonas* exotoxin A (see Moehring and Moehrin (1983) Infection and Immunity 41(3):998 1009).

Underglycosylation

Targeted therapeutic proteins of the invention can be underglycosylated, that is, one or more carbohydrate structures that would normally be present on a naturally-occurring human protein is preferably omitted, removed, modified, or masked. Without wishing to be bound by any theories, it is contemplated that an underglycosylated protein may extend the half-life of the protein in a mammal. Underglycosylation can be achieved in many ways. In some embodiments, the targeted fusion protein of the invention can be produced using a secretory signal peptide to facilitate secretion of the fusion protein. For example, the fusion protein can be produced using an IGF-II signal peptide. In general, the fusion protein produced using an IGF-II signal peptide has reduced mannose-6-phosphate (M6P) level on the surface of the protein compared to wild-type enzyme. In some embodiments, a protein may be completely underglycosylated (as when synthesized in *E. coli*), partially unglycosylated (as when synthesized in a mammalian system after disruption of one or more glycosylation sites by site-directed mutagenesis), or may have a non-mammalian glycosylation pattern. For example, underglycosylated fusion proteins may be generated by modifying, substituting or eliminating one or more glycosylation sites by site-directed mutagenesis. For example, wild-type GAA typically have seven sites that match the canonical recognition sequence for N-linked glycosylation, Asn-Xaa-Thr/Ser (SEQ ID NO: 7) (Xaa can be any residue except Pro), namely, Asn-140, -233, -390, -470, -652, -882 and -925 (Hoefsloot et al., 1988; Martiniuk et al., 1990b). One or more Asn at the above described positions may be changed or eliminated to generated underglycosylated GAA. In some embodiments, Asn may be changed to Gln.

In some embodiments, a therapeutic fusion protein can be deglycosylated after synthesis. For example, deglycosylation can be through chemical or enzymatic treatments, and may lead to complete deglycosylation or, if only a portion of the carbohydrate structure is removed, partial deglycosylation.

In some embodiments, glycosylation of a lysosomal enzyme is modified, e.g., by oxidation and reduction, to reduce clearance of the therapeutic protein from the blood. For example, a lysosomal enzyme can be deglycosylated by periodate treatment. In particular, treatment with periodate and a reducing agent such as sodium borohydride is effective to modify the carbohydrate structure of most glycoproteins. Periodate treatment oxidizes vicinal diols, cleaving the carbon-carbon bond and replacing the hydroxyl groups with aldehyde groups; borohydride reduces the aldehydes to hydroxyls. For example, at 1 mM concentration, periodate exclusively oxidizes sialic acid groups and at or above 10 mM all available vicinal diols are converted to aldehydes (Herrnanson, G. T. 1996, Bioconjugate techniques. Academic press). Once formed, aldehyde groups are highly reactive and may form Schiff's base linkages with primary amino groups in the protein resulting intramolecular linkages. Therefore, aldehyde groups formed ought to be reduced to alcohol groups. A commonly used reducing agent is $NaBH_4$ and the reaction is best run under alkaline conditions. Many sugar residues including vicinal diols, therefore, are cleaved by this treatment. Nevertheless, while this treatment converts cyclic carbohydrates into linear carbohydrates, it does not completely remove the carbohydrate, minimizing risks of exposing potentially protease-sensitive or antigenic polypeptide sites.

Grubb, J. H., et al (Grubb et al, 2008, *PNAS* 105:26(6) report treatment of human 8-glucuronidase with sodium metaperiodate followed by sodium borohydride reduction. The modified beta-glucuronidase retained 90% of activity, but lost both mannose and mannose-6-phosphate dependent receptor uptake activity. The alkaline pH condition used in the reduction due to sodium borohydride reagent as described by Grubb et al is not suitable for all lysosomal enzymes, many of which are labile under alkaline conditions.

Therefore, in some embodiments, sodium cyanoborohydride is used as reducing agent. While the rate of reduction of aldehydes by cyanoborohydride is negligible at neutral pH and above, the rate of reaction becomes rapid at acidic pH (Borch, et al. 1971, *JACS* 93:2897). For example, regimens using sodium metaperiodate and cyanoborohydride at pH 3.5-4 can be used.

For example, treatment of GAA or alpha galactosidase A, the enzymes deficient in Pompe and Fabry diseases respectively, with periodate and cyanoborohydride at pH 5.6 resulted in good recovery of enzyme activity. Enzyme was incubated with equal volume mixture containing 20 mM sodium metaperiodate and 40 mM sodium cyanoborohydride in 0.1 M Na acetate, pH 5.6 for 60 min on ice. The unreacted periodate was quenched with glycerol (10% final concentration) for 15 min on ice. The proteins were finally exchanged into phosphate buffered saline, pH 6.2 by diafiltration using Amicon centrifugal filter devices. Other reducing reagents for example, dimethylamine borane, may also be useful to reduce aldehydes generated by sodium metaperiodate oxidation of glycoproteins such as GAA under acidic conditions.

Thus, in some embodiments, the reduction of sodium metaperiodate treated GAA involves use of sodium cyanoborohydride at acidic pH from pH 3.0 to pH 6. Optimal conditions for the chemical modification can be readily determined by using two assays: loss of binding to ConA sepharose, and diminished uptake into J774E macrophage.

For example, the ability of periodate/borohydride modified β-glucuronidase to bind to ConA-sepharose was compared to that of untreated β-glucuronidase. The enzymes were incubated with 50 μl ConA beads in 20 mM Tris-HCl, pH 6.8, 0.5 M NaCl for 15 min at room temperature. Beads were centrifuged at maximum speed for 15 sec. Supernatant (flow through) was carefully withdrawn, assayed for GUS activity and analyzed by SDS/PAGE. When we treated GUS exactly as reported in Grubb et al., 60% ConA binding activity was lost and unbound GUS was present only in the flow through of periodate treated and subsequently sodium borohydride reduced sample.

Administration of Therapeutic Proteins

In accordance of the invention, a therapeutic protein of the invention is typically administered to the individual alone, or in compositions or medicaments comprising the therapeutic protein (e.g., in the manufacture of a medicament for the treatment of the disease), as described herein. The compositions can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like) which do not deleteriously react with the active compounds or interference with their activity. In a preferred embodiment, a water-soluble carrier suitable for intravenous administration is used.

The composition or medicament, if desired, can also contain minor amounts of wetting or emulsifying agents, or pH buffering agents. The composition can be a liquid solution, suspension, emulsion, tablet, pill, capsule, sustained release formulation, or powder. The composition can also be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

The composition or medicament can be formulated in accordance with the routine procedures as a pharmaceutical composition adapted for administration to human beings. For example, in a preferred embodiment, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

The therapeutic protein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

A therapeutic protein (or a composition or medicament containing a therapeutic protein) is administered by any appropriate route. In a preferred embodiment, a therapeutic protein is administered intravenously. In other embodiments, a therapeutic protein is administered by direct administration to a target tissue, such as heart or muscle (e.g., intramuscular), or nervous system (e.g., direct injection into the brain; intraventricularly; intrathecally). Alternatively, a therapeutic protein (or a composition or medicament containing a therapeutic protein) can be administered parenterally, transdermally, or transmucosally (e.g., orally or nasally). More than one route can be used concurrently, if desired.

A therapeutic protein (or a composition or medicament containing a therapeutic protein) can be administered alone, or in conjunction with other agents, such as antihistamines (e.g., diphenhydramine) or immunosuppressants or other immunotherapeutic agents which counteract anti-GILT-tagged lysosomal enzyme antibodies. The term, "in conjunction with," indicates that the agent is administered prior to, at about the same time as, or following the therapeutic protein (or a composition or medicament containing the therapeutic protein). For example, the agent can be mixed into a composition containing the therapeutic protein, and thereby administered contemporaneously with the therapeutic protein; alternatively, the agent can be administered contemporaneously, without mixing (e.g., by "piggybacking" delivery of the agent on the intravenous line by which the therapeutic protein is also administered, or vice versa). In another example, the agent can be administered separately (e.g., not admixed), but within a short time frame (e.g., within 24 hours) of administration of the therapeutic protein.

The therapeutic protein (or composition or medicament containing the therapeutic protein) is administered in a therapeutically effective amount (i.e., a dosage amount that, when administered at regular intervals, is sufficient to treat the disease, such as by ameliorating symptoms associated with the disease, preventing or delaying the onset of the disease, and/or also lessening the severity or frequency of symptoms of the disease, as described above). The dose which will be therapeutically effective for the treatment of the disease will depend on the nature and extent of the disease's effects, and can be determined by standard clinical techniques. In addition, in vitro or in vivo assays may optionally be employed to help identify optimal dosage ranges using methods known in the art. The precise dose to be employed will also depend on the route of administration, and the seriousness of the disease, and should be decided according to the judgment of a practitioner and each patient's circumstances. Effective doses may be extrapolated from dose-response curves derived from in vitro or animal model test systems. The therapeutically effective dosage amount can be, for example, about 0.1-1 mg/kg, about 1-5 g/kg, about 5-20 mg/kg, about 20-50 mg/kg, or 20-100 mg/kg. The effective dose for a particular individual can be varied (e.g., increased or decreased) over time, depending on the needs of the individual. For example, in times of physical illness or stress, or if disease symptoms worsen, the dosage amount can be increased.

The therapeutically effective amount of the therapeutic protein (or composition or medicament containing the therapeutic protein) is administered at regular intervals, depending on the nature and extent of the disease's effects, and on an ongoing basis. Administration at an "interval," as used herein, indicates that the therapeutically effective amount is administered periodically (as distinguished from a one-time dose). The interval can be determined by standard clinical techniques. In some embodiments, the therapeutic protein is administered bimonthly, monthly, twice monthly, triweekly, biweekly, weekly, twice weekly, thrice weekly, or daily. The administration interval for a single individual need not be a fixed interval, but can be varied over time, depending on the needs of the individual. For example, in times of physical illness or stress, or if disease symptoms worsen, the interval between doses can be decreased.

As used herein, the term "bimonthly" means administration once per two months (i.e., once every two months); the term "monthly" means administration once per month; the term "triweekly" means administration once per three weeks (i.e., once every three weeks); the term "biweekly" means administration once per two weeks (i.e., once every two weeks); the term "weekly" means administration once per week; and the term "daily" means administration once per day.

The invention additionally pertains to a pharmaceutical composition comprising a therapeutic protein, as described herein, in a container (e.g., a vial, bottle, bag for intravenous administration, syringe, etc.) with a label containing instructions for administration of the composition for treatment of Pompe disease, such as by the methods described herein.

The invention will be further and more specifically described by the following examples. Examples, however, are included for illustration purposes, not for limitation.

EXAMPLES

Example 1

Furin Cleaves an IGF-II Based GILT Tag

ZC-701 has been developed for the treatment of Pompe disease. ZC-701 is a chimeric protein that contains an N-terminal IGF-II based GILT tag fused via a three amino acid spacer to residues 70-952 of human acid-α-glucosidase (hGAA). Specifically, ZC-701 includes amino acids 1 and 8-67 of human IGF-II (i.e., Δ2-7 of mature human IGF-II), the spacer sequence Gly-Ala-Pro, and amino acids 70-952 of human GAA. The full length amino acid sequence is shown below. The spacer sequence is bolded. The sequence N-terminal to the spacer sequence reflects amino acids 1 and 8-67 of human IGF-II and the sequence C-terminal to the spacer sequence reflects amino acids 70-952 of human GAA. The two potential overlapping furin cleavage sites within the IGF-II tag sequence is bolded and underlined. Arrows point to two potential furin cleavage positions.

(SEQ ID NO: 8)

↓ ↓

AALCGGELVDTLQFVCGDRGFYFSRPASRVSRRSRGIVEECCFRSCDLAL

LETYCATPAKSEGAPAHPGRPRAVPTQCDVPPNSRFDCAPDKAITQEQCE

ARGCCYIPAKQGLQGAQMGQPWCFFPPSYPSYKLENLSSSEMGYTATLTR

TTPTFFPKDILTLRLDVMMETENRLHFTIKDPANRRYEVPLETPRVHSRA

PSPLYSVEFSEEPFGVIVHRQLDGRVLLNTTVAPLFFADQFLQLSTSLPS

QYITGLAEHLSPLMLSTSWTRITLWNRDLAPTPGANLYGSHPFYLALEDG

GSAHGVFLLNSNAMDVVLQPSPALSWRSTGGILDVYIFLGPEPKSVVQQY

LDVVGYPFMPPYWGLGFHLCRWGYSSTAITRQVVENMTRAHFPLDVQWND

LDYMDSRRDFTFNKDGFRDEPAMVQELHQGGRRYMMIVDPAISSSGPAGS

YRPYDEGLRRGVFITNETGQPLIGKVWPGSTAFPDFTNPTALAWWEDMVA

EFHDQVPFDGMWIDMNEPSNFIRGSEDGCPNNELENPPYVPGVVGGTLQA

ATICASSHQFLSTHYNLHNLYGLTEAIASHRALVKARGTRPFVISRSTFA

GHGRYAGHWTGDVWSSWEQLASSVPEILQFNLLGVPLVGADVCGFLGNTS

EELCVRWTQLGAFYPFMRNHNSLLSLPQEPYSFSEPAQQAMRKALTLRYA

LLPHLYTLFHQAHVAGETVARPLFLEFPKDSSTWTVDHQLLWGEALLITP

VLQAGKAEVTGYFPLGTWYDLQTVPIEALGSLPPPPAAPREPAIHSEGQW

VTLPAPLDTINVHLRAGYIIPLQGPGLTTTESRQQPMALAVALTKGGEAR

GELFWDDGESLEVLERGAYTQVIFLARNNTIVNELVRVTSEGAGLQLQKV

TVLGVATAPQQVLSNGVPVSNFTYSPDTKVLDICVSLLMGEQFLVSWC

During the course of development of ZC-701, it has become apparent that the IGF-II derived GILT tag on a fraction of the ZC-701 molecules is subjected to proteolytic cleavage by furin during production in CHO cells. N-terminal analysis of ZC-701 batch 10-2-F45-54 revealed the presence of two n-terminal sequences. One conformed to the predicted n-terminus of ZC-701 indicating the presence of the predicted ZC-701 protein. The other n-terminal sequence aligned with sequence within the tag portion of ZC-701 indicating the presence of a derivative of ZC-701 consistent with an endoproteolytic cleavage at amino acid residue 34 of ZC-701. Based on the estimated molar ratios of the two n-termini, this batch of ZC-701 was found to have about a 1:1 ratio of intact and cleaved species.

Upon receipt of this result, each of the other batches of ZC-701 were subjected to n-terminal sequencing. All of the batches displayed the same two n-termini with the cleaved species ranging from 20-50% of the total compound. One batch, previously shown to have low uptake activity, displayed a set of n-termini indicative of additional proteolysis. We concluded that the proteolytic event responsible for the second species in all of our batches of ZC-70I was perpetrated by furin or a furin-like protease.

Figure 1:
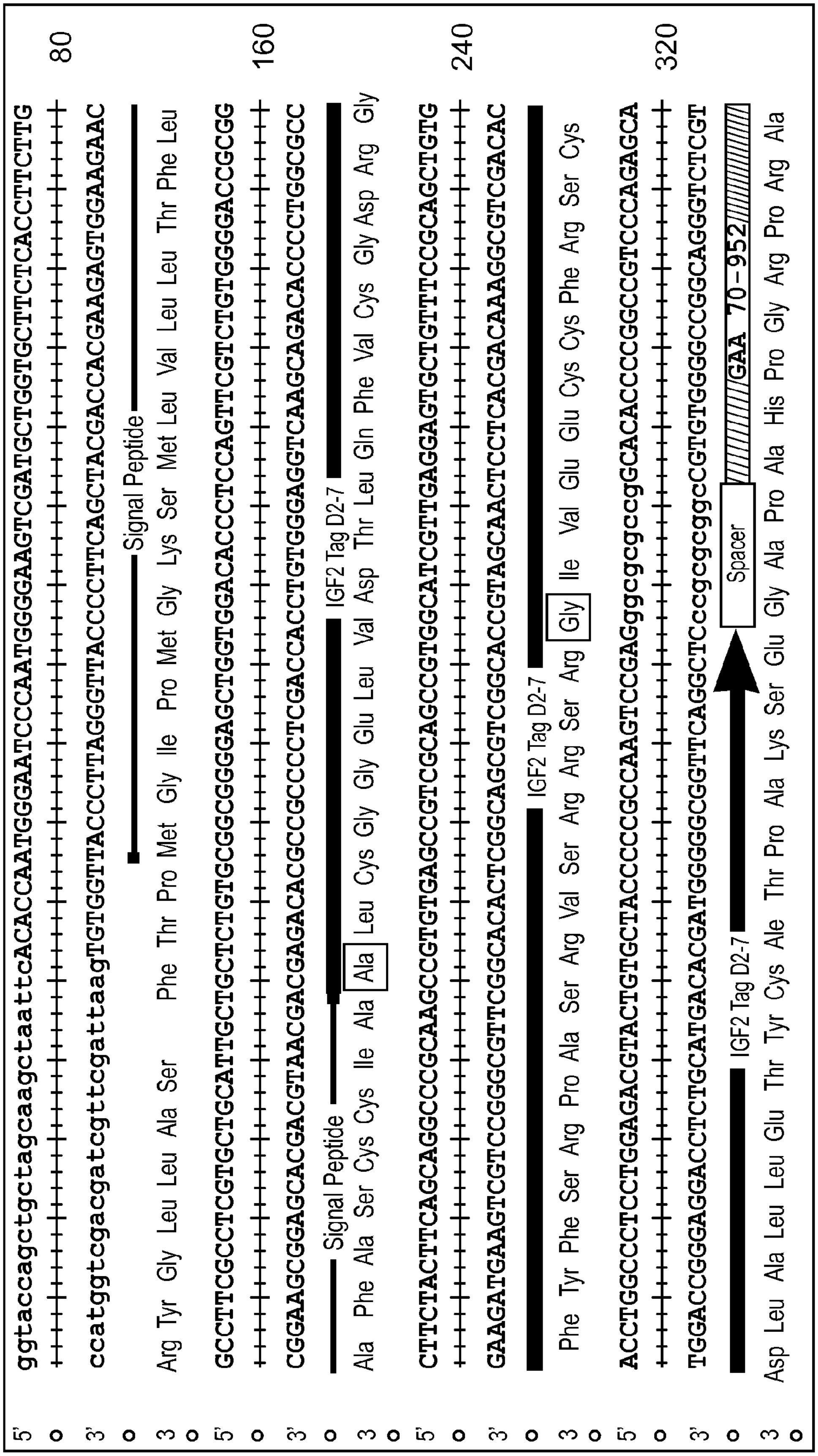

FIG. 1 shows a map of the amino terminus of ZC-701. The two amino acid boxed residues are the sites of n-termini mapped in all of the ZC-701 batches. The first of the N-termini is the site of signal peptide cleavage, which yields the predicted n-terminus of ZC-701. The second boxed residue is the site of an undesired proteolytic cleavage event. The amino acid sequence proximal to the cleavage site is Arg-Arg-Ser-Arg (SEQ ID NO: 9). This matches the canonical cleavage site of a protease present in CHO cells called furin, which cleaves after Arg-X-X-Arg (SEQ ID NO: 10). Furin is a member of a family of prohormone convertases that includes PC3, a protease responsible for maturation of proinsulin in pancreatic islet cells. In fact the PC3 cleavage site in proinsulin is conserved and identical to the site at which furin cleaves the IGF-II tag.

The Furin cleaved ZC-701 differs in molecular weight from intact ZC-701 by about 3000 daltons, which represents less than a 3% difference in molecular weight. Due to the heterogeneity of the oligosaccharide in the protein, the presence of the cleaved ZC-701 was not previously detected by SDS-PAGE. However, if ZC-701 is first deglycosylated by treatment with Peptide N-Glycosidase F (PNGase F), then the cleaved protein can be resolved from the intact ZC-701 by SDS-PAGE.

Figure 2:
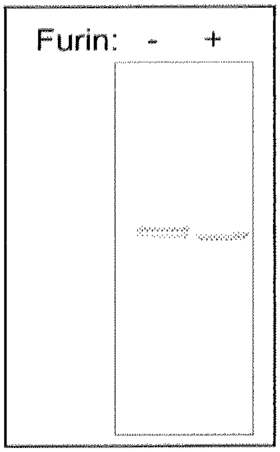

As shown in FIG. 2, lane 1 of the SDS-PAGE gel shows the electrophoretic pattern of deglycosylated purified ZC-701. Two bands are evident. The upper band is believed to be intact ZC-701 and the lower band is believed to be furin cleaved ZC-701. To prove that the lower band is indeed Furin cleaved ZC-701, same proteins loaded in lane I were first treated with furin and then loaded in lane 2. As shown in FIG. 2, all of the proteins in lane 2 co-migrates with the lower band in lane 1 indicating that the lower band is in fact furin cleaved ZC-701.

We have estimated the proportion of ZC-701 that has been cleaved with furin in a number of batches of ZC-701 by quantification of the band intensity in SDS-PAGE and by quantification of amino acids released in N-terminal sequencing experiments. As discussed above, the fraction of cleaved ZC-701 has ranged from 20% to 50% in different batches.

Example 2

Targeted Fusion Proteins Containing a Furin-Resistant IGF-II Based GILT Tag

We can design around the problem of furin cleavage by altering the amino acid sequence IGF-II such that the amino acid alteration abolishes at least one furin cleavage site. A series of mutant versions of ZC-701 were generated and assayed for resistance to cleavage by furin. Exemplary mutant versions of ZC-701 were generated as described below.

ZC-701

The GILTΔ2-7-GAA70-952 cassette below was cloned using the Asp718 and NotI sites of the cassette and vector pCEP4 to produce pCEP-GILTΔ2-7-GAA70-952 (Plasmid p701). Restriction sites for cloning are in lowercase bold. The spacer amino acid sequence Gly, Ala, Pro (underlined sequence) separate the GAA gene and GILTΔ2-7 tag (upper case sequence). The spacer and tag are placed upstream of GAA residue Ala70.

(SEQ ID NO: 11)

ggtaccagctgctagcaagctaattcacaccaATGGGAATCCCAATGGGG

AAGTCGATGCTGGTGCTTCTCACCTTCTTGGCCTTCGCCTCGTGCTGCAT

TGCTGCTCTGTGCGGCGGGGAGCTGGTGGACACCCTCCAGTTCGTCTGTG

GGGACCGCGGCTTCTACTTCAGCAGGCCCGCAAGCCGTGTGAGCCGTCGC

AGCCGTGGCATCGTTGAGGAGTGCTGTTTCCGCAGCTGTGACCTGGCCCT

CCTGGAGACGTACTGTGCTACCCCCGCCAAGTCCGAGGGCGCGCCGgcac accccggccgtcccagagcagtgcccacacagtgcgacgtcccccccaac agccgcttcgattgcgcccctgacaaggccatcacccaggaacagtgcga ggcccgcggctgctgctacatccctgcaaagcaggggctgcagggagccc agatggggcagccctggtgcttcttcccacccagctaccccagctacaag ctggagaacctgagctcctctgaaatgggctacacggccaccctgacccg taccacccccaccttcttccccaaggacatcctgaccctgcggctggacg tgatgatggagactgagaaccgcctccacttcacgatcaaagatccagct aacaggcgctacgaggtgcccttggagaccccgcgtgtccacagccgggc accgtecccactctacagcgtggagttctctgaggagcccttcggggtga tcgtgcaccggcagctggacggccgcgtgctgctgaacacgacggtggcg cccctgttctttgcggaccagttecttcagctgtccacctcgctgccctc gcagtatatcacaggcctcgccgagcacctcagtcccctgatgctcagca ccagctggaccaggatcaccctgtggaaccgggaccttgcgcccacgccc ggtgcgaacctctacgggtctcaccctttctacctggcgctggaggacgg cgggtcggcacacggggtgttcctgctaaacagcaatgccatggatgtgg tcctgcagccgagccctgcccttagctggaggtcgacaggtgggatcctg gatgtctacatcttcctgggcccagagcccaagagcgtggtgcagcagta cctggacgttgtgggatacccgttcatgccgccatactggggcctgggct tccacctgtgccgctggggctactcctccaccgctatcacccgccaggtg gtggagaacatgaccagggcccacttcccccctggacgtccaatggaacga cctggactacatggactcccggagggacttcacgttcaacaaggatggct tccgggacttcccggccatggtgcaggagctgcaccagggcggccggcgc tacatgatgatcgtggatcctgccatcagcagctcgggccctgccgggag ctacaggccctacgacgagggtctgcggagggggttttcatcaccaacg agaccggccagccgctgattgggaaggtatggcccgggtccactgccttc cccgacttcaccaaccccacagccctggcctggtgggaggacatggtggc tgagttccatgaccaggtgcccttcgacggcatgtggattgacatgaacg -continued agccttccaacttcatcaggggctctgaggacggctgccccaacaatgag ctggagaacccaccctacgtgcctggggtggttgggggaccctccaggc ggcaaccatctgtgcctccagccaccagatctctccacacactacaacct gcacaacctctacggcctgaccgaagccatcgcctcccacagggcgctgg tgaaggctcgggggacacgcccatttgtgatctcccgctcgacctagctg gccacggccgatacgccggccactggacgggggacgtgtggagctcctgg gagcagctcgcctcctccgtgccagaaatcctgcagtttaacctgctggg ggtgcctctggtcggggccgacgtctgcggatcctgggcaacacctcaga ggagctgtgtgtgcgctggacccagctgggggccactaccccttcatgcg gaaccacaacagcctgctcagtctgccccaggagccgtacagcttcagcg agccggcccagcaggccatgaggaaggccctcaccctgcgctacgcactc ctcccccacctctacacgctgttccaccaggcccacgtcgcgggggagac cgtggcccggcccctcttcctggagttccccaaggactctagcacctgga ctgtggaccaccagctcctgtgggggggaggccctgctcatcaccccagtg ctccaggccgggaaggccgaagtgactggctacttccccttgggcacatg gtacgacctgcagacggtgccaatagaggcccttggcagcctcccacccc cacctgcagctccccgtgagccagccatccacagcgaggggcagtgggtg acgctgccggccccccctggacaccatcaacgtccacctccgggctgggta catcatcccccctgcagggccctggcctcacaaccacagagtcccgccagc agcccatggccctggctgtggccctgaccaagggtggagaggcccgaggg gagctgttctgggacgatggagagagcctggaagtgctggagcgaggggc ctacacacaggtcatcttcctggccaggaataacacgatcgtgaatgagc tggtacgtgtgaccagtgagggagctggcctgcagctgcagaaggtgact gtcctgggcgtggccacggcgccccagcaggtcctctccaacggtgtccc tgtctccaacttcacctacagccccgacaccaaggtcctggacatctgtg tctcgctgttgatgggagagcagtttctcgtcagctggtgttagtctaga gcttgctagcggccgc

Construct 1459

The GILTΔ2-7/K37-GAA70-952 cassette below was cloned using the Asp718 and NotI sites of the cassette and vector pCEP4 to produce pCEP-GILTΔ2-7/K37-GAA70-952 (Plasmid p1459). Restriction sites for cloning are in lowercase bold. The spacer amino acid sequence Gly, Ala, Pro (underlined sequence) separate the GAA gene and GILTΔ2-7/K37 tag (upper case sequence). The spacer and tag are placed upstream of GAA residue Ala70. The GILTΔ2-7/K37 cassette contains an Arg to Lys substitution at amino acid 37 of the human IGF-II sequence (uppercase bold).

(SEQ ID NO: 12)

ggtaccagctgctagcaagctaattcacaccaATGGGAATCCCAATGGGG

AAGTCGATGCTGGTGCTTCTCACTTCTTGGCCTTCGCCTCGTGCTGCATT

GCTGCTCTGTGCGGCGGGGAGCTGGTGGACACCCTCCAGTTCGTCTGTGG

GGACCGCGGCTTCTACTTCAGCAGGCCCCGCAAGCCGTGTGAGCAAGCGC

AGCCGTGGCATCGTTGAGGAGTGCTGTTTCCGCAGCTGTGACCTGGCCCT

-continued

CCTGGAGACGTACTGTGCTACCCCCGCCAAGTCCGAGGGCGCGCCGgcac accccggccgtcccagagcagtgcccacacagtgcgacgtcccccccaac agccgcttcgattgcgcccctgacaaggccatcacccaggaacagtgcga ggcccgcggctgctgctacatccctgcaaagcaggggctgcagggagccc agatggggcagccctggtgcttcttcccacccagctaccccagctacaag ctggagaacctgagctcctctgaaatgggctacacggccaccctgacccg taccacccccaccttcttccccaaggacatcctgaccctgcggctggacg tgatgatggagactgagaaccgcctccacttcacgatcaaagatccagct aacaggcgctacgaggtgcccttggagaccccgcgtgtccacagccgggc accgtccccactctacagcgtggagttctctgaggagcccttcggggtga tcgtgcaccggcagctggacggccgcgtgctgctgaacacgacggtggcg cccctgttctttgcggaccagttccttcagctgtccacctcgctgccctc gcagtatatcacaggcctcgccgagcacctcagtcccctgatgctcagca ccagctggaccaggatcaccctgtggaaccgggaccttgcgcccacgccc ggtgcgaacctctacgggtctcaccctttctacctggcgctggaggacgg cgggtcggcacacggggtgttcctgctaaacagcaatgccatggatgtgg tcctgcagccgagccctgcccttagctggaggtcgacaggtgggatcctg gatgtctacatcttcctgggcccagagcccaagagcgtggtgcagcagta cctggacgttgtgggatacccgttcatgccgccatactggggcctgggct tccacctgtgccgctggggctactcctccaccgctatcacccgccaggtg gtggagaacatgaccagggcccacttcccccctggacgtccaatggaacga cctggactacatggactcccggagggacttcacgttcaacaaggatggct tccgggacttcccggccatggtgcaggagctgcaccagggcggccggcgc tacatgatgatcgtggatcctgccatcagcagctcgggccctgccgggag ctacaggccctacgacgagggtctgcggaggggggttttcatcaccaacg agaccggccagccgctgattgggaaggtatggcccgggtccactgccttc cccgacttcaccaaccccacagccctggcctggtgggaggacatggtggc tgagttccatgaccaggtgcccttcgacggcatgtggattgacatgaacg agccttccaacttcatcaggggctctgaggacggctgccccaacaatgag ctggagaacccaccctacgtgcctggggtggttgggggaccctccaggc ggcaaccatctgtgcctccagccaccagtttctctccacacactacaacc tgcacaacctctacggcctgaccgaagccatcgcctcccacagggcgctg gtgaaggctcgggggacacgcccatttgtgatctcccgctcgacctttgc tggccacggccgatacgccggccactggacgggggacgtgtggagctcct gggagcagctcgcctcctccgtgccagaaatcctgcagtttaacctgctg gggtgcctctggtcggggccgacgtctgcggcttcctgggcaacacctc agaggagctgtgtgtgcgctggacccagctgggggccttctaccccttca tgcggaaccacaacagcctgctcagtctgccccaggagccgtacagcttc agcgagccggcccagcaggccatgaggaaggccctcaccctgcgctacgc actcctcccccacctctacacgctgttccaccaggcccacgtcgcggggg -continued

```
agaccgtggcccggcccctcttcctggagttccccaaggactctagcacc
tggactgtggaccaccagctcctgtgggggaggccctgctcatcacccc
agtgctccaggccgggaaggccgaagtgactggctacttccccttgggca
catggtacgacctgcagacggtgccaatagaggcccttggcagcctccca
cccccacctgcagctccccgtgagccagccatccacagcgaggggcagtg
ggtgacgctgccggccccctggacaccatcaacgtccacctccgggctg
ggtacatcatcccctgcagggccctggcctcacaactacagagtcccgc
cagcagcccatggccctggctgtggccctgaccaagggtggagaggcccg
aggggagctgttctgggacgatggagagagcctggaagtgctggagcgag
ggcctacacacaggtcatcttcctggccaggaataacacgatcgtgaat
gagctggtacgtgtgaccagtgagggagctggcctgcagctgcagaaggt
gactgtcctgggcgtggccacggcgccccaggcaggtcctctccaacggt
gtccctgtctccaacttcacctacagccccgacaccaaggtcctggacat
ctgtgtctcgctgttgatgggagagcagtttctcgtcagctggtgttagt
ctagagcttgctagcggccgc
```

Construct 1460

The GILTΔ2-7/K40-GAA70-952 cassette below was cloned using the Asp718 and NotI sites of the cassette and vector pCEP4 to produce pCEP-GILTΔ2-7/K40-GAA70-952 (Plasmid p1460). Restriction sites for cloning are in lowercase bold. The spacer amino acid sequence Gly, Ala, Pro (underlined sequence) separate the GAA gene and GILTΔ2-7/K40 tag (upper case sequence). The spacer and tag are placed upstream of GAA residue Ala70. The GILTΔ2-7/K40 cassette contains an Arg to Lys substitution at amino acid 40 of the human IGF-II sequence (uppercase bold).

(SEQ ID NO: 13)

```
ggtaccagctgctagcaagctaattcacaccaATGGGAATCCCAATGGGG
AAGTCGATGCTGGTGCTTCTCACCTTCTTGGCCTTCGCCTCGTGCTGCAT
TGCTGCTCTGTGCGGCGGGGAGCTGGTGGACACCCTCGAGTTCGTCTGTG
GGGACCGCGGCTTCTACTTCAGCAGGCCCGCAAGCCGTGTGAGCCGTCGC
AGCAAGGGCATCGTTGAGGAGTGCTGTTTCCGCAGCTGTGACCTGGCCCT
CCTGGAGACGTACTGTGCTACCCCCGCCAAGTCCGAGGGCGCGCCGgcac
accccggccgtcccagagcagtgcccacacagtgcgacgtccccccaac
agccgcttcgattgtgcccctgacaaggccatcacccaggaacagtgcga
ggcccgcggctgctgctacatccctgcaaagcaggggctgcagggagccc
agatggggcagccctggtgcttcttcccacccagctaccccagctacaag
ctggagaacctgagctcctctgaaatgggctacacggccaccctgacccg
taccacccccaccttcttccccaaggacatcctgaccctgcggctggacg
tgatgatggagactgagaaccgcctccacttcacgatcaaagatccagct
aacaggcgctacgaggtgcccttggagaccccgcgtgtccacagccgggc
accgtccccactctacagcgtggagttctctgaggagcccttcggggtgat
cgtgcaccggcagctggacggccgcgtgctgctgaacacgacggtggcgc
ccctgttctttgcggaccagttccttcagctgtccacctcgctgccctcg
```

-continued

```
cagtatatcacaggcctcgccgagcacctcagtcccctgatgctcagcac
cagctggaccaggatcaccctgtggaaccgggaccttgcgcccacgcccg
gtgcgaacctctacgggtctcaccctttctacctggcgctggaggacggc
gggtcggcacacggggtgttcctgctaaacagcaatgccatggatgtggt
cctgcagccgagccctgcccttagctggaggtcgacaggtgggatcctgg
atgtctacatcttcctgggcccagagcccaagagcgtggtgcagcagtac
ctggacgttgtgggatacccgttcatgccgccatactggggcctgggctt
ccacctgtgccgctggggctactcctccaccgctatcacccgccaggtgg
tggagaacatgaccagggcccacttccccctggacgtccaatggaacgac
ctggactacatggactcccggagggacttcacgttcaacaaggatggctt
ccgggacttcccggccatggtgcaggagctgcaccagggcggccggcgct
acatgatgatcgtggatcctgccatcagcagctcgggccctgccgggagc
tacaggccctacgacgagggtctgcggaggggggttttcatcaccaacga
gaccggccagccgctgattgggaaggtatggcccgggtccactgccttcc
ccgacttcaccaaccccacagccctggcctggtgggaggacatggtggct
gagttccatgaccaggtgcccttcgacggcatgtggattgacatgaacga
gccttccaacttctttcaggggctctgaggacggctgccccaacaatgagc
ttgagaacccaccctacgtgcctggggtggttggggggaccctccaggcg
gcaaccatctgtgcctccagccaccagtttctctccacacactacaacct
gcacaacctctacggcctgaccgaagccatcgcctcccacagggcgctgg
tgaaggctcgggggacacgcccatttgtgatctcccgctcgacctttgct
ggccacggccgatacgccggccactggacgggggacgtgtggagctcctg
ggagcagctcgcctcctccgtgccagaaatcctgcagtttaacctgctgg
gggtgcctctggtcggggccgacgtctgcggcttcctgggcaacacctca
gaggagctgtgtgtgcgctggacccagctgggggccttctaccccttcat
gcggaaccacaacagcctgctcagtctgccccaggagccgtacagcttca
gcgagccggcccagcaggccatgaggaaggccctcaccctgcgctacgca
ctcctcccccacctctacacgctgttccaccaggcccacgtcgcgggga
gaccgtggcccggcccctcttcctggagttccccaaggactctagcacct
ggactgtggaccaccagctcctgtgggggaggccctgctcatcacccca
gtgctccaggccgggaaggccgaagtgactggctacttccccttgggcac
atggtacgacctgcagacggtgccaatagaggcccttggcagcctcccac
ccccacctgcagctccccgtgagccagccatccacagcgaggggcagtgg
gtgacgctgccggccccctggacaccatcaacgtccacctccgggctgg
gtacatcatcccctgcagggccctggcctcacaaccacagagtcccgcc
agcagcccatggccctggctgtggccctgaccaagggtggagaggcccga
ggggagctgttctgggacgatggagagagcctggaagtgctggagcgagg
ggcctacacacaggtcatcttcctggccaggaataacacgatcgtgaatg
agctggtacgtgtgaccagtgagggagctggcctgcagctgcagaaggtg
actgtcctgggcgtggccacggcgccccagcaggtcctctccaacggtgt
ccctgtctccaacttcacctacagccccgacaccaaggtcctggacatct
```

-continued gtgtctcgctgttgatgggagagcagtttctcgtcagctggtgttagtct agagcttgctagcggccgc

Construct 1461

The GILTΔ2-7/A37-GAA70-952 cassette below was cloned using the Asp718 and NotI sites of the cassette and vector pCEP4 to produce pCEP-GILTΔ2-7/A37-GAA70-952 (Plasmid p1461). Restriction sites for cloning are in lowercase bold. The spacer amino acid sequence Gly, Ala, Pro (underlined sequence) separate the GAA gene and GILTΔ2-7/A37 tag (upper case sequence). The spacer and tag are placed upstream of GAA residue Ala70. The GILTΔ2-7/A37 cassette contains an Arg to Ala substitution at amino acid 37 of the human IGF-II sequence (uppercase bold).

(SEQ ID NO: 14)

ggtaccagctgctagcaagctaattcacaccaATGGGAATCCCAATGGGG

AAGTCGATGCTGGTGCTTCTCACCTTCTTGGCCTTCGCCTCGTGCTGCAT

TGCTGCTCTGTGCGGCGGGGAGCTGGTGGACACCCTCCAGTTCGTCTGTG

GGGACCGCGGCTTCTACTTCAGCAGGCCCGCAAGCCGTGTGAGCGCTCGC

AGCCGTGGCATCGTTGAGGAGTGCTGTTTCCGCAGCTGTGACCTGGCCCT

CCTGGAGACGTACTGTGCTACCCCCGCCAAGTCCGAG<u>GGCGCGCCG</u>gcac accccggccgtcccagagcagtgcccacacagtgcgacgtccccccaac agccgcttcgattgcgcccctgacaaggccatcacccaggaacagtgcga ggcccgcggctgctgctacatccctgcaaagcaggggctgcagggagccc agatggggcagccctggtgcttcttcccacccagctaccccagctacaag ctggagaacctgagctcctctgaaatgggctacacggccaccctgacccg taccacccccaccttcttccccaaggacatcctgaccctgcggctggacg tgatgatggagactgagaaccgcctccacttcacgatcaaagatccagct aacaggcgctacgaggtgcccttggagaccccgcgtgtccacagccgggc accgtccccactctacagcgtggagttctctgaggagcccttcggggtga tcgtgcaccggcagctggacggccgcgtgctgctgaacacgacggtggcg cccctgttctttgcggaccagttccttcagctgtccacctcgctgccctc gcagtatatcacaggcctcgccgagcacctcagtcccctgatgctcagca ccagctggaccaggatcaccctgtggaaccgggaccttgcgcccacgccc ggtgcgaacctctacgggtctcaccctttctacctggcgctggaggacgg cgggtcggcacacggggtgttcctgctaaacagcaatgccatggatgtgg tcctgcagccgagccctgcccttagctggaggtcgacaggtgggatcctg gatgtctacatcttcctgggcccagagcccaagagcgtggtgcagcagta cctggacgttgtgggatacccgttcatgccgccatactggggcctgggct tccacctgtgccgctggggctactcctccaccgctatcacccgccaggtg gtggagaacatgaccagggcccacttccccctggacgtccaatggaacga cctggactacatggactcccggagggacttcacgttcaacaaggatggct tccgggacttcccggccatggtgcaggagctgcaccagggcggccggcgc tacatgatgatcgtggatcctgccatcagcagctcgggccctgccgggag ctacaggcctacgacgagggtctgcggagggggttttcatcaccaacga -continued gaccggccagccgctgattgggaaggtatggcccgggtccactgccttcc ccgacttcaccaaccccacagccctggcctggtgggaggacatggtggct gagttccatgaccaggtgcccttcgacggcatgtggattgacatgaacga gccttccaacttcatcaggggctctgaggacggctgccccaacaatgagc tggagaacccaccctacgtgcctggggtggttgggggggaccctccaggcg gcaaccatctgtgcctccagccaccagtttctctccacacactacaacct gcacaacctctacggcctgaccgaagccatcgcctcccacagggcgctgg tgaaggctcgggggacacgcccatttgtgatctcccgctcgacctttgct ggccacggccgatacgccggccactggacgggggacgtgtggagctcctg ggagcagctcgcctcctccgtgccagaaatcctgcagtttaacctgctgg gggtgcctctggtcggggccgacgtctgcggcttcctgggcaacacctca gaggagctgtgtgtgcgctggacccagctgggggccttctaccccttcat gcggaaccacaacagcctgctcagtctgccccaggagccgtacagcttca gcgagccggcccagcaggccatgaggaaggccctcaccctgcgctacgca ctcctcccccacctctacacgctgttccaccaggcccacgtcgcggggga gaccgtggcccggcccctcttcctggagttccccaaggactctagcacct ggactgtggaccaccagctcctgtgggggggaggccctgctcatcacccca gtgctccaggccgggaaggccgaagtgactggctacttccccttgggcac atggtacgacctgcagacggtgccaatagaggcccttggcagcctcccac cccccacctgcagctccccgtgagccagccatccacagcgagggggcagtgg gtgacgctgccggcccccctggacaccatcaacgtccacctccgggctgg gtacatcatccccctgcagggccctggcctcacaaccacagagtcccgcc agcagcccatggccctggctgtggccctgaccaagggtggagaggcccga ggggagctgttctgggacgatggagagagcctggaagtgctggagcgagg ggcctacacacaggtcatcttcctggccaggaataacacgatcgtgaatg agctggtacgtgtgaccagtgagggagctggcctgcagctgcagaaggtg actgtcctgggcgtggccacggcgccccagcaggtcctctccaacggtgt ccctgtctccaacttcacctacagccccgacaccaaggtcctggacatct gtgtctcgctgttgatgggagagcagtttctcgtcagctggtgttagtct agagcttgctagcggccgc

Construct 1463

The GILTΔ2-7/A40-GAA70-952 cassette below was cloned using the Asp718 and NotI sites of the cassette and vector pCEP4 to produce pCEP-GILTΔ2-7/A40-GAA70-952 (Plasmid p1463). Restriction sites for cloning are in lowercase bold. The spacer amino acid sequence Gly, Ala, Pro (underlined sequence) separate the GAA gene and GILTΔ2-7/A40 tag (upper case sequence). The spacer and tag are placed upstream of GAA residue Ala70. The GILTΔ2-7/A40 cassette contains an Arg to Ala substitution at amino acid 40 of the human IGF2 sequence (uppercase bold).

(SEQ ID NO: 15)

ggtaccagctgctagcaagctaattcacaccaATGGGAATCCCAATGGGG

AAGTCGATGCTGGTGCTTCTCACCTTCTTGGCCTTCGCCTCGTGCTGCAT

-continued

TGCTGCTCTGTGCGGCGGGGAGCTGGTGGACACCCTCCAGTTCGTCTGTG

GGGACCGCGGCTTCTACTTCAGCAGGCCCGCAAGCCGTGTGAGCCGTCGC

AGCGCTGGCATCGTTGAGGAGTGCTGTTTCCGCAGCTGTGACCTGGCCCT

CCTGGAGACGTACTGTGCTACCCCCGCCAAGTCCGAGGGCGCGCCGgcac accccggccgtcccagagcagtgcccacacagtgcgacgtccccccaac agccgcttcgattgcgcccctgacaaggccatcacccaggaacagtgcga ggcccgcggctgctgctacatccctgcaaagcaggggctgcagggagccc agatggggcagccctggtgcttcttcccacccagctaccccagctacaag ctggagaacctgagctcctctgaaatgggctacacggccaccctgacccg taccacccccaccttcttccccaaggacatcctgaccctgcggctggacg tgatgatggagactgagaaccgcctccacttcacgatcaaagatccagct aacaggcgctacgaggtgcccttggagaccccgcgtgtccacagccgggc accgtccccactctacagcgtggagttctctgaggagcccttcggggtga tcgtgcaccggcagctggacggccgcgtgctgctgaacacgacggtggcg cccctgttctttgcggaccagttccttcagctgtccacctcgctgccctc gcagtatatcacaggcctcgccgagcacctcagtcccctgatgctcagca ccagctggaccaggatcaccctgtggaaccgggaccttgcgcccacgccc ggtgcgaacctctacgggtctcaccctttctacctggcgctggaggacgg cgggtcggcacacggggtgttcctgctaaacagcaatgccatggatgtgg tcctgcagccgagccctgcccttagctggaggtcgacaggtgggatcctg gatgtctacatcttcctgggcccagagcccaagagcgtggtgcagcagta cctggacgttgtgggatacccgttcatgccgccatactggggcctgggct tccacctgtgccgctggggctactcctccaccgctatcacccgccaggtg gtggagaacatgaccagggcccacttccccctggacgtccaatggaacga cctggactacatggactcccggagggacttcacgttcaacaaggatggct tccgggacttcccggccatggtgcaggagctgcaccagggcggccggcgc tacatgatgatcgtggatcctgccatcagcagctcgggccctgccgggag ctacaggccctacgacgagggtctgcggagggggttttcatcaccaacg agaccggccagccgctgattgggaaggtatggcccgggtccactgccttc cccgacttcaccaaccccacagccctggcctggtgggaggacatggtggc tgagttccatgaccaggtgcccttcgacggcatgtggattgacatgaacg agccttccaacttcatcaggggctctgaggacggctgccccaacaatgag ctggagaacccaccctacgtgcctggggtggttgggggaccctccaggc ggcaaccatctgtgcctccagccaccagtttctctccacacactacaacc tgcacaacctctacggcctgaccgaagccatcgcctcccacagggcgctg gtgaaggctcgggggacacgcccatttgtgatctcccgctcgacctttgc tggccacggccgatacgccggccactggacgggggacgtgtggagctcct gggagcagctcgcctcctccgtgccagaaatcctgcagtttaacctgctg gggggtgcctctggtcggggccgacgtctgcggcttcctgggcaacacctc agaggagctgtgtgtgcgctggacccagctgggggccttctaccccttca -continued tgcggaaccacaacagcctgctcagtctgccccaggagccgtacagcttc agcgagccggcccagcaggccatgaggaaggccctcaccctgcgctacgc actcctcccccacctctacacgctgttccaccaggcccacgtcgcggggg agaccgtggcccggcccctcttcctggagttccccaaggactctagcacc tggactgtggaccaccagctcctgtgggggggaggccctgctcatcacccc agtgctccaggccgggaaggccgaagtgactggctacttccccttgggca catggtacgacctgcagacggtgccaatagaggcccttggcagcctccca cccccacctgcagctccccgtgagccagccatccacagcgaggggcagtg ggtgacgctgccggccccccctggacaccatcaacgtccacctccgggctg ggtacatcatccccctgcagggccctggcctcacaaccacagagtcccgc cagcagcccatggccctggctgtggccctgaccaagggtggagaggcccg aggggagctgttctgggacgatggagagagcctggaagtgctggagcgag gggcctacacacaggtcatcttcctggccaggaataacacgatcgtgaat gagctggtacgtgtgaccagtgagggagctggcctgcagctgcagaaggt gactgtcctgggcgtggccacggcgccccagcaggtcctctccaacggtg tccctgtctccaacttcacctacagccccgacaccaaggtcctggacatc tgtgtctcgctgttgatgggagagcagtttctcgtcagctggtgttagtc tagagcttgctagcggccgc

Construct 1479

The GILTΔ2-7M1/K37-GAA70-952 cassette below was cloned using the Asp718 and NotI sites of the cassette and vector pCEP4 to produce pCEP-GILTΔ2-7M1/K37-GAA70-952 (Plasmid p1479). Restriction sites for cloning are in lowercase bold. The spacer amino acid sequence Gly, Ala, Pro (underlined sequence) separate the GAA gene and GILTΔ2-7M1/K37 tag (upper case sequence). The spacer and tag are placed upstream of GAA residue Ala70. The GILTΔ2-7M1/K37 cassette contains an Arg to Lys substitution at amino acid 37 of the human IGF-II sequence (uppercase bold).

(SEQ ID NO: 16)

ggtaccaagcttgccATGGGAATCCCAATGGGCAAGTCGATGCTGGTGCT

GCTCACCTTCTTGGCCTTTGCCTCGTGCTGCATTGCCGCTCTGTGCGGCG

GGGAACTGGTGGACACCCTCCAATTCGTCTGTGGGGACCGGGGCTTCTAC

TTCAGCAGACCCGCAAGCCGTGTGAGTAAGCGCAGCCGTGGCATTGTTGA

GGAGTGCTGTTTTCGCAGCTGTGACCTGGCTCTCCTGGAGACGTACTGCG

CTACCCCCGCCAAGTCTGAGGGCGCGCCGgcacaccccggccgtcccaga gcagtgcccacacagtgcgacgtccccccaacagccgcttcgattgcgc ccctgacaaggccatcacccaggaacagtgcgaggcccgcggctgctgct acatccctgcaaagcaggggctgcagggagcccagatggggcagccctgg tgcttcttcccacccagctaccccagctacaagctggagaacctgagctc ctctgaaatgggctacacggccaccctgacccgtaccacccccaccttct tccccaaggacatcctgaccctgcggctggacgtgatgatggagactgag aaccgcctccacttcacgatcaaagatccagctaacaggcgctacgaggt gcccttggagaccccgcgtgtccacagccgggcaccgtccccactctaca -continued

```
gcgtggagttctctgaggagcccttcggggtgatcgtgcaccggcagctg
gacggccgcgtgctgctgaacacgacggtggcgcccctgttctttgcgga
ccagttccttcagctgtccacctcgctgccctcgcagtatatcacaggcc
tcgccgagcacctcagtcccctgatgctcagcaccagctggaccaggatc
accctgtggaaccgggaccttgcgcccacgcccggtgcgaacctctacgg
gtctcaccattctacctggcgctggaggacggcgggtcggcacacggggt
gttcctgctaaacagcaatgccatggatgtggtcctgcagccgagccctg
cccttagctggaggtcgacaggtgggatcctggatgtctacatatcctgg
gcccagagcccaagagcgtggtgcagcagtacctggacgttgtgggatac
ccgttcatgccgccatactggggcctgggatccacctgtgccgctggggc
tactcctccaccgctatcacccgccaggtggtggagaacatgaccagggc
ccacttcccccttggacgtccaatggaacgacctggactacatggactccc
ggagggacttcacgttcaacaaggatggcttccgggacttcccggccatg
gtgcaggagctgcaccagggcggccggcgctacatgatgatcgtggatcc
tgccatcagcagctcgggccctgccgggagctacaggccctacgacgagg
gtctgcggagggggttttcatcaccaacgagaccggccagccgctgatt
gggaaggtatggcccgggtccactgccttccccgacttcaccaaccccac
agccctggcctggtgggaggacatggtggctgagttccatgaccaggtgc
ccttcgacggcatgtggattgacatgaacgagccttccaacttcatcagg
ggactgaggacggctgccccaacaatgagctggagaacccaccctacgtg
cctggggtggttgggggaccctccaggcggcaaccatctgtgcctccag
ccaccagtttctctccacacactacaacctgcacaacctctacggcctga
ccgaagccatcgcctcccacagggcgctggtgaaggctcgggggacacgc
ccatttgtgatctcccgctcgacctttgctggccacggccgatacgccgg
ccactggacgggggacgtgtggagctcctgggagcagctcgcctcctccg
tgccagaaatcctgcagtttaacctgctgggggtgcctctggtcggggcc
```

-continued

```
gacgtctgcggcttcctgggcaacacctcagaggagctgtgtgtgcgctg
gacccagetgggggccttctaccccttcatgcggaaccacaacagcctgc
tcagtctgccccaggagccgtacagcttcagcgagccggcccagcaggcc
atgaggaaggccctcaccagcgctacgcactcctcccccacctctacacg
ctgttccaccaggcccacgtcgcgggggagaccgtggcccggcccctcac
ctggagttccccaaggactctagcacctggactgtggaccaccagctcct
gtgggggaggccagctcatcaccccagtgctccaggccgggaaggccga
agtgactggctacttccccttgggcacatggtacgacctgcagacggtgc
caatagaggcccttggcagcctcccacccccacctgcagctccccgtgag
ccagccatccacagcgaggggcagtgggtgacgctgccggccccctgga
caccatcaacgtccacctccgggctgggtacatcatcccctgcagggcc
ctggcctcacaaccacagagtcccgccagcagcccatggccctggctgtg
gccctgaccaagggtggagaggcccgaggggagctgttctgggacgatgg
agagagcctggaagtgctggagcgaggggcctacacacaggtcatcttcc
tggccaggaataacacgatcgtgaatgagaggtacgtgtgaccagtgagg
gagctggcctgcagctgcagaaggtgactgtcctgggcgtggccacggcg
ccccagcaggtcctctccaacggtgtccctgtctccaacttcacctacag
ccccgacaccaaggtcctggacatctgtgtctcgctgttgatgggagagc
agtttctcgtcagctggtgttagtctagagcttgctagcggccgc
```

Construct 1487

The GILTΔ2-7M1/A37-GAA70-952 cassette below was cloned using the Asp718 and NotI sites of the cassette and vector pCEP4 to produce pCEP-GILTΔ2-7M1/A37-GAA70-952 (Plasmid p1487). Restriction sites for cloning are in lowercase bold. The spacer amino acid sequence Gly, Ala, Pro (underlined sequence) separate the GAA gene and GILTΔ2-7M1/A37 tag (upper case sequence). The spacer and tag are placed upstream of GAA residue Ala70. The GILTΔ2-7M1/A37 cassette contains an Arg to Ala substitution at amino acid 37 of the human IGF-II sequence (uppercase bold).

(SEQ ID NO: 17)

ggtaccaagcttgccATGGGAATCCCAATGGGCAAGTCGATGCTGGTGCTGCTCACCTTCTT

GGCCTTTGCCTCGTGCTGCATTGCCGCTCTGTGCGGCGGGGAACTGGTGGACACCCT

CCAATTCGTCTGTGGGGACCGGGGCTTCTACTTCAGCAGACCCGCAAGCCGTGTGAG

TGCTCGCAGCCGTGGCATTGTTGAGGAGTGCTGTTYTCGCAGCTGTGACCTGGCTCT

CCTGGAGACGTACTGCGCTACCCCCGCCAAGTCTGAG<u>GGCGCGCCG</u>gcacaccccggccgtc ccagagcagtgcccacacagtgcgacgtcccccccaacagccgcttcgattgcgcccctgacaaggccatcacccaggaacagtgcga ggcccgcggctgctgctacatccctgcaaagcaggggctgcagggagcccagatggggcagccaggtgatcttcccacccagctacc ccagctacaagctggagaacctgagctcctctgaaatgggctacacggccaccctgacccgtaccacccccaccacttccccaaggacat cctgaccctgcggctggacgtgatgatggagactgagaaccgcctccacttcacgatcaaagatccagctaacaggcgctacgaggtgcc cttggagaccccgcgtgtccacagccgggcaccgtccccactctacagcgtggagttctctgaggagcccttcggggtgatcgtgcaccg gcagctggacggccgcgtgctgctgaacacgacggtggcgcccctgttctttgcggaccagttccttcagagtccacctcgctgccctcg cagtatatcacaggcctcgccgagcacctcagtcccctgatgctcagcaccagctggaccaggatcaccagtggaaccgggaccttgcg cccacgcccggtgcgaacctctacgggtctcaccctttctacctggcgctggaggacggcgggtcggcacacggggtgttcctgctaaac -continued agcaatgccatggatgtggtcctgcagccgagccctgccatagaggaggtcgacaggtgggatcctggatgtctacatatcctgggccc agagcccaagagcgtggtgcagcagtacctggacgttgtgggatacccgttcatgccgccatactggggcctgggatccacctgtgccg ctggggctactcctccaccgctatcacccgccaggtggtggagaacatgaccagggcccacttcccccctggacgtccaatggaacgacct ggactacatggactcccggagggacttcacgttcaacaaggatggcttccgggacttcccggccatggtgcaggagctgcaccagggcg gccggcgctacatgatgatcgtggatcctgccatcagcagctcgggccctgccgggagctacaggccctacgacgagggtctgcggagg ggggttttcatcaccaacgagaccggccagccgctgattgggaaggtatggcccgggtccactgccttccccgacttcaccaaccccaca gccctggcctggtgggaggacatggtggctgagttccatgaccaggtgcccttcgacggcatgtggattgacatgaacgagccttccaact tcatcaggggctctgaggacggctgccccaacaatgagctggagaacccaccctacgtgcctggggtggttgggggaccctccaggcg gcaaccatctgtgcctccagccaccagtttctctccacacactacaacctgcacaacctctacggcctgaccgaagccatcgcctcccacag ggcgctggtgaaggctcgggggacacgcccatttgtgatctcccgctcgaccatgctggccacggccgatacgccggccactggacgg gggacgtgtggagctcctgggagcagctcgcctcctccgtgccagaaatcctgcagtttaacctgctgggggtgcctctggtcggggccg acgtagcggatcctgggcaacacctcagaggagctgtgtgtgcgctggacccagctgggggccttctaccccttcatgcggaaccacaa cagcctgctcagtctgccccaggagccgtacagcttcagcgagccggcccagcaggccatgaggaaggccctcaccctgcgctacgca ctcctcccccacctctacacgctgttccaccaggcccacgtcgcgggggagaccgtggcccggcccctcttcctggagttccccaaggact ctagcacctggactgtggaccaccagacctgtgggggaggccctgctcatcaccccagtgctccaggccgggaaggccgaagtgact ggctacttccccttgggcacatggtacgacctgcagacggtgccaatagaggcccttggcagcctcccacccccacctgcagctccccgt gagccagccatccacagcgaggggcagtgggtgacgctgccggccccctggacaccatcaacgtccacctccgggctgggtacatca tccccctgcagggccctggcctcacaaccacagagtcccgccagcagcccatggccctggctgtggccctgaccaagggtggagaggc ccgaggggagctgttctgggacgatggagagagcctggaagtgctggagcgaggggcctacacacaggtcatcttcctggccaggaata acacgatcgtgaatgagctggtacgtgtgaccagtgagggagctggcctgcagctgcagaaggtgactgtcctgggcgtggccacggcg ccccagcaggtcctaccaacggtgtccctgtctccaacttcacctacagccccgacaccaaggtcctggacatctgtgtctcgctgttgatg ggagagcagtttctcgtcagctggtgttagtctagagcttgctagcggccgc

Figure 3:
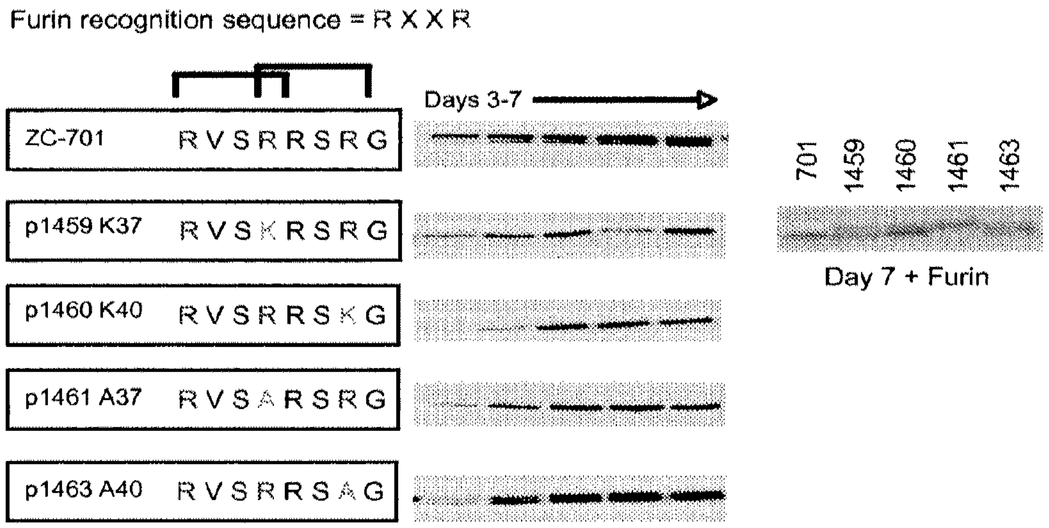

As shown in FIG. 3, three exemplary mutants (i.e., constructs 1459, 1460 and 1461) in which alanine or lysine has been substituted for one of the canonical arginine residues were expressed without detectable cleavage by furin. As also shown in FIG. 3 (right panel), construct 1461 containing a R37A substitution is additionally resistant to addition of exogenous furin.

Construct 1726

The GILTΔ2-7Δ30-39-GAA70-952 cassette below was cloned using the Asp718 and Nod sites of the cassette and vector pCEP4 to produce pCEP-GILTΔ2-7Δ30-39-GAA70-952 (Plasmid 1726). Restriction sites for cloning are in lowercase bold. The spacer amino acid sequence Gly, Ala, Pro (underlined sequence) separate the GAA gene and GILTΔ2-7Δ30-39 tag (upper case sequence). The spacer and tag are placed upstream of GAA residue Ala70. The GILTΔ2-7Δ30-39 cassette contains a deletion of amino acid residues 30-39 (Arg-Pro-Ala-Ser-Arg-Val-Ser-Arg-Arg-Ser) from the human IGF-II sequence.

(SEQ ID NO: 18)

ggtaccagctgctagcaagctaattcacaccaATGGGAATCCCAATGGGGAAGTCGATGCTGGTGCTTC

TCACCTTCTTGGCCTTCGCCTCGTGCTGCATTGCTGCTCTGTGCGGCGGGGAGCTGGT

GGACACCCTCCAGTTCGTCTGTGGGGACCGCGGCTTCTACTTCAGCCGTGGCATCGT

TGAGGAGTGCTGTTTCCGCAGCTGTGACCTGGCCCTCCTGGAGACGTACTGTGCTAC

CCCCGCCAAGTCCGAGGGCGCGCCGgcacaccccggcctacccagaacataacccacacagtgcgacgtcccc cccaacagccgcttcgattgcgcccctgacaaggccatcacccaggaacagtgcgaggcccgcggctgctgctacatccctgcaaagca ggggctgcagggagcccagatggggcagccctggtgcttcttcccacccagctaccccagctacaagctggagaacctgagctcctctga aatgggctacacggccaccctgacccgtaccacccccaccttcttccccaaggacatcctgaccctgcggctggacgtgatgatggagact gagaaccgcctccacttcacgatcaaagatccagctaacaggcgctacgaggtgcccttggagaccccgcgtgtccacagccgggcacc gtccccactctacagcgtggagttctctgaggagcccttcggggtgatcgtgcaccggcagctggacggccgcgtgctgctgaacacgac -continued ggtggcgcccctgttctttgcggaccagttccttcagctgtccacctcgctgccctcgcagtatatcacaggcctcgccgagcacctcagtcc cctgatgctcagcaccagctggaccaggatcaccctgtggaaccgggaccttgcgcccacgcccggtgcgaacctctacgggtctcaccc tttctacctggcgctggaggacggcgggtcggcacacggggtgttcctgctaaacagcaatgccatggatgtggtcctgcagccgagccct gcccttagctggaggtcgacaggtgggatcctggatgtctacatcttcctgggcccagagcccaagagcgtggtgcagcagtacctggac gttgtgggatacccgttcatgccgccatactggggcctgggcttccacctgtgccgctggggctactcctccaccgctatcacccgccaggt ggtggagaacatgaccagggcccacttcccctggacgtccaatggaacgacctggactacatggactcccggagggacttcacgttcaa caaggatggcttccgggacttcccggccatggtgcaggagctgcaccagggcggccggcgctacatgatgatcgtggatcctgccatca gcagctcgggccctgccgggagctacaggccctacgacgagggtctgcggagggggttttcatcaccaacgagaccggccagccgct gattgggaaggtatggcccgggtccactgccttccccgacttcaccaaccccacagccctggcctggtgggaggacatggtggctgagtt ccatgaccaggtgcccttcgacggcatgtggattgacatgaacgagccttccaacttcatcaggggctctgaggacggctgccccaacaat gagctggagaacccaccctacgtgcctggggtggttgggggggaccctccaggcggcaaccatctgtgcctccagccaccagtttctctcc acacactacaacctgcacaacctctacggcctgaccgaagccatcgcctcccacagggcgctggtgaaggctcgggggacacgcccatt tgtgatctcccgctcgacctttgctggccacggccgatacgccggccactggacgggggacgtgtggagctcctgggagcagctcgcctc ctccgtgccagaaatcctgcagtttaacctgctgggggtgcctctggtcggggccgacgtctgcggcttcctgggcaacacctcagaggag ctgtgtgtgcgctggacccagctgggggccttctaccccttcatgcggaaccacaacagcctgctcagtctgccccaggagccgtacagct tcagcgagccggcccagcaggccatgaggaaggccctcaccctgcgctacgcactcctcccccacctctacacgctgttccaccaggcc cacgtcgcgggggagaccgtggcccggcccctcttcctggagttccccaaggactctagcacctggactgtggaccaccagctcctgtgg ggggaggccctgctcatcaccccagtgctccaggccgggaaggccgaagtgactggctacttccccttgggcacatggtacgacctgca gacggtgccaatagaggcccttggcagcctcccacccccacctgcagctccccgtgagccagccatccacagcgaggggcagtgggtg acgctgccggccccctggacaccatcaacgtccacctccgggctgggtacatcatcccctgcagggccctggcctcacaaccacaga gtcccgccagcagcccatggccctggctgtggccctgaccaagggtggagaggcccgaggggagctgttctgggacgatggagagag cctggaagtgctggagcgaggggcctacacacaggtcatcttcctggccaggaataacacgatcgtgaatgagctggtacgtgtgaccag tgagggagctggcctgcagctgcagaaggtgactgtcctgggcgtggccacggcgccccagcaggtcctctccaacggtgtccctgtctc caacttcacctacagccccgacaccaaggtcctggacatctgtgtctcgctgttgatgggagagcagtttctcgtcagctggtgttagtctaga gcttgctagcggccgc

Construct 1749

The GILTΔ2-7Δ31-39-GAA70-952 cassette below was cloned using the Asp718 and NotI sites of the cassette and vector pCEP4 to produce pCEP-GILTΔ2-7Δ31-39-GAA70-952 (Plasmid 1749). Restriction sites for cloning are in lowercase bold. The spacer amino acid sequence Gly, Ala, Pro (underlined sequence) separate the GAA gene and GILTΔ2-7Δ31-39 tag (upper case sequence). The spacer and tag are placed upstream of GAA residue Ala70. The GILTΔ2-7Δ31-39 cassette contains a deletion of amino acid residues 31-39 (Pro-Ala-Ser-Arg-Val-Ser-Arg-Arg-Ser) from the human IGF-II sequence.

(SEQ ID NO: 19)

ggtaccagctgctagcaagctaattcacaccaATGGGAATCCCAATGGGGAAGTCGATGCTGGTGCTIC

TCACCTTCTTGGCCTTCGCCTCGTGCTGCATTGCTGCTCTGTGCGGCGGGGAGCTGGT

GGACACCCTCCAGTTCGTCTGTGGGGACCGCGGCTTCTACTTCAGCAGGCGTGGCAT

CGTTGAGGAGTGCTGTTTCCGCAGCTGTGACCTGGCCCTCCTGGAGACGTACTGTGC

TACCCCCGCCAAGTCCGAGGGCGCGCCGgcacaccccggccgtcccagagcagtgcccacacagtgcgacgt ccccccaacagccgcttcgattgcgcccctgacaaggccatcacccaggaacagtgcgaggcccgcggctgctgctacatccctgcaa agcaggggctgcagggagcccagatggggcagccctggtgcttcttcccacccagctaccccagctacaagctggagaacctgagctcc tctgaaatgggctacacggccaccctgacccgtaccacccccaccttcttccccaaggacatcctgaccctgcggctggacgtgatgatgg agactgagaaccgcctccacttcacgatcaaagatccagctaacaggcgctacgaggtgcccttggagaccccgcgtgtccacagccgg gcaccgtccccactctacagcgtggagttctctgaggagccatcggggtgatcgtgcaccggcagctggacggccgcgtgctgctgaac -continued acgacggtggcgcccctgttctttgcggaccagttccttcagctgtccacctcgctgccctcgcagtatatcacaggcctcgccgagcacct cagtcccctgatgctcagcaccagctggaccaggatcaccctgtggaaccgggaccttgcgcccacgcccggtgcgaacctctacgggt ctcaccctttctacctggcgctggaggacggcgggtcggcacacggggtgttcctgctaaacagcaatgccatggatgtggtcctgcagcc gagccctgccatagctggaggtcgacaggtgggatcctggatgtctacatcttcctgggcccagagcccaagagcgtggtgcagcagta cctggacgttgtgggatacccgttcatgccgccatactggggcctgggcttccacctgtgccgctggggctactcctccaccgctatcaccc gccaggtggtggagaacatgaccagggcccacttcccctggacgtccaatggaacgacctggactacatggactcccggagggacttc acgttcaacaaggatggcttccgggacttcccggccatggtgcaggagctgcaccagggcggccggcgctacatgatgatcgtggatcct gccatcagcagctcgggccctgccgggagctacaggccctacgacgagggtctgcggagggggttttcatcaccaacgagaccggcc agccgctgattgggaaggtatggcccgggtccactgccttccccgacttcaccaaccccacagccctggcctggtgggaggacatggtgg ctgagttccatgaccaggtgccatcgacggcatgtggattgacatgaacgagccttccaacttcatcaggggctctgaggacggctgcccc aacaatgagctggagaacccaccctacgtgcctggggtggttgggggaccctccaggcggcaaccatctgtgcctccagccaccagat ctctccacacactacaacctgcacaacctctacggcctgaccgaagccatcgcctcccacagggcgctggtgaaggctcgggggacacg cccatttgtgatctcccgctcgacctttgctggccacggccgatacgccggccactggacgggggacgtgtggagctcctgggagcagct cgcctcctccgtgccagaaatcctgcagtttaacctgctggggggtgcctctggtcggggccgacgtctgcggcttcctgggcaacacctca gaggagctgtgtgtgcgctggacccagctgggggccttctacccatcatgcggaaccacaacagcctgctcagtctgccccaggagccg tacagcttcagcgagccggcccagcaggccatgaggaaggccctcaccctgcgctacgcactcctcccccacctctacacgctgaccac caggcccacgtcgcgggggagaccgtggcccggcccctatcctggagttccccaaggactctagcacctggactgtggaccaccagct cctgtggggggaggccctgctcatcaccccagtgctccaggccgggaaggccgaagtgactggctacttccccttgggcacatggtacga cctgcagacggtgccaatagaggcccttggcagcctcccacccccacctgcagctccccgtgagccagccatccacagcgaggggcag tgggtgacgctgccggcccccctggacaccatcaacgtccacctccgggctgggtacatcatcccccctgcagggccctggcctcacaacc acagagtcccgccagcagcccatggccctggctgtggccctgaccaagggtggagaggcccgaggggagctgttctgggacgatgga gagagcctggaagtgctggagcgaggggcctacacacaggtcatcttcctggccaggaataacacgatcgtgaatgagctggtacgtgtg accagtgagggagctggcctgcagctgcagaaggtgactgtcctgggcgtggccacggcgccccagcaggtcctctccaacggtgtccc tgtctccaacttcacctacagccccgacaccaaggtcctggacatctgtgtctcgctgttgatgggagagcagtttctcgtcagctggtgttag tctagagcttgctagcggccgc

Construct 1746

The GILTΔ2-7Δ32-39-GAA70-952 cassette below was cloned using the Asp718 and NotI sites of the cassette and vector pCEP4 to produce pCEP-GILTΔ2-7Δ32-39-GAA70-952 (Plasmid 1746). Restriction sites for cloning are in lowercase bold. The spacer amino acid sequence Gly, Ala, Pro (underlined sequence) separate the GAA gene and GILTΔ2-7Δ32-39 tag (upper case sequence). The spacer and tag are placed upstream of GAA residue Ala70. The GILTΔ2-7Δ32-39 cassette contains a deletion of amino acid residues 32-39 (Ala-Ser-Arg-Val-Ser-Arg-Arg-Ser) from the human IGF-II sequence.

(SEQ ID NO: 20)

ggtaccagctgctagcaagctaattcacaccaATGGGAATCCCAATGGGGAAGTCGATGCTGGTGCTTC

TCACCTTCTTGGCCTTCGCCTCGTGCTGCATTGCTGCTCTGTGCGGCGGGGAGCTGGT

GGACACCCTCCAGTTCGTCTGTGGGGACCGCGGCTTCTACTTCAGCAGGCCCCGTGG

CATCGTTGAGGAGTGCTGTTTCCGCAGCTGTGACCTGGCCCTCCTGGAGACGTACTG

TGCTACCCCCGCCAAGTCCGAGGGCGCGCCGgcacaccccggccgtcccagagcagtgcccacacagtgc gacgtcccccccaacagccgcttcgattgcgcccctgacaaggccatcacccaggaacagtgcgaggcccgcggctgctgctacatccc tgcaaagcaggggctgcagggagcccagatggggcagccctggtgcttcttcccacccagctaccccagctacaagctggagaacctga gctcctctgaaatgggctacacggccaccctgacccgtaccacccccaccttcttccccaaggacatcctgaccctgcggctggacgtgat gatggagactgagaaccgcctccacttcacgatcaaagatccagctaacaggcgctacgaggtgcccttggagaccccgcgtgtccacag -continued ccgggcaccgtccccactctacagcgtggagttctctgaggagcccttcggggtgatcgtgcaccggcagctggacggccgcgtgctgct gaacacgacggtggcgcccctgttctttgcggaccagttccttcagctgtccacctcgctgccctcgcagtatatcacaggcctcgccgagc acctcagtcccctgatgctcagcaccagctggaccaggatcaccctgtggaaccgggaccttgcgcccacgcccggtgcgaacctctacg ggtctcaccctttctacctggcgctggaggacggcgggtcggcacacggggtgttcctgctaaacagcaatgccatggatgtggtcctgca gccgagccctgcccttagctggaggtcgacaggtgggatcctggatgtctacatcttcctgggcccagagcccaagagcgtggtgcagca gtacctggacgttgtgggatacccgttcatgccgccatactggggcctgggcttccacctgtgccgctggggctactcctccaccgctatca cccgccaggtggtggagaacatgaccagggcccacttcccccctggacgtccaatggaacgacctggactacatggactcccggaggga cttcacgttcaacaaggatggatccgggacttcccggccatggtgcaggagctgcaccagggcggccggcgctacatgatgatcgtgga tcctgccatcagcagctcgggccctgccgggagctacaggccctacgacgagggtctgcggagggggtatcatcaccaacgagaccg gccagccgctgattgggaaggtatggcccgggtccactgccttccccgacttcaccaaccccacagccctggcctggtgggaggacatg gtggctgagttccatgaccaggtgcccttcgacggcatgtggattgacatgaacgagccttccaacttcatcaggggctctgaggacggctg ccccaacaatgagctggagaacccaccctacgtgcctggggtggttgggggaccctccaggcggcaaccatctgtgcctccagccacc agtttctctccacacactacaacctgcacaacctctacggcctgaccgaagccatcgcctcccacagggcgctggtgaaggctcgggga cacgcccatttgtgatctcccgctcgacctttgctggccacggccgatacgccggccactggacgggggacgtgtggagctcctgggagc agctcgcctcctccgtgccagaaatcctgcagtttaacctgctgggggtgcctctggtcggggccgacgtctgcggcttcctgggcaacac ctcagaggagctgtgtgtgcgctggacccagctgggggccttctacccatcatgcggaaccacaacagcctgctcagtctgccccagga gccgtacagatcagcgagccggcccagcaggccatgaggaaggccctcaccctgcgctacgcactcctcccccacctctacacgctgtt ccaccaggcccacgtcgcgggggagaccgtggcccggcccctatcctggagttccccaaggactctagcacctggactgtggaccacc agctcctgtgggggaggccctgctcatcaccccagtgctccaggccgggaaggccgaagtgactggctacttcccatgggcacatggt acgacctgcagacggtgccaatagaggccatggcagcctcccacccccacctgcagctccccgtgagccagccatccacagcgaggg gcagtgggtgacgctgccggcccccctggacaccatcaacgtccacctccgggctgggtacatcatccccctgcagggccctggcctca caaccacagagtcccgccagcagcccatggccctggctgtggccctgaccaagggtggagaggcccgaggggagctgttctgggacg atggagagagcctggaagtgctggagcgaggggcctacacacaggtcatcttcctggccaggaataacacgatcgtgaatgagctggtac gtgtgaccagtgagggagctggcctgcagctgcagaaggtgactgtcctgggcgtggccacggcgccccagcaggtcctctccaacggt gttagtctagagcttgctagcggccggc

Construct 1747

The GILTΔ2-7Δ33-39-GAA70-952 cassette below was cloned using the Asp718 and NotI sites of the cassette and vector pCEP4 to produce pCEP-GILTΔ2-7Δ33-39-GAA70-952 (Plasmid 1747). Restriction sites for cloning are in lowercase bold. The spacer amino acid sequence Gly, Ala, Pro (underlined sequence) separate the GAA gene and GILTΔ2-7Δ33-39 tag (upper case sequence). The spacer and tag are placed upstream of GAA residue Ala70. The GILTΔ2-7Δ33-39 cassette contains a deletion of amino acid residues 33-39 (Ser-Arg-Val-Ser-Arg-Arg-Ser) from the human IGF-II sequence.

(SEQ ID NO: 21)

ggtaccagctgctagcaagctaattcacaccaATGGGAATCCCAATGGGGAAGTCGATGCTGGTGCTTC

TCACCTTCTTGGCTTCGCCTCGTGCTGCATTGCTGCTCTGTGCGGCGGGGAGCTGGT

GGACACCCTCCAGTTCGTCTGTGGGGACCGCGGCTTCTACTTCAGCAGGCCCGCACG

TGGCATCGTTGAGGAGTGCTGTTTCCGCAGCTGTGACCTGGCCCTCCTGGAGACGTA

CTGTGCTACCCCCGCCAAGTCCGAGGGCGCGCCGgcacaccccggccgtcccagagcagtgcccacaca gtgcgacgtcccccccaacagccgcttcgattgcgcccctgacaaggccatcacccaggaacagtgcgaggcccgcggctgctgctaca tccctgcaaagcaggggctgcagggagcccagatggggcagccctggtgcttcttcccacccagctaccccagctacaagctggagaac ctgagctcctctgaaatgggctacacggccaccctgacccgtaccacccccaccttcttccccaaggacatcctgaccctgcggctggacg tgatgatggagactgagaaccgcctccacttcacgatcaaagatccagctaacaggcgctacgaggtgcccttggagaccccgcgtgtcc acagccgggcaccgtccccactctacagcgtggagttctctgaggagcccttcggggtgatcgtgcaccggcagctggacggccgcgtg -continued ctgctgaacacgacggtggcgcccctgttctttgcggaccagttccttcagctgtccacctcgctgccctcgcagtatatcacaggcctcgcc gagcacctcagtcccctgatgctcagcaccagctggaccaggatcaccctgtggaaccgggaccttgcgcccacgcccggtgcgaacct ctacgggtctcaccctttctacctggcgctggaggacggcgggtcggcacacggggtgttcctgctaaacagcaatgccatggatgtggtc ctgcagccgagccctgcccttagctggaggtcgacaggtgggatcctggatgtctacatcttcctgggcccagagcccaagagcgtggtg cagcagtacctggacgttgtgggatacccgttcatgccgccatactggggcctgggcttccacctgtgccgctggggctactcctccaccg ctatcacccgccaggtggtggagaacatgaccagggcccacttcccccctggacgtccaatggaacgacctggactacatggactcccgga gggacttcacgttcaacaaggatggcttccgggacttcccggccatggtgcaggagctgcaccagggcggccggcgctacatgatgatc gtggatcctgccatcagcagctcgggccctgccgggagctacaggccctacgacgagggtctgcggagggggttttcatcaccaacga gaccggccagccgctgattgggaaggtatggcccgggtccactgccttccccgacttcaccaaccccacagccctggcctggtgggagg acatggtggctgagttccatgaccaggtgcccttcgacggcatgtggattgacatgaacgagccttccaacttcatcaggggctctgaggac ggctgccccaacaatgagctggagaacccaccctacgtgcctggggtggttgggggaccctccaggcggcaaccatctgtgcctccag ccaccagtttctctccacacactacaacctgcacaacctctacggcctgaccgaagccatcgcctcccacagggcgctggtgaaggctcgg gggacacgcccatttgtgatctcccgctcgacctttgctggccacggccgatacgccggccactggacgggggacgtgtggagctcctgg gagcagctcgcctcctccgtgccagaaatcctgcagtttaacctgctgggggtgcctctggtcggggccgacgtctgcggcttcctgggca acacctcagaggagctgtgtgtgcgctggacccagctgggggccttctaccccttcatgcggaaccacaacagcctgctcagtctgcccca ggagccgtacagcttcagcgagccggcccagcaggccatgaggaaggccctcaccctgcgctacgcactcctcccccacctctacacgc tgttccaccaggcccacgtcgcgggggagaccgtggcccggcccctcttcctggagttccccaaggactctagcacctggactgtggacc accagctcctgtgggggaggccctgctcatcaccccagtgctccaggccgggaaggccgaagtgactggctacttccccttgggcacat ggtacgacctgcagacggtgccaatagaggcccttggcagcctcccacccccacctgcagctccccgtgagccagccatccacagcgag gggcagtgggtgacgctgccggccccctggacaccatcaacgtccacctccgggctgggtacatcatcccccctgcagggccctggcct cacaaccacagagtcccgccagcagcccatggccctggctgtggccctgaccaagggtggagaggcccgaggggagctgttctgggac gatggagagagcctggaagtgctggagcgaggggcctacacacaggtcatcttcctggccaggaataacacgatcgtgaatgagctggt acgtgtgaccagtgagggagctggcctgcagctgcagaaggtgactgtcctgggcgtggccacggcgccccagcaggtcctctccaacg gtgtccctgtctccaacttcacctacagccccgacaccaaggtcctggacatctgtgtctcgctgttgatgggagagcagtttctcgtcagctg gtgttagtctagagcttgctagcggccgc

Construct 1758

The GILTΔ2-7Δ34-39-GAA70-952 cassette below was cloned using the Asp718 and NotI sites of the cassette and vector pCEP4 to produce pCEP-GILTΔ2-7Δ34-39-GAA70-952 (Plasmid 1758). Restriction sites for cloning are in lowercase bold. The spacer amino acid sequence Gly, Ala, Pro (underlined sequence) separate the GAA gene and GILTΔ2-7Δ34-39 tag (upper case sequence). The spacer and tag are placed upstream of GAA residue Ala70. The GILTΔ2-7Δ34-39 cassette contains a deletion of amino acid residues 34-39 (Arg-Val-Ser-Arg-Arg-Ser) from the human IGF-II sequence.

(SEQ ID NO: 22)

ggtaccagctgctagcaagctaattcacaccaATGGGAATCCCAATGGGGAAGTCGATGCTGGTGCTTC

TCACCTTCTTCTGCCTTCGCCTCGTGCTGCATTGCTGCTCTGTGCGGCGGGGAGCTGGT

GGACACCCTCCAGTTCGTCTGTGGGGACCGCGGCTTCTACTTCAGCAGGCCCGCAAG

CCGTGGCATCGTTGAGGAGTGCTGTTTCCGCAGCTGTGACCTGGCCCTCCTTGGAGAC

GTACTGTGCTACCCCCGCCAAGTCCGAGGGCGCGCCGgcacaccccggccgtcccagagcagtgccc acacagtgcgacgtcccccccaacagccgcttcgattgcgcccctgacaaggccatcacccaggaacagtgcgaggcccgcggctgct gctacatccctgcaaagcaggggctgcagggagcccagatggggcagccctggtgcttcttcccacccagctaccccagctacaagctg gagaacctgagctcctctgaaatgggctacacggccaccctgacccgtaccacccccaccttcttccccaaggacatcctgaccctgcggc tggacgtgatgatggagactgagaaccgcctccacttcacgatcaaagatccagctaacaggcgctacgaggtgcccttggagaccccgc -continued gtgtccacagccgggcaccgtccccactctacagcgtggagttctctgaggagcccttcggggtgatcgtgcaccggcagctggacggcc gcgtgctgctgaacacgacggtggcgcccctgttctttgcggaccagttccttcagctgtccacctcgctgccctcgcagtatatcacaggcc tcgccgagcacctcagtcccctgatgctcagcaccagctggaccaggatcaccctgtggaaccgggaccttgcgcccacgcccggtgcg aacctctacgggtctcaccctttctacctggcgctggaggacggcgggtcggcacacggggtggtcctgctaaacagcaatgccatggatg tggtcctgcagccgagccctgcccttagctggaggtcgacaggtgggatcctggatgtctacatcttcctgggcccagagcccaagagcgt ggtgcagcagtacctggacgttgtgggatacccgttcatgccgccatactggggcctgggcttccacctgtgccgctggggctactcctcca ccgctatcacccgccaggtggtggagaacatgaccagggcccaccccccctggacgtccaatggaacgacctggactacatggactccc ggagggacttcacgttcaacaaggatggcttccgggacttcccggccatggtgcaggagctgcaccagggcggccggcgctacatgatg atcgtggatcctgccatcagcagctcgggccctgccgggagctacaggccctacgacgagggtctgcggagggggttttcatcaccaac gagaccggccagccgctgattgggaaggtatggcccgggtccactgccttccccgacttcaccaaccccacagccctggcctggtggga ggacatggtggctgagttccatgaccaggtgcccttcgacggcatgtggattgacatgaacgagccttccaacttcatcaggggctctgagg acggctgccccaacaatgagctggagaacccaccctacgtgcctggggtggttgggggaccctccaggcggcaaccatctgtgcctcc agccaccagtttctctccacacactacaacctgcacaacctctacggcctgaccgaagccatcgcctcccacagggcgctggtgaaggctc gggggacacgcccatttgtgatctcccgctcgacctttgctggccacggccgatacgccggccactggacgggggacgtgtggagctcct gggagcagctcgcctcctccgtgccagaaatcctgcagtttaacctgctgggggtgcctctggtcggggccgacgtctgcggcttcctggg caacacctcagaggagctgtgtgtgcgctggacccagctgggggccttctaccccttcatgcggaaccacaacagcctgctcagtctgccc caggagccgtacagcttcagcgagccggcccagcaggccatgaggaaggccctcaccctgcgctacgcactcctcccccacctctacac gctgttccaccaggcccacgtcgcgggggagaccgtggcccggcccctcttcctggagttccccaaggactctagcacctggactgtgga ccaccagacctgtgggggggaggccctgctcatcaccccagtgctccaggccgggaaggccgaagtgactggctacttccccttgggca catggtacgacctgcagacggtgccaatagaggcccttggcagcctcccacccccacctgcagctccccgtgagccagccatccacagc gaggggcagtgggtgacgctgccggccccccctggacaccatcaacgtccacctccgggctgggtacatcatccccctgcagggccctgg cctcacaaccacagagtcccgccagcagcccatggccctggctgtggccctgaccaagggtggagaggcccgaggggagctgttctgg gacgatggagagagcctggaagtgctggagcgaggggcctacacacaggtcatcttcctggccaggaataacacgatcgtgaatgagct ggtacgtgtgaccagtgagggagctggcctgcagctgcagaaggtgactgtcctgggcgtggccacggcgccccagcaggtcctacca acggtgtccctgtctccaacttcacctacagccccgacaccaaggtcctggacatctgtgtctcgctgttgatgggagagcagtttctcgtca gctggtgttagtctagagcttgctagcggccgc

Construct 1750

The GILTΔ2-7Δ35-39-GAA70-952 cassette below was cloned using the Asp718 and NotI sites of the cassette and vector pCEP4 to produce pCEP-GILTΔ2-7Δ35-39-GAA70-952 (Plasmid 1750). Restriction sites for cloning are in lowercase bold. The spacer amino acid sequence Gly, Ala, Pro (underlined sequence) separate the GAA gene and GILTΔ2-7Δ35-39 tag (upper case sequence). The spacer and tag are placed upstream of GAA residue Ala70. The GILTΔ2-7Δ35-39 cassette contains a deletion of amino acid residues 35-39 (Val-Ser-Arg-Arg-Ser) from the human IGF-II sequence.

(SEQ ID NO: 23)

ggtaccagctgctagcaagctaattcacaccaATGGGAATCCCAATGGGGAAGTCGATGCTGGTGCTTC

TCACCTTCTTGGCCTTCGCCTCGTGCTGCATTGCTGCTCTGTGCGGCGGGGAGCTGGT

GGACACCCTCCAGTTCGTCTGTGGGGACCGCGGCTTCTACTTCAGCAGGCCCGCAAG

CCGTCGTGGCATCGTTGAGGAGTGCTGTTTCCGCAGCTGTGACCTGGCCCTCCTGGA

GACGTACTGTGCTACCCCCGCCAAGTCCGAGGGCGCGCCGgcacaccccggccgtcccagagcag tgcccacacagtgcgacgtcccccccaacagccgcttcgattgcgcccctgacaaggccatcacccaggaacagtgcgaggcccgcgg ctgctgctacatccctgcaaagcaggggctgcagggagcccagatggggcagccctggtgatcttcccacccagctaccccagctacaa gctggagaacctgagctcctctgaaatgggctacacggccaccctgacccgtaccacccccaccttcttccccaaggacatcctgaccctg cggctggacgtgatgatggagactgagaaccgcctccacttcacgatcaaagatccagctaacaggcgctacgaggtgcccttggagacc -continued ccgcgtgtccacagccgggcaccgtccccactctacagcgtggagttctctgaggagccatcggggtgatcgtgcaccggcagctggac ggccgcgtgctgctgaacacgacggtggcgcccctgttattgcggaccagttccttcagctgtccacctcgctgccctcgcagtatatcaca ggcctcgccgagcacctcagtcccctgatgctcagcaccagctggaccaggatcaccctgtggaaccgggaccttgcgcccacgcccgg tgcgaacctctacgggtctcaccctttctacctggcgctggaggacggcgggtcggcacacggggtgttcctgctaaacagcaatgccatg gatgtggtcctgcagccgagccctgcccttagctggaggtcgacaggtgggatcctggatgtctacatcttcctgggcccagagcccaaga gcgtggtgcagcagtacctggacgttgtgggatacccgttcatgccgccatactggggcctgggatccacctgtgccgctggggctactc ctccaccgctatcacccgccaggtggtggagaacatgaccagggcccacttcccccctggacgtccaatggaacgacctggactacatgga ctcccggagggacttcacgttcaacaaggatggcaccgggacttcccggccatggtgcaggagctgcaccagggcggccggcgctaca tgatgatcgtggatcctgccatcagcagctcgggccctgccgggagctacaggccctacgacgagggtctgcggagggggtttttcatca ccaacgagaccggccagccgctgattgggaaggtatggcccgggtccactgccttccccgacttcaccaaccccacagccctggcctggt gggaggacatggtggctgagttccatgaccaggtgccatcgacggcatgtggattgacatgaacgagccttccaacttcatcaggggctct gaggacggctgccccaacaatgagaggagaacccaccctacgtgcctggggtggttgggggaccctccaggcggcaaccatctgtg cctccagccaccagtttctctccacacactacaacctgcacaacctctacggcctgaccgaagccatcgcctcccacagggcgctggtgaa ggctcgggggacacgcccatttgtgatctcccgctcgacctttgctggccacggccgatacgccggccactggacgggggacgtgtgga gctcctgggagcagctcgcctcctccgtgccagaaatcctgcagtttaacctgctgggggtgcctctggtcggggccgacgtagcggctt cctgggcaacacctcagaggagctgtgtgtgcgctggacccagctgggggccttctacccatcatgcggaaccacaaCagcCtgctcag tctgccccaggagccgtacagcttcagcgagccggcccagcaggccatgaggaaggccctcaccagcgctacgcactcctcccccacc tctacacgctgttccaccaggcccacgtcgcgggggagaccgtggcccggcccctcttcctggagttccccaaggactctagcacctgga ctgtggaccaccagctcctgtgggggaggccctgctcatcaccccagtgctccaggccgggaaggccgaagtgactggctacttcccct tgggcacatggtacgacctgcagacggtgccaatagaggcccttggcagcacccacccccacctgcagctccccgtgagccagccatc cacagcgaggggcagtgggtgacgctgccggccccctggacaccatcaacgtccacctccgggctgggtacatcatcccctgcagg gccctggcctcacaaccacagagtcccgccagcagcccatggccctggctgtggccctgaccaagggtggagaggcccgaggggagc tgttctgggacgatggagagagcctggaagtgctggagcgaggggcctacacacaggtcatcttcctggccaggaataacacgatcgtga atgagctggtacgtgtgaccagtgagggagctggcctgcagctgcagaaggtgactgtcctgggcgtggccacggcgccccagcaggtc ctctccaacggtgtccctgtctccaacttcacctacagccccgacaccaaggtcctggacatctgtgtctcgctgttgatgggagagcagtttc tcgtcagctggtgttagtctagagcttgctagcggccgc

Construct 1748

The GILTΔ2-7Δ36-39-GAA70-952 cassette below was cloned using the Asp718 and NotI sites of the cassette and vector pCEP4 to produce pCEP-GILTΔ2-7Δ36-39-GAA70-952 (Plasmid 1748). Restriction sites for cloning are in lowercase bold. The spacer amino acid sequence Gly, Ala, Pro (underlined sequence) separate the GAA gene and GILTΔ2-7Δ36-39 tag (upper case sequence). The spacer and tag are placed upstream of GAA residue Ala70. The GILTΔ2-7Δ36-39 cassette contains a deletion of amino acid residues 36-39 (Ser-Arg-Arg-Ser) from the human IGF-II sequence.

(SEQ ID NO: 24)

ggtaccagctgctagcaagctaattcacaccaATGGGAATCCCAATGGGGAAGTCGATGCTGGTGCTTC

TCACCTTCTTGGCCTTCGCCTCGTGCTGCATTGCTGCTCTGTGCGGCGGGGAGCTGGT

GGACACCCTCCAGTTCGTCTGTGGGGACCGCGGCTTCTACTTCAGCAGGCCCGCAAG

CCGTGTGCGTGGCATCGTTGAGGAGTGCTGTTTCCGCAGCTGTGACCTGGCCCTCCT

GGAGACGTACTGTGCTACCCCCGCCAAGTCCGAGGGCGCGCCGgcacaccccggccgtcccag agcagtgcccacacagtgcgacgtcccccccaacagccgcttcgattgcgcccctgacaaggccatcacccaggaacagtgcgaggcc cgcggctgctgctacatccctgcaaagcaggggctgcagggagcccagatggggcagccctggtgcttcttcccacccagctaccccag ctacaagctggagaacctgagctcctctgaaatgggctacacggccaccctgacccgtaccacccccaccttcttccccaaggacatcctg -continued accctgcggctggacgtgatgatggagactgagaaccgcctccacttcacgatcaaagatccagctaacaggcgctacgaggtgcccttg gagaccccgcgtgtccacagccgggcaccgtccccactctacagcgtggagttctctgaggagcccttcggggtgatcgtgcaccggca gctggacggccgcgtgctgctgaacacgacggtggcgcccctgttattgcggaccagttccttcagctgtccacctcgctgccctcgcagt atatcacaggcctcgccgagcacctcagtcccctgatgctcagcaccagctggaccaggatcaccctgtggaaccgggaccttgcgccca cgcccggtgcgaacctctacgggtctcaccattctacctggcgctggaggacggcgggtcggcacacggggtgttcctgctaaacagca atgccatggatgtggtcctgcagccgagccctgccatagctggaggtcgacaggtgggatcctggatgtctacatcttcctgggcccaga gcccaagagcgtggtgcagcagtacctggacgttgtgggatacccgttcatgccgccatactggggcctgggcttccacctgtgccgctgg ggctactcctccaccgctatcacccgccaggtggtggagaacatgaccagggcccacttcccccctggacgtccaatggaacgacctggac tacatggactcccggagggacttcacgttcaacaaggatggcttccgggacttcccggccatggtgcaggagctgcaccagggcggccg gcgctacatgatgatcgtggatcctgccatcagcagacgggccctgccgggagctacaggccctacgacgagggtctgcggaggggg gttttcatcaccaacgagaccggccagccgctgattgggaaggtatggcccgggtccactgccttccccgacttcaccaaccccacagccc tggcctggtgggaggacatggtggctgagttccatgaccaggtgcccttcgacggcatgtggattgacatgaacgagccttccaacttcatc aggggctctgaggacggctgccccaacaatgagctggagaacccaccctacgtgcctggggtggttgggggggaccctccaggcggcaa ccatagtgcctccagccaccagtttctctccacacactacaacctgcacaacctctacggcctgaccgaagccatcgcctcccacagggc gctggtgaaggctcgggggacacgcccatttgtgatctcccgctcgacctttgctggccacggccgatacgccggccactggacggggg acgtgtggagctcctgggagcagctcgcctcctccgtgccagaaatcctgcagtttaacctgctgggggtgcctctggtcggggccgacgt ctgcggcttcctgggcaacacctcagaggagctgtgtgtgcgctggacccagctgggggccttctaccccttcatgcggaaccacaacag cctgctcagtctgccccaggagccgtacagcttcagcgagccggcccagcaggccatgaggaaggccctcaccctgcgctacgcactcc tcccccacctctacacgctgttccaccaggcccacgtcgcgggggagaccgtggcccggcccctcttcctggagttccccaaggactcta gcacctggactgtggaccaccagctcctgtggggggaggccctgacatcaccccagtgctccaggccgggaaggccgaagtgactgg ctacttccccttgggcacatggtacgacctgcagacggtgccaatagaggcccttggcagcctcccacccccacctgcagctccccgtgag ccagccatccacagcgaggggcagtgggtgacgctgccggcccccctggacaccatcaacgtccacctccgggctgggtacatcatccc cctgcagggccctggcctcacaaccacagagtcccgccagcagcccatggccctggctgtggccctgaccaagggtggagaggcccga ggggagctgttagggacgatggagagagcctggaagtgctggagcgaggggcctacacacaggtcatatcctggccaggaataacac gatcgtgaatgagctggtacgtgtgaccagtgagggagctggcctgcagctgcagaaggtgactgtcctgggcgtggccacggcgcccc agcaggtcctctccaacggtgtccctgtctccaacttcacctacagccccgacaccaaggtcctggacatctgtgtctcgctgttgatgggag agcagtttctcgtcagctggtgttagtctagagcttgctagcggccgc

Construct 1751

The GILTΔ2-7Δ29-40-GAA70-952 cassette below was cloned using the Asp718 and NotI sites of the cassette and vector pCEP4 to produce pCEP-GILTΔ2-7Δ29-40-GAA70-952 (Plasmid 1751). Restriction sites for cloning are in lowercase bold. The spacer amino acid sequence Gly, Ala, Pro (underlined sequence) separate the GAA gene and GILTΔ2-7Δ29-40 tag (upper case sequence). The spacer and tag are placed upstream of GAA residue Ala70. The GILTΔ2-7Δ29-40 cassette contains a deletion of amino acid residues 29-40 (Ser-Arg-Pro-Ala-Ser-Arg-Val-Ser-Arg-Arg-Ser-Arg) from the human IGF-II sequence.

(SEQ ID NO: 25)

ggtaccagctgctagcaagctaattcacaccaATGGGAATCCCAATGGGGAAGTCGATGCTGGTGCTTC

TCACCTTCTTGGCCTTCGCCTCGTGCTGCATTGCTGCTCTGTGCGGCGGGGAGCTGGT

GGACACCCTCCAGTTCGTCTGTGGGGACCGCGGCTTCTACTTCGGCATCGTTGAGGA

GTGCTGTTTCCGCAGCTGTGACCTGGCCCTCCTGGAGACGTACTGTGCTACCCCCGC

CAAGTCCGAG<u>GGCGCGCCG</u>gcacaccccggccgtcccagagcagtgcccacacagtgcgacgtccccccaacagc cgcttcgattgcgcccctgacaaggccatcacccaggaacagtgcgaggcccgcggctgctgctacatccctgcaaagcaggggctgca gggagcccagatggggcagccctggtgcacttcccacccagctaccccagctacaagctggagaacctgagctcctctgaaatgggcta cacggccaccctgacccgtaccacccccaccacttccccaaggacatcctgaccagcggctggacgtgatgatggagactgagaaccg -continued cctccacttcacgatcaaagatccagctaacaggcgctacgaggtgcccttggagaccccgcgtgtccacagccgggcaccgtccccact ctacagcgtggagttctctgaggagcccttcggggtgatcgtgcaccggcagctggacggccgcgtgctgctgaacacgacggtggcgc ccctgttctttgcggaccagttcatcagctgtccacctcgctgccctcgcagtatatcacaggcctcgccgagcacctcagtcccctgatgct cagcaccagctggaccaggatcaccctgtggaaccgggaccttgcgcccacgcccggtgcgaacctctacgggtctcaccattctacct ggcgctggaggactttcgggtcggcacacggggtgttcctgctaaacagcaatgccatggatgtggtcctgcagccgagccctgccctta gctggaggtcgacaggtgggatccggatgtctacatcttcagggcccagagcccaagagcgtggtgcagcagtacctggacgttgtgg gatacccgttcatgccgccataaggggcagggatccacctgtgccgctggggctactcctccaccgctatcacccgccaggtggtgga gaacatgaccagggcccacttccccaggacgtccaatggaacgacctggactacatggactcccggagggacttcacgttcaacaagga tggatccgggacttcccggccatggtgcaggagctgcaccagggcggccggcgctacatgatgatcgtggatcctgccatcagcagctc gggccctgccgggagctacaggccctacgacgagggtctgcggagggggttttcatcaccaacgagaccggccagccgctgattggg aaggtatggcccgggtccactgccttccccgacttcaccaaccccacagccctggcctggtgggaggacatggtggctgagttccatgac caggtgcccttcgacggcatgtggattgacatgaacgagccttccaacttcatcaggggctctgaggacggctgccccaacaatgagctgg agaacccaccctacgtgcctggggtggttgggggaccctccaggcggcaaccatctgtgcctccagccaccagtttctctccacacacta caacctgcacaacctctacggcctgaccgaagccatcgcctcccacagggcgctggtgaaggctcgggggacacgcccatttgtgatctc ccgctcgacattgctggccacggccgatacgccggccactggacgggggacgtgtggagctcctgggagcagctcgcctcctccgtgc cagaaatcctgcagtttaacctgctgggggtgcctctggtcggggccgacgtctgcggcttcctgggcaacacctcagaggagctgttttgt gcgctggacccagctgggggccttctacccatcatgcggaaccacaacagcctgctcagtagccccaggagccgtacagcttcagcga gccggcccagcaggccatgaggaaggccctcaccagcgctacgcactcctcccccacctctacacgctgttccaccaggcccacgtcg cgggggagaccgtggcccggcccctcttcctggagttccccaaggactctagcacctggactgtggaccaccagctcctgtgggggag gccctgctcatcaccccagtgctccaggccgggaaggccgaagtgactggctacttccccttgggcacatggtacgacctgcagacggtg ccaatagaggcccttggcagcctcccacccccacctgcagctccccgtgagccagccatccacagcgaggggcagtgggtgacgctgc cggcccccctggacaccatcaacgtccacctccgggctgggtacatcatcccccctgcagggccaggcctcacaaccacagagtcccgc cagcagcccatggccctggctgtggccctgaccaagggtggagaggcccgaggggagctgttctgggacgatggagagagcctggaa gtgctggagcgaggggcctacacacaggtcatcttcctggccaggaataacacgatcgtgaatgagctggtacgtgtgaccagtgaggga gctggcctgcagctgcagaaggtgactgtcagggcgtggccacggcgccccagcaggtcctaccaacggtgtccctgtctccaacttca cctacagccccgacaccaaggtcctggacatctgtgtctcgctgttgatgggagagcagtttctcgtcagctggtgttagtctagagcttgcta gcggccgc

Construct 1752

The GILTΔ2-7Δ30-40-GAA70-952 cassette below was cloned using the Asp718 and NotI sites of the cassette and vector pCEP4 to produce pCEP-GILTΔ2-7Δ30-40-GAA70-952 (Plasmid 1752). Restriction sites for cloning are in lowercase bold. The spacer amino acid sequence Gly, Ala, Pro (underlined sequence) separate the GAA gene and GILTΔ2-7Δ30-40 tag (upper case sequence). The spacer and tag are placed upstream of GAA residue Ala70. The GILTΔ2-7Δ30-40 cassette contains a deletion of amino acid residues 30-40 (Arg-Pro-Ala-Ser-Arg-Val-Ser-Arg-Arg-Ser-Arg) from the human IGF-II sequence.

(SEQ ID NO: 26)

ggtaccagctgctagcaagctaattcacaccaATGGGAATCCCAATGGGGAAGTCGATGCTGGTGCTTC

TCACCTTCTTGGCCTTCGCCTCGTGCTGCATTGCTGCTCTGTGCGGCGGGGAGCTGGT

GGACACCCTCCAGTTCGTCTGTGGGGACCGCGGCTTCTACTTCAGCGGCATCGTTGA

GGAGTGCTGTTTCCGCAGCTGTGACCTGGCCCTCCTGGAGACGTACTGTGCTACCCC

CGCCAAGTCCGAGGGCGCGCCGgcacaccccggccgtcccagagcagtgcccacacagtgcgacgtcccccccaa cagccgcttcgattgcgcccctgacaaggccatcacccaggaacagtgcgaggcccgcggctgctgctacatccctgcaaagcaggggc tgcagggagcccagatggggcagcctggtgcttcttcccacccagctaccccagctacaagctggagaacctgagctcctctgaaatgg -continued gctacacggccaccctgacccgtaccacccccaccttcttccccaaggacatcctgaccctgcggctggacgtgatgatggagactgaga accgcctccacttcacgatcaaagatccagctaacaggcgctacgaggtgcccttggaccccgcgtgtccacagccgggcaccgtcc ccactctacagcgtggagttctctgaggagcccttcggggtgatcgtgcaccggcagctggacggccgcgtgctgaacacgacggtg gcgcccctgttctttgcggaccagttccttcagctgtccacctcgctccctcgcagtatatcacaggcctcgccgagcacctcagtcccctg atgctcagcaccagctggaccaggatcaccctgtggaaccgggaccttgcgcccacgcccggtgcgaacctctacgggtctcaccctttct acctggcgctggaggacggcgggtcggcacacggggtgttcctgctaaacagcaatgccatggatgtggtcctgcagccgagccctgcc ccttagctggaggtcgacaggtgggatc-
ctggatgctctacatcttccttgggcccagagcccaagagcgtggtgcagcagtacctggacgtttg tgggatacccgttcatgccgccatactggggcctgggcttccacctgtgccgctggggctactcaccaccgctatcacccgccaggtggt ggagaacatgaccagggcccacttcccccctggacgtccaatggaacgacctggactacatggactcccggagggacttcacgttcaacaa ggatggcttccgggacttcccggccatggtgcaggagctgcaccagggcggccggcgctacatgatgatcgtggatcctgccatcagca gctcgggccctgccgggagctacaggccctacgacgagggtctgcggagggggttacatcaccaacgagaccggccagccgctgatt gggaaggtatggcccgggtccactgccttccccgacccaccaaccccacagccctggcctggtgggaggacatggtggctgagttccat gaccaggtgcccttcgacggcatgtggattgacatgaacgagccttccaacttcatcaggggctctgaggacggctgccccaacaatgag ctggagaacccaccctacgtgcctggggtggttgggggaccctccaggcggcaaccatctgtgcctccagccaccagtttctctccacac actacaacctgcacaacctctacggcctgaccgaagccatcgcctcccacagggcgctggtgaaggctcgggggacacgcccatcgtga tctcccgctcgacctttgctggccacggccgatacgccggccactggacgggggacgtgtggagctcctgggagcagctcgcctcctccg tgccagaaatcctgcagtttaacctgctgggggtgcctctggtcggggccgacgtctgcggcttcctgggcaacacctcagaggagctgtg tgtgcgctggacccagctgggggccttctaccccttcatgcggaaccacaacagcctgctcagtctgccccaggagccgtacagcttcagc gagccggcccagcaggccatgaggaaggccctcaccctgcgctacgcactcctcccccacctctacacgctgttccaccaggcccacgt cgcgggggagagccgtggcccggcccctcttcctggagttccccaaggactctagcacctggactgtggaccaccagctcctgtgggggg aggccctgctcatcaccccagtgctccaggccgggaaggccgaagtgactggctacttccccttgggcacatggtacgacctgcagacgg tgccaatagaggcccttggcagcctcccacccccacctgcagctccccgtgagccagccatccacagcgaggggcagtgggtgacgctg ccggccccctggacaccatcaacgtccacctccgggctgggtacatcctcccctgcagggccctggcctcacaaccacagagtcccg ccagcagcccatggccctggctgtggccctgaccaagggtggagaggcccgaggggagctgttctgggacgatggagagagcctgga agtgctggagcgagggcctacacacaggtcatcttcctggccaggaataacacgatcgtgaatgagctggtacgtgtgaccagtgaggg agctggcctgcagctgcagaaggtgactgtcctgggcgtggccacggcgccccagcaggtcctctccaacggtgtccccgtctccaacttc acctacagccccgacaccaaggtcctg-
gacatctgtgtctcgctgttgatgggagagcagtttctcgtcagctggtgttagtctagagcttgcc agcggccgc

Construct 1753

The GILTΔ2-7Δ31-40-GAA70-952 cassette below was cloned using the Asp718 and NotI sites of the cassette and vector pCEP4 to produce pCEP-GILTΔ2-7Δ31-40-GAA70-952 (Plasmid 1753). Restriction sites for cloning are in lowercase bold. The spacer amino acid sequence Gly, Ala, Pro (underlined sequence) separate the GAA gene and GILTΔ2-7Δ31-40 tag (upper case sequence). The spacer and tag are placed upstream of GAA residue Ala70. The GILTΔ2-7Δ31-40 cassette contains a deletion of amino acid residues 31-40 (Pro-Ala-Ser-Arg-Val-Ser-Arg-Arg-Ser-Arg) from the human IGF-II sequence.

(SEQ ID NO: 27)

ggtaccagctgctagcaagctaattcacaccaATGGGAATCCCAATGGGGAAGTCGATGCTGGTGCTTC

TCACCTTCTTGGCCTTCGCCTCGTGCTGCATTGCTGCTCTGTGCGGCGGGGAGCTGGT

GGACACCCTCCAGTTCGTCTGTGGGGACCGCGGCTTCTACTTCAGCAGGGGCATCGT

TGAGGAGTGCTGTTTCCGCAGCTGTGACCTGGCCCTCCTGGAGACGTACTGTGCTAC

CCCCGCCAAGTCCGAGGGCGCGCCGgcacaccccggccgtccgtcccagagcagtgcccacacagtgcgacgtcccc cccaacagccgcttcgattgcgcccctgacaaggccatcacccaggaacagtgcgaggcccgcggctgctgctacatccctgcaaagca -continued ggggctgcagggagcccagatggggcagccctggtgcttcttcccacccagctaccccagctacaagctggagaacctgagctcctctga aatgggctacacggccaccctgacccgtaccaccccccaccttcttccccaaggacatcctgaccctgcggctggacgtgatgatggagact gagaaccgcctccacttcacgatcaaagatccagctaacaggcgctacgaggtgcccttggagaccccgcgtgtccttcagccgggcacc gtccccttctctacagcgtggagttctctgaggagcccttcggggtgatcgtgcaccggcagctggacggccgcgtgctgctgaacacgac ggtggcgcccctgttctttgcggac-
cagttccttcagctgtccacctcgctgccttgcgcccacgcccggtgcgaacctctacgggtctcaccc cctgatgctcagcaccagctggaccaggatcaccctgtggaaccgggaccttgcgcccacgcccggtgcgaacctctacgggtctcaccc tttctacctggcgctggaggacggcgggtcggcacacggggtgttcctgctaaacagcaatgccatggatgtggtcctgcagccgagccct gcccttagctggaggtcgacaggtgggatcctggatgtctacatcttcctgggcccagagcccangagcgtggtgcagcagtacctggac gttgtgggatacccgttcatgccgccat-
actggggcctgggcttccacctgtgccgctggggctactcctccaccgctatcacccgccaggt ggtggagaacatgaccagggcccacttcccccctggacgtccaatggaacgacctggactacatggactcccggagggacttcacgttcaa caaggatggctttcgggacttcccggccatggtgcaggagctgcaccagggcggccggcgctacatgatgatcgtggatcctgccatca gcagctcgtccctgccgggagctacaggccctacgacgagggtctgcggagggggttttcatcaccaacgagaccggccagccgct gattgggaaggtatggcccgggtccactgccttccccgacttcaccaaccccacagccctggcctggtgggaggacatggtggctgagtt ccatgaccaggtgcccttcgacggcatgtggattgacatgaacgagccttccaacttcatcaggggctctgaggacggctgccccaacaat gagctggagaatccaccctacgtgcctggggtggttgggggggaccctccaggcggcaaccatctgtgcctccagccaccagtttctctcc acacactacaacctgcacaacctctacggcctgaccgaagccatcgcctcccacagggcgctggtgaaggctcgggggacacgcccatt tgtgatctcccgctcgacctttgctggccacggccgatacgccggccactggacgggggacgtgtggagctcctgggagcagcttgcctc ctccgtgccagaaatcctgcagtttaac-
ctgctgggggtgcctctggtcggggccgacgtctgcggcttcctgggcattcacctcagaggag ctgtgtgtgcgctggacccagctgggggccttctaccccttcatgcggaaccacaacagcctgctcagtctgccccaggagccgtacagct tcagcgagccggcccagcaggccatgaggaaggccctcaccctgcgctacgcactcctcccccacctctacacgctgttccaccaggcc cacgtcgcgggggagaccgtggcccggcccctcttcctggagttccccaaggactctagcacctggactgtggaccaccagctcctgtgg ggggaggccctgctcatcaccccagtgctccaggccgggaaggccgaagtgactggctacttccccttgggcacatggtacgacctgca gacggtgccaatagaggcccttggcagcctcccacccccacctgcagctccccgtgagccagccatccacagcgaggggcagtgggtg acgctgccggccccctggacaccatcaacgtccacctccgggctgggtacatcatcccctgcagggccctggcctcacaaccacaga gtcccgccagcagcccatggccctggctgtggccctgaccaagggtggagaggcccgaggggagctgttctgggacgatggagagag cctggaagtgctggagcgaggggcctacacacaggtcatcttcctggccaggaataacacgatcgtgaatgagctggtacgtgtgaccag tgagggagctggcctgcagctgcagaaggtgactgtcctgggcgtggccacggcgccccagcaggtcctctccaacggtgtccctgtctc caacttcacctacagccccgacaccaag-
gtcctggacatctgtgtctcgctgttgatgggagagcagtttctcgtcagctggtgttagtctaga gcttgctagcggccgc

Construct 1754

The GILTΔ2-7Δ32-40-GAA70-952 cassette below was cloned using the Asp718 and NotI sites of the cassette and vector pCEP4 to produce pCEP-GILTΔ2-7Δ32-40-GAA70-952 (Plasmid 1754). Restriction sites for cloning are in lowercase bold. The spacer amino acid sequence Gly, Ala, Pro (underlined sequence) separate the GAA gene and GILTΔ2-7Δ32-40 tag (upper case sequence). The spacer and tag are placed upstream of GAA residue Ala70. The GILTΔ2-76, 32-40 cassette contains a deletion of amino acid residues 32-40 (Ala-Ser-Arg-Val-Ser-Arg-Arg-Ser-Arg) from the human IGF-II sequence.

(SEQ ID NO: 28)

ggtaccagctgctagcaagctaattcacaccaATGGGAATCCCAATGGGGAAGTCGATGCTGGTGCTTC

TCACCTTCTTGGCCTTCGCCTCGTGCTGCATTGCTGCTCTGTGCGGCGGGGAGCTGGT

GGACACCCTCCAGTTCGTCTGTGGGGACCGCGGCTrCTACTTCAGCAGGCCCGGCAT

CGTTGAGGAGTGCTGTTTCCGCAGCTGTGACCTGGCCCTCCTGGAGACGTACTGTGC

-continued

TACCCCCGCCAAGTCCGAGGGCGCGCCGgcacaccccggccgtcccagagcagtgcccacacagtgcgacgt ccccccaacagccgcttcgattgcgcccctgacaaggccatcacccaggaacagtgcgaggcccgcggctgctgctacatccctgcaa agcaggggctgcagggagcccagatggggcagccctggtgcttcttcccacccagctaccccagctacaagctggagaacctgagctcc tctgaaatgggctacacggccaccctgacccgtaccacccccaccttcttccccaaggacatcctgaccctgcggctggacgtgatgatgg agactgagaaccgcctccacttcacgatcaaagatccagctaacaggcgctacgaggtgcccttggagaccccgcgtgtccacagccgg gcaccgtccccactctacagcgtggagttctctgaggagcccttcggggtgatcgtgcaccggcagctggacggccgcgtgctgctgaac acgacggtggcgcccctgttctttgcggaccagttccttcagctgtccacctcgctgccctcgcagtatatcacaggcctcgccgagcacct cagtcccctgatgctcagcaccagctggaccaggatcaccctgtggaaccgggaccttgcgcccacgcccggtgcgaacctctacgggt ctcaccctttctacctggcgctggaggacggcgggtcggcacacggggtgttcctgctaaacagcaatgccatggatgtggtcctgcagcc gagccctgcccttagctggaggtcgacaggtgggatcctggatgtctacatcttcctgggcccagagcccaagagcgtggtgcagcagta cctggacgttgtgggatacccgttcatgccgccatactggggcctgggcaccacctgtgccgctggggctactcctccaccgctatcaccc gccaggtggtggagaacatgaccagggcccacttcccctggacgtccaatggaacgacctggactacatggactcccggagggacttc acgttcaacaaggatggcttccgggacttcccggccatggtgcaggagctgcaccagggcggccggcgctacatgatgatcgtggatcct gccatcagcagctcgggccctgccgggagctacaggccctacgacgagggtctgcggagggggttttcatcaccaacgagaccggcc agccgctgattgggaaggtatggcccgggtccactgccttccccgacttcaccaaccccacagccctggcctggtgggaggacatggtgg ctgagttccatgaccaggtgcccttcgacggcatgtggattgacatgaacgagccttccaacttcatcaggggctctgaggacggctgcccc aacaatgagctggagaacccaccctacgtgcctggggtggttgggggaccctccaggcggcaaccaaccatctgtgcctccagccaccagttt ctctccacacttctacaacctgcacaacctctacggcctgaccgaagccatcgcctcccacagggcgctggtgaaggctcgggggacacg cccatttgtgatctcccgctcgacctttgctggccacggccgatcgccggccactggacgggggacgtgtggagctcctgggagcagct cgcctcctccgtgccagaaatcctgcagtttaacctgctgggggtgcctctggtcggggccgacgtctgcggcttcctgggcaacacctca gaggagctgtgtgtgcgctggacccagctgggggccttctaccccncatgcggaaccacaacagcctgctcagtctgccccaggagccg tacagcttcagcgagccggcccagcaggccatgaggaaggccctcaccctgcgctacgcactcctcccccacctctacacgctgttccac caggcccacgtcgcgggggagaccgtggcccggcccctcttcctggagttccccaaggactctagcacctggactgtggaccaccagct cctgtgggggggaggccctgctcatcaccccagtgctccaggccgggaaggccgaagtgactggctacttccccttgggcacatggtacga cctgcagacggtgccaatagaggcccttggcagcctcccacccccacctgcagctccccgtgagccagccatccacagcgaggggcag tgggtgacgctgccggccccctggacaccatcaacgtccacctccgggctgggtacatcatcccctgcagggccctggcctcacaacc acagagtcccgccagcagcccatggccctggctgtggccctgaccaagggtggagaggcccgaggggagctgttctgggacgatgga gagagcctggaagtgctggagcgaggggcctacacacaggtcatcttcctggccaggaataacacgatcgtgaatgagctggtacgtgtg accagtgagggagctggcctgcagctgcagaaggtgactgtcctgggcgtggccacggcgccccagcaggtcctctccaacggtgtccc tgtctccaacttcacctacagccccgacaccaaggtcctggacatctgtgtctcgctgttgatgggagagcagtttctcgtcagctggtgttag tctagagcttgctagcggccgc

Construct 1755

The GILTΔ2-7Δ33-40-GAA70-952 cassette below was cloned using the Asp718 and NotI sites of the cassette and vector pCEP4 to produce pCEP-GILTΔ2-7Δ33-40-GAA70-952 (Plasmid 1755). Restriction sites for cloning are in lowercase bold. The spacer amino acid sequence Gly, Ala, Pro (underlined sequence) separate the GAA gene and GILTΔ2-7Δ33-40 tag (upper case sequence). The spacer and tag are placed upstream of GAA residue Ala70. The GILTΔ2-7Δ33-40 cassette contains a deletion of amino acid residues 33-40 (Ser-Arg-Val-Ser-Arg-Arg-Ser-Arg) from the human IGF-II sequence.

(SCQ ID NO: 29)

ggtaccagctgctagcaagctaattcacaccaATGGGAATCCCAATGGGGAAGTCGATGCTGGTGCTTC

TCACCTTCTTGGCCTTCGCCTCGTGCTGCATTGCTGCTCTGTGCGGCGGGGAGCTGGT

GGACACCCTCCAGTTCGTCTGTGGGGACCGCGGCTTCTACTTCAGCAGGCCCGCAGG

CATCGTTGAGGAGTGCTGTTTCCGCAGCTGTGACCTGGCCCTCCTGGAGACGTACTG

-continued

TGCTACCCCCGCCAAGTCCGAGGGCGCGCCGgcacaccccggccgtcccagagcagtgcccacacagtgc gacgtcccccccaacagccgcttcgattgcgcccctgacaaggccatcacccaggaacagtgcgaggcccgcggctgctgctacatccc tgcaaagcaggggctgcagggagcccagatggggcagccctggtgcttcttcccacccagctaccccagctacaagctggagaacctga gctcctctgaaatgggctacacggccaccctgacccgtaccacccccaccttcttccccaaggacatcctgaccctgcggctggacgtgat gatggagactgagaaccgcctccacttcacgatcaaagatccagctaacaggcgctacgaggtgcccttggagaccccgcgtgtccacag ccgggcaccgtccccactctacagcgtggagttctctgaggagcccttcggggtgatcgtgcacrggcagctggacggccgcgtgctgct gaacacgacggtggcgcccctgttctttgcgguccagttcctcagctgtccacctcgctgccctcgcagtatatcacaggcctcgccgagc acctcagtcccctgatgctcagcaccagctggaccaggatcaccctgtggaaccgggaccttgcgcccacgcccggtgcgaacctctacg ggtctcaccctttctacctggcgctggaggacggcgggtcggcacacggggtgttcctgctaaacagcaatgccatggatgtggtcctgca gccgagccctgcccttagctggaggtcgacaggtgggatcctggatgtctacatcncctgggcccagagcccaagagcgtggtgcagca gtacctggacgttgtgggatacccgt-
tcatgccgccatactggggcctgggcttccacctgtgccgctggggctactcctccaccgctatca cccgccaggtggtggagaacatgac-
cagggcccacrtccccctggacgtccaatggaacgacctggactacatggactggactcccggaggga cttcacgttcaacaaggatggcttccgggacttcccggccatggtgcaggagctgcaccagggcggccggcgctacatgatgatcgtgga tcctgccatcagcagctcgggccctgccgggagctacaggccctacgacgagggtctgcggagggggtttcatcaccaacgagaccg gccagccgctgangggaaggtatggcccgggtccactgccnccccgacttcaccaaccccacagccctggcctggtgggaggacatg gtggctgagttccatgaccaggtgccctcgacggcatgtggangacatgaacgagcctccaacttcatcaggggctctgaggacggctg ccccaacaatgagctggagaacccaccctacgtgcctggggtggttgggggaccctccaggcggcaaccatctgtgcctccagccacc agtttctctccacacactacaacctgcacaacctctacggcctgaccgaagccatcgcctcccacagggcgctggtgaaggctcgggga cacgcccamgtgatctcccgctcgaccatgctggccacggccgatacgccggccactggacgggggacgtgtggagctc agctcgcctcctccgtgccagaaatcctgcagtttaacctgctgggggtgcctctggtcggggccgacgtctgcggcttcctgggcaacac ctcagaggagctgtgtgtgcgctggacccagctgggggccttctaccccttcatgcggaaccacaacagcctgctcagtctgccccagga gccgtacagcttcagcgagccggcccagcaggccatgaggaaggccctcaccctgcgctacgcactcctcccccacctctacacgctgtt ccaccaggcccacgtcgcgggggagaccgtggcccggcccctcttcctggagwccccaaggactctagcacctggactgtggaccacc agctcctgtgggggaggccctgctcatcaccccagtgctccaggccgggaaggccgaagtgactggctacttccccttgggcacatggt acgacctgcagacggtgccaatagaggcccttggcagcctcccacccccacctgcagctccccgtgagccagccatccacagcgaggg gcagtgggtgacgctgccggccccctggacaccatcaacgtccacctccgggctgggtacatcatcccctgcagggccctggcctca caaccacagagtcccgccagcagcccatggccctggctgtggccctgaccaagggtggagaggcccgaggggagctgttctgggacg atggagagagcctggaagtgctggagcgaggggcctacacacaggtcatcttcctggccaggaataacacgatcgtgaatgagctggtac gtgtgaccagtgagggagctggcctgcagctgcagaaggtgactgtcctgggcgtggccacggcgccccagcaggtcctctccaacggt gtccctgtctccaacttcacctttcagc-
cccgacaccaatgtcctggacatctgtgtctcgctgttgatgggagagcagtactcgtcagctggt gttagtctagagcttgctagcggccgc

Construct 1756

The GILTΔ2-7Δ34-40-GAA70-952 cassette below was cloned using the Asp718 and NotI sites of the cassette and vector pCEP4 to produce pCEP-GILTΔ2-7Δ34-40-GAA70-952 (Plasmid 1756). Restriction sites for cloning are in lowercase bold. The spacer amino acid sequence Gly, Ala, Pro (underlined sequence) separate the GAA gene and GILTΔ2-7Δ34-40 tag (upper case sequence). The spacer and tag are placed upstream of GAA residue Ala70. The GILTΔ2-7Δ34-40 cassette contains a deletion of amino acid residues 34-40 (Arg-Val-Ser-Arg-Arg-Ser-Arg) from the human IGF-II sequence.

(SEQ ID NO: 30)

ggtaccagctgctagcaagctaattcacaccaATGGGAATCCCAATGGGGAAGTCGATGCTGGTGCTTC

TCACCTTCTTGGCCTTCGCCTCGTGCTGCATTGCTGCTCTGTGCGGCGGGGAGCTGGT

-continued

GGACACCCTCCAGTTCGTCTGTGGGGACCGCGGCTTCTACTTCAGCAGGCCCGCAAG

CGGCATCGTTGAGGAGTGCTGTTTCCGCAGCTGTGACCTGGCCCTCCTGGAGACGTA

CTGTCtCTACCCCCGCCAAGTCCGAGGGCGCGCCGacacaccccggccgtcccagagcagtgcccacaca gtgcgacgtcccccccaacagccgcttcgattgcgcccctgacaaggccatcacccaggaacagtgcgaggcccgcggctgctgctaca tccctgcaaagcaggggctgcagggagcccagatggggcagccctggtgcttcttcccacccagctaccccagctacaagctggagaac ctgagctcctctgaaatgggctacacggccaccctgacccgtaccacccccaccttcttccccaaggacatcctgaccctgcgtggacg tgatgatggagactgagaaccgcctccactttacgatcaaagatccagctaacaggcgctacgaggtgcccttggagaccccgcgtgtcc acagccgggcaccgtccccactctacagcgtggagttctctgaggagccctcggggtgatcgtgcaccggcagctggacggccgcgtg ctgctgaacacgacggtggcgcccctgttctttgcggaccagttccttcagctgtccacctcgctgccctcgcagtatatcacaggcctcgcc gagcacctcagtcccctgatgctcagcaccagctggaccaggatcaccctgtggaaccgggaccttgcgcccacgcccggtgcgaacct ctacgggtctcacccttctacctggcgctggaggacggcgggttggcacacggggtgttcctgctaaacagcaatgccatggatgtggtc ctgcagccgagccctgcccttagctggaggtcgacaggtgggatcctggatgtctacatcttcctgggcccagagcccaagagcgtggtg cagcagtacctggacgttgtgggatacccgttcatgccgcatactggggcctgggcttccacctgtgccgctggggctactcctccaccg ctatcacccgccaggtggtggagaacatgaccagggcccacttcccctggacgtccaatggaacgacctggactacatggactcccgga gggacttcacgttcaacaaggatggcttccgggacttcccggccatggtgcaggagctgcaccagggcggccggcgctacatgatgatc gtggatcctgccatcagcagctcgggccctgccgggagctacaggccctacgacgagggtctgcggagggggttttcatcaccaacga gaccggccagccgctgatgggaaggtatggcccgggtccactgccttccccgacttcaccaaccccacagccctggcctggtgggagg acatggtggctgagttccagaccaggtgcccttcgacggcatgtggatgacatgaacgagccnccaacttcatcaggggctctgaggac ggctgccccaacaatgagctggagaacccaccctacgtgcctggggtggttgggggaccctccaggcggcaaccatctgtgcctccag ccaccagtttctctccacacactacaacctgcacaacctctacggcctgaccgaagccatcgcctcccacagggcgctggtgaaggctcgg gggacacgcccatttgtgatctcccgctcgacctttgctggccacggccgatacgccggccactggacgggggacgtgtggagctcctgg gagcagctcgcctcctccgtgccagaaatcctgcagtttaacctgctgggggtgcctctggtcggggccgacgtctgcggcttcctgggca acacctcagaggagctgtgtgtgcgctggacccagctgggggccttctaccccttcatgcggaaccacaacagcctgctcagtctgcccca g+agccgtacagctcagcgagccggcccagcaggccatgaggaaggccctcaccctgcgctacgcactcctcccccacctctacacgc Ignccaccaggcccacgtcgcgggggagaccgtggcccggcccctcttcctggagnccccaaggactctagcacctggactgtggacc accagctcctgtgggggaggccctgctcatcaccccagtgctccaggccgggaaggccgaagtgactggctacttccccttgggcacat ggtacgacctgcagacggtgccaatagaggcccttggcagcctcccacccccacctgcagctccccgtgagccagccatccacagcgag gggcagtgggtgacgctgccggccccctggacaccatcaacgtccacctCcgggctgggtacatcatcccccctaagggccctggcct cacaaccacagagtcccgccagcagcccatggccctggctgtggcctgaccaagggtggagaggcccgaggggagctgttctgggac gatggagagagcctggaagtgctggagcgaggggcctacacacaggtcatcttcctggccaggaataacacgatcgtgaatgagctggt acgtgtgaccagtgagggagctggcctgcagctgcagaaggtgactgtcctgggcgtggccacggcgccccagcaggtcctaccaacg gtgtccctgtctccaacttcacctacagccccgacaccaaggtcctggacatctgtgtctcgctgttgatgggagagcagtttctcgtcagctg gtgttagtctagagcttgctagcggccgc

Construct 1763

The GILTΔ2-7M1/L27A37-GAA70-952 cassette below was cloned using the Asp718 and NotI sites of the cassette and vector pCEP4 to produce pCEP-GILTΔ2-7M1/L27A37-GAA70-952 (Plasmid 1763). Restriction sites for cloning are in lowercase bold. The spacer amino acid sequence Gly, Ala, Pro (underlined sequence) separate the GAA gene and GILTΔ2-7M1/L27A37 tag (upper case sequence). The spacer and tag are placed upstream of GAA residue Ala70. The GILTΔ2-7M1/L27A37 cassette contains Y27L and R37A substitutions in the human IGFII sequence. The DNA sequence of the GILT cassette differs from the human DNA sequence at every $6^{th}$ codon.

(SEQ ID NO: 31)

ggtaccaagcttgccATGGGAATCCCAATGGGCAAGTCGATGCTGGTGCTGCTCACCTTCTT

GGCCTTTGCCTCGTGCTGCATTGCCGCTCTGTGCGGCGGGGAACTGGTGGACACCCT

-continued

```
CCAATTCGTCTGTGGGGACCGGGGCTTCCTGTTCAGCAGACCCGCAAGCCGTGTGAG
TGCTCGCAGCCGTGGCATTGTTGAGGAGTGCTGTTTTCGCAGCTGTGACCTGGCTCT
CCTGGAGACGTACTGCGCTACCCCCGCCAAGTCTGAGGGCGCGCCGgcacaccccggccgtc
ccagagcagtgcccacacagtgcgacgtcccccccaacagccgcttcgattgcgcccctgacaaggccatcacccaggaacagtgcga
ggcccgcggctgctgctacatccctgcaaagcaggggctgcagggagcccagatggggcagccctggtgcttcttcccacccagctacc
ccagctacaagctggagaacctgagctcctctgaaatgggctacacggccaccctgacccgtaccacccccaccttcttccccaaggacat
cctgaccctgcggctggacgtgatgatggagactgagaaccgcctccacttcacgatcaaagatccagctaacaggcgctacgaggtgcc
caggagaccccgcgtgtccacagccgggcaccgtccccactctacagcgtggagactctgaggagccatcggggtgatcgtgcaccg
gcagctggacggccgcgtgctgctgaacacgacggtggcgcccctgttctttgcggaccagttccttcagctgtccacctcgctgccctcg
cagtatatcacaggcctcgccgagcacctcagtcccctgatgctcagcaccagctggaccaggatcaccctgtggaaccgggaccagcg
cccacgcccggtgcgaacctctacgggtctcaccctttctacctggcgctggaggacggcgggtcggcacacggggtgttcctgctaaac
agcaatgccatggatgtggtcctgcagccgagccctgcccttagctggaggtcgacaggtgggatcctggatgtctacatcacctgggccc
agagcccaagagcgtggtgcagcagtacctggacgttgtgggatacccgttcatgccgccatactggggcctgggatccacctgtgccg
ctggggctactcctccaccgctatcacccgccaggtggtggagaacatgaccagggcccacttcccccctggacgtccaatggaacgacct
ggactacatggactcccggagggacttcacgttcaacaaggatggatccgggacttcccggccatggtgcaggagctgcaccagggcg
gccggcgctacatgatgatcgtggatcctgccatcagcagctcgggccctgccgggagctacaggccctacgacgagggtctgcggagg
ggggttttcatcaccaacgagaccggccagccgctgattgggaaggtatggcccgggtccactgccttccccgacttcaccaaccccaca
gccctggcctggtgggaggacatggtggctgagttccatgaccaggtgcccttcgacggcatgtggattgacatgaacgagccaccaact
tcatcaggggctctgaggacggctgccccaacaatgagctggagaacccaccctacgtgcctggggtggttgggggaccctccaggcg
gcaaccatctgtgcctccagccaccagtttctaccaacacacaacctgcacaacctctacggcctgaccgaagccatcgcctcccacag
ggcgctggtgaaggctcgggggacazgcccatttgtgatctcccgctcgacctttgctggccacggccgatacgccggccactggacgg
gggacgtgtggagctcctgggagcagctcgcctcctccgtgccagaaatcctgcagtttaacctgctgggggtgcctctggtcggggccg
acgtctgcggcttcctgggcaacacctcagaggagctgtgtgtgcgctggacccagctgggggccttctaccccttcatgcggaaccacaa
cagcctgctcagtctgccccaggagccgtacagcttcagcgagccggcccagcaggccatgaggaaggccctcaccctgcgctacgca
ctcctcccccacctctacacgctgttccaccaggcccacgtcgcgggggagaccgtggcccggcccctcttcctggagttccccaaggact
ctagcacctggactgtggaccaccagctcctgtgggggaggccctgctcatcaccccagtgctccaggccgggaaggccgaagtgact
ggctacttccccttgggcacatggtacgacctgcagacggtgccaatagaggcccttggcagcctcccacccccacctgcagctccccgt
gagccagccatccacagcgaggggcagtgggtgacgctgccggccccctggacaccatcaacgtccacctccgggctgggtacatca
tcccccctgcagggccctggcctcacaaccacagagtcccgccagcagcccatggccctggctgtggccctgaccaagggtggagaggc
ccgaggggagctgttctgggacgatggagagagcctggaagtgctggagcgagggscctacacacaggtcatcttcctggccaggaata
acacgatcgtgaatgagctggtacgtgtgaccagtgagggagctggcctgcagctgcagaaggtgactgtcctgggcgtggccacggcg
ccccagcaggtcctctccaacggtgtccctgtctccaacttcacctacagccccgacaccaaggtcctggacatctgtgttctcgctgttgatg
ggagagcagtttctcgtcagctggtgttagtctagagcttgctagcggccgc
```

Example 3

Expression and Purification of GILT-tagged GAA enzymes

Tissue Culture

GILT-tagged GAA plasmids were each transfected into suspension FreeStyle 293-F cells as described by the manufacturer (Invitrogen). Briefly, cells were grown in Opti-MEM I media (Invitrogen) in polycarbonate shaker flasks on an orbital shaker at 37° C. and 8% $CO_2$. Cells were adjusted to a concentration of $1\times10^6$ cells/ml, then transfected with a 1:1:1 ratio of ml cells:μg DNA:μl 293fectin. Culture aliquots were harvested 5-7 days post-transfection and centrifuged at 5,000×g for 5 minutes. Supernatants were stored frozen at −80° C.

Protein Purification and Concentration

Starting material was mammalian cell culture supernatant, as described above, thawed from storage at −80° C. Citric acid was added to reach pH 6.0, then ammonium sulfate was added to reach a final concentration of 1M. The material was passed through a 0.2 μm Supor-Mach filter (Nalgene).

The filtered material was loaded onto a Phenyl-Sepharose 6 Low-Sub Fast-Flow (GE Healthcare) column prepared with HIC Load Buffer (50 mM citrate pH 6.0, 1M $AmSO_4$). The column was washed with 10 column volumes of HIC Wash Buffer (50 mM citrate pH 6.0, 0.8M $AmSO_4$), and eluted with 5 column volumes of HIC Elution Buffer (50 mM citrate pH 6.0). Samples from the elution peaks were pooled and bugger was exchanged into phosphate buffered saline (145.15 mM NaCl, 2.33 mM KCl, 10 mM $Na_2HPO_4$, 2 mM $KH_2PO_4$, pH 6.2) using centricon spin concentrators (Amicon) and Bio-Spin-6 de-salting columns (Bio-Rad).

Enzyme Activity

GAA expression was determined by a para-nitrophenol (PNP) enzymatic assay. GAA enzyme was incubated in 50 μl reaction mixture containing 100 mM sodium acetate pH 4.2 and 10 mM Para-Nitrophenol (PNP) α-glucoside substrate (Sigma N1377). Reactions were incubated at 37° C. for 20 minutes and stopped with 300 μl of 100 mM sodium carbonate. Absorbance at 405 nm was measured in 96-well microtiter plates and compared to standard curves derived from p-nitrophenol (Sigma N7660). 1 GAA PNP unit is defined as 1 nmole PNP hydrolyzed/hour.

Example 4

Competitive Receptor Binding Assays

The affinity of GILT-tagged proteins for the IGF2 receptor (IGF2R), IGF1 receptor (IGF1R) and the insulin receptor (IR) was examined in competitive binding experiments performed in a 96-well plate format. Receptors were coated at room temperature overnight onto Reacti-bind white plates (Pierce, Cat#437111) in Coating Buffer (0.05M Carbonate buffer, pH 9.6) at a concentration of either 0.5 μg/well (IGF2R) or 1 μg/well (IGF1R, IR). Plates were washed with wash buffer (Phosphate Buffered Saline plus 0.05% Tween-20), then blocked in Super Blocking Buffer (Pierce, Cat#37516) for 1 hour. After another plate washing, biotinylated ligands (Cell Sciences) were added to wells; IGF2R wells received 8 nM IGF2-biotin, IGF1R wells received 30 nM IGF1-biotin, and IR wells received 20 nM insulin-biotin. Along with the biotinylated ligands, wells also contained serial dilutions of the GILT-tagged GAA protein samples or non-biotinylated control ligands to act as binding inhibitors for the biotinylated ligands. Following a two-hour rocking incubation, plates were washed and bound biotinylated ligands were detected with a streptavidin-HRP incubation (R&D, Cat#890803, 1:200 dilution in blocking buffer, 30 minutes), followed by a Super Elisa Pico Chemiluminescent Substrate incubation (Pierce, Cat#7070, 5 minutes). The chemiluminescent signal was measured at 425 nm.

Figure 4:
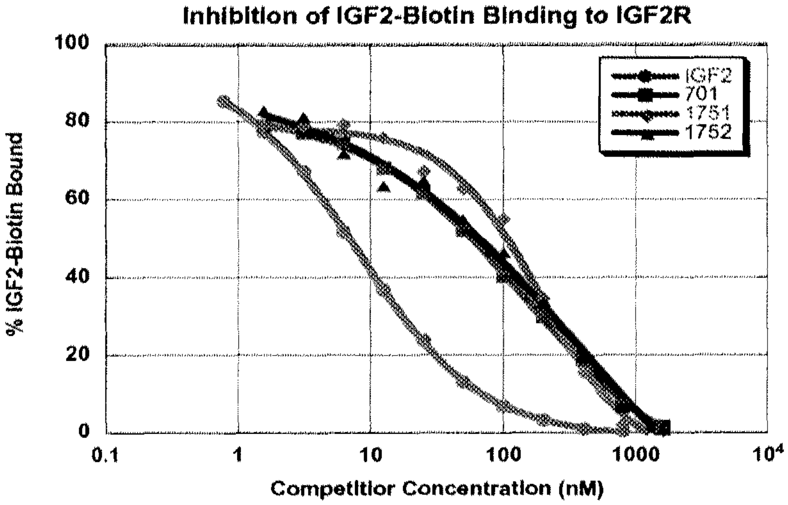
FIG. 4 illustrates exemplary competitive IGF-II receptor binding results.

The percent bound biotinylated ligand was calculated for each competitor concentration in the IGF2R binding competition assay and the $IC_{50}$ values were determined (FIG. 4). Protein 1752 with a deletion of IGF2 residues 30-40 displayed a similar $IC_{50}$ value as the GILT-tagged ZC-701 (FIG. 4), indicating that deletion of these residues in the IGF2 loop region does not appear to effect IGF2R binding. Protein 1751 with a deletion of IGF2 residues 29-40 displayed a higher $IC_{50}$ value (FIG. 4), indicating that it does not compete as well for binding to the IGF2R.

Figure 5:
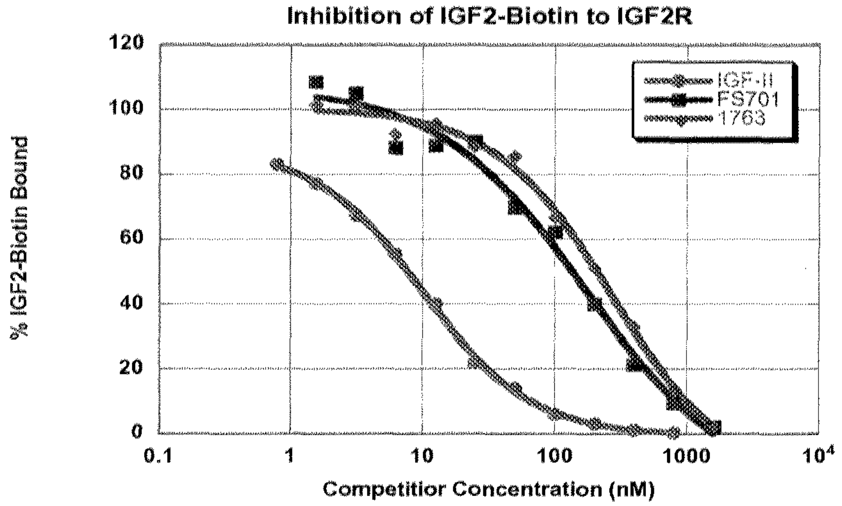
FIG. 5 illustrates additional exemplary competitive IGF-II receptor binding results.

On a separate IGF2R assay plate, comparison of ZC-701 and protein 1763 yielded $IC_{50}$ values that differed by 35% (See FIG. 5).

Figure 6:
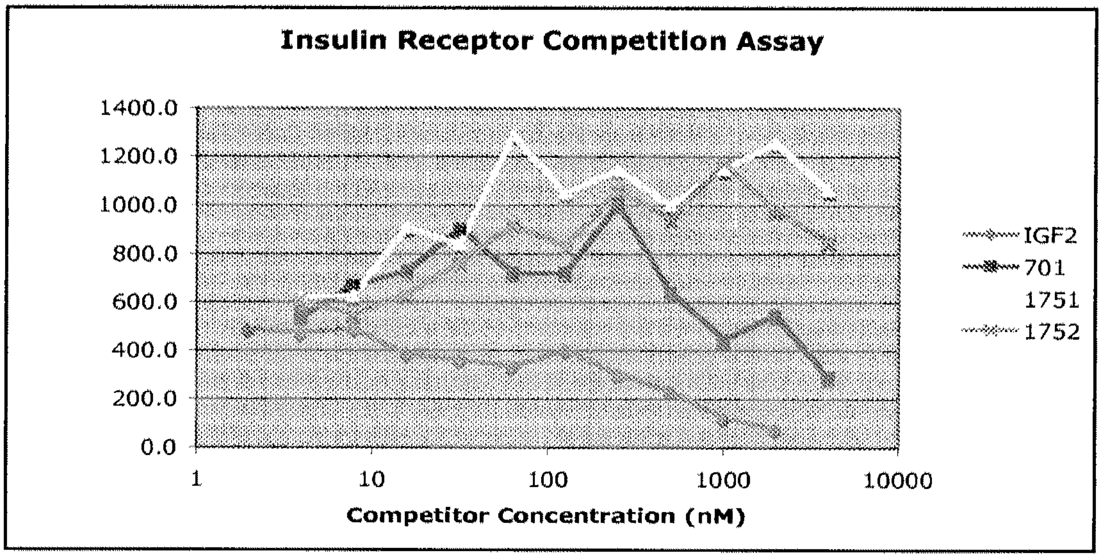
FIG. 6 illustrates exemplary insulin receptor competition assay results.

In an assay measuring the competition of biotinylated insulin binding to plate-bound insulin, 1751 and 1752 proteins were not as effective as inhibitors compared to 701 or IGF-II (See FIG. 6). This indicates that the 1751 and 1752 proteins, with deletions in the loop region corresponding to amino acids 30-40 of the GILT tag, had a reduced affinity for the insulin receptor compared to the intact GILT tag on 701 or IGF-II.

Figure 7:
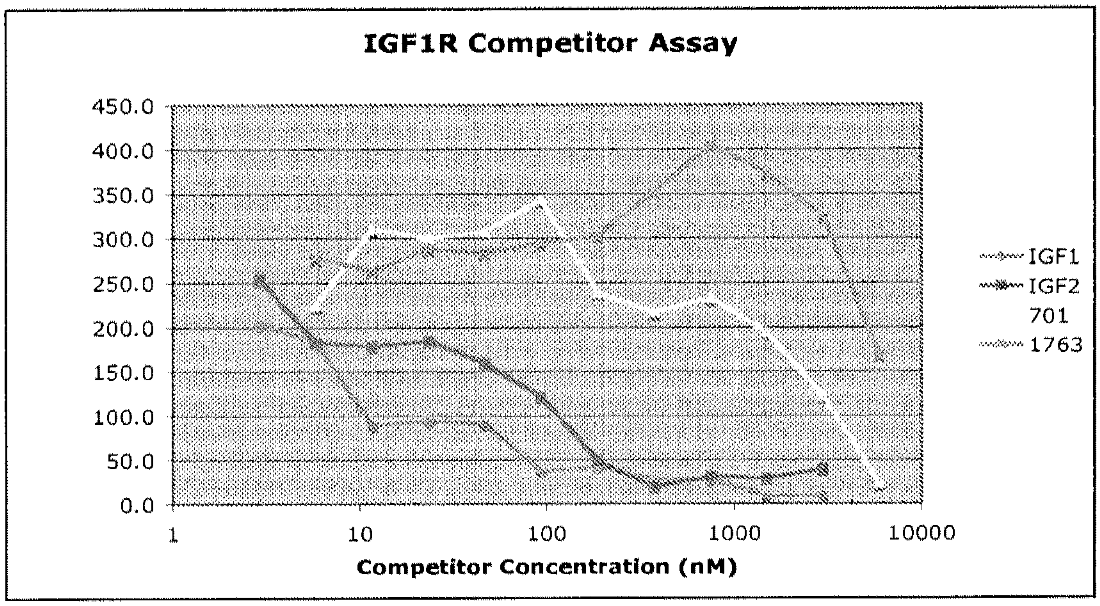
FIG. 7 illustrates exemplary IGF-I receptor competition assay results.

In an assay measuring the competition of biotinylated IGF-I binding to plate-bound IGF IR, 1763 protein was not as effective as an inhibitor compared to 701, IGF-II or IGF-I (See FIG. 7). This indicates that the 1763 protein, with Δ2-7. Y27L and R37A mutations in the GILT tag, had a reduced affinity for the IGF1 receptor compared to ZC-701 or IGF-II.

Example 4

Additional Insulin Receptor Binding Assay

Protein ZC-1487 was tested for its binding affinity for the insulin receptor. Protein ZC-1487 contains the GILTD2-7M1/A37 cassette contains with and Arg to Ala substitution at amino acid 37 of the human IGF2 sequence and is resistant to proteolysis by furin. Two different batches of this protein purified from CHO cells, ZC-1487-B26 and ZC-1487-B28 were analyzed in an assay measuring the competition of biotinylated insulin binding to plate-bound insulin.

An insulin receptor binding assay was conducted by competing insulin, IGF-II, ZC710B20 and ZC1487B26 or ZC-1487-B28 with Biotinylated-insulin binding to the insulin receptor (Insulin-R).

Specifically, white Reucti-Bind™ plates were coated with Insulin-R at a concentration of 1 ug/well/100 ul (38.4 nM). The coated plates were incubate over night at room temperature, then washed 3× with washing buffer (300 ul/well). The plates were then blocked with blocking buffer (300 ul/well) for 1 hour. The washing steps were repeated and any trace of solution in the plates was taken out.

Figure 8:
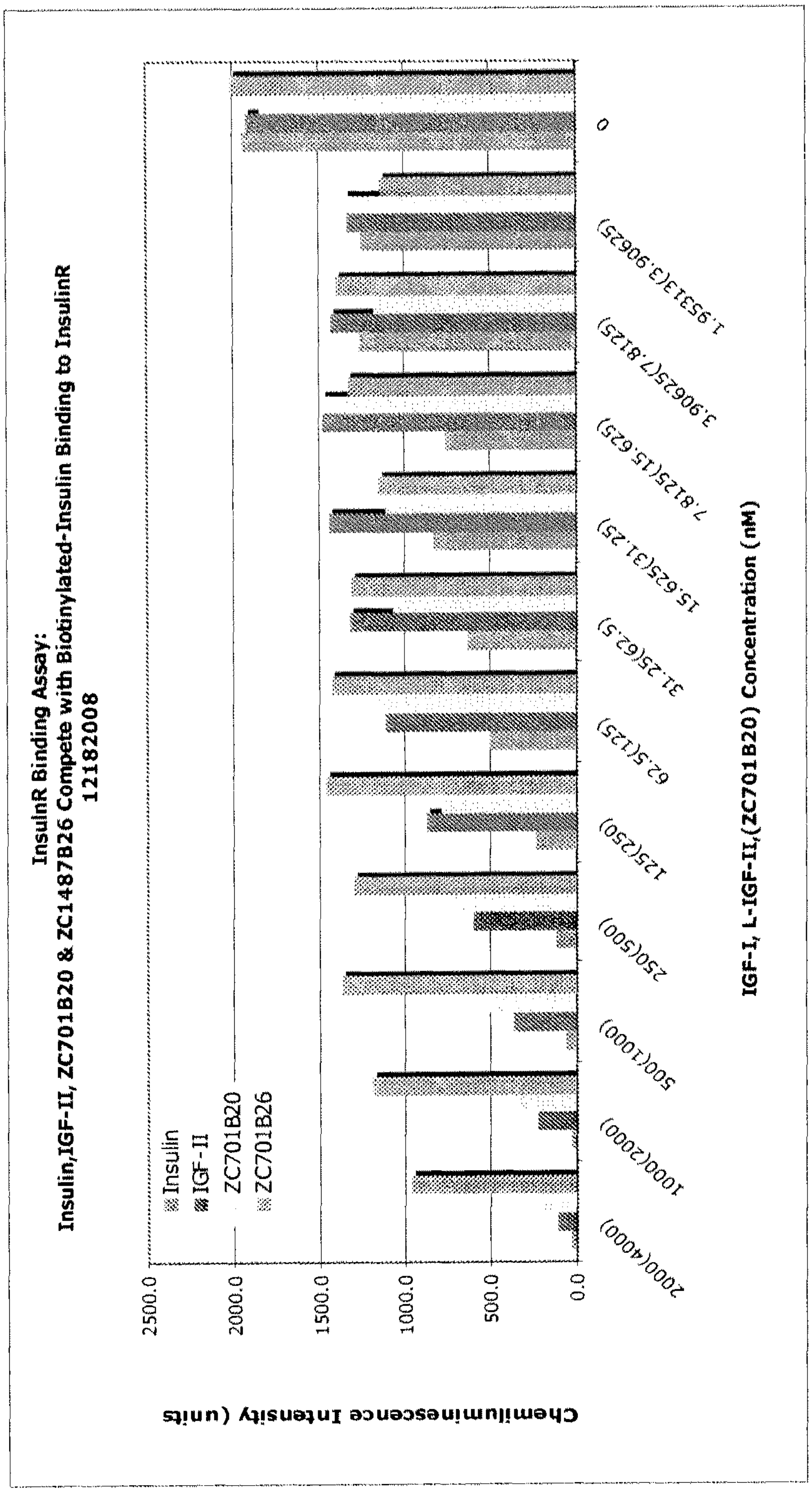
FIG. 8 illustrates exemplary results of certain insulin receptor binding assay.
Figure 9:
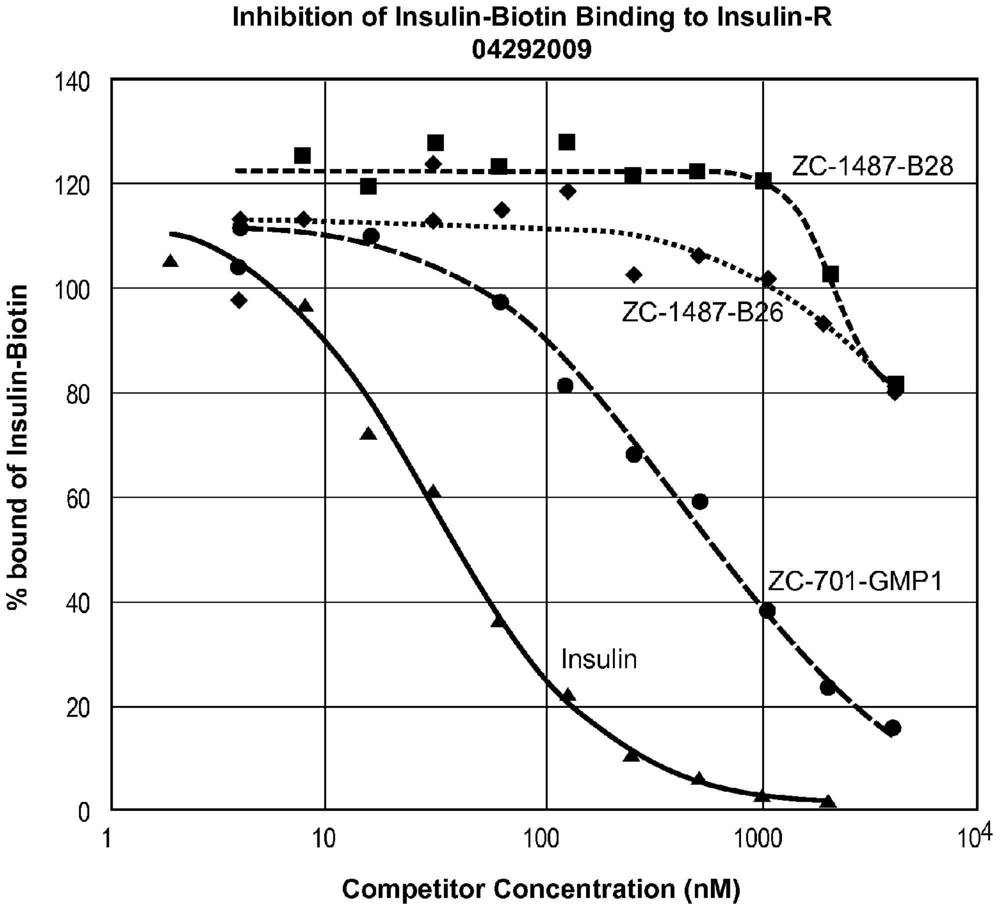
FIG. 9 illustrates exemplary results of certain insulin receptor binding assay.

Biotinylated-insulin was mixed at 20 nM with different concentrations of insulin, IGF-II, ZC701B20, B26 and B28 by serial dilutions (final concentrations are shown in Table 2). 100 ul of diluted Insulin, IGF-II, ZC710B20, ZC1487B26, and ZC1487B28 in 20 nM Insulin-biotin were added into the coated plates and the plates were incubated at room temperature for 2 hours. The plates were then washed 3 times with washing buffer. 100 ul of strepavidin-HRP working solution (50 ul strepavidin-HRP in 10 ml blocking buffer) was added into the plates and the plates were incubated at room temperature for 30 minutes. 100 ul of Elisa-Pico working solution containing Elisa-Pico chemiluminescent substrate was added and the chemiluminescence was measured at 425 nm. Exemplary results are shown in Table 2, FIG. 8, and FIG. 9. Both batches of ZC-1487 were not as effective as inhibitors compared to ZC-701 or the insulin control. As can be seen from Table 2 and FIG. 8, furin resistant peptide ZC-1487B26 binds to the insulin receptor more than 10-fold less avidly than does ZC-701 and more than 20-fold less than does the wild-type IGF-II This indicates that the 1487 protein had a reduced affinity for the insulin receptor compared to the GILT tag on ZC-701.

TABLE 2

| Insulin-Receptor Binding Activity - Chemiluminescence Intensity | | | | | | | | | | | | |
|---|---|---|---|---|---|---|---|---|---|---|---|---|
| Insulin-B (nM) | 2000 | 1000 | 500 | 250 | 125 | 62.5 | 31.25 | 15.625 | 7.8125 | 3.90625 | 1.95313 | 0 |
| | | | | | | Insulin (nM) | | | | | | |
| 20 nM | 38.00 | 43.00 | 66.00 | 102.00 | 243.00 | 479.00 | 750.00 | 780.00 | 503 | 1175 | 1046 | 2180 |
| 20 nM | 13.00 | 25.00 | 57.00 | 141.00 | 229.00 | 517.00 | 517.00 | 885.00 | 1003 | 1344 | 1462 | 1694 |
| ave | 25.5 | 34.0 | 61.5 | 121.5 | 236.0 | 498.0 | 633.5 | 832.5 | 753.0 | 1259.5 | 1254.0 | 1937.0 |
| | | | | | | IFG-II (nM) | | | | | | |
| 20 nM | 70.00 | 268.00 | 356.00 | 644.00 | 828.00 | 991.00 | 1189.00 | 1492.00 | 1478 | 1478 | 1410 | 1874 |
| 20 nM | 140.00 | 176.00 | 379.00 | 566.00 | 919.00 | 1224.00 | 1447.00 | 1377.00 | 1483 | 1370 | 1249 | 1959 |
| ave | 105.0 | 222.0 | 367.5 | 605.0 | 873.5 | 1107.5 | 1318.0 | 1434.5 | 1480.5 | 1424.0 | 1329.5 | 1916.5 |
| Insulin-B (nM) | 4000 | 2000 | 1000 | 500 | 250 | 125 | 62.5 | 31.25 | 15.625 | 7.8125 | 3.90625 | 0 |
| | | | | | | ZC701B20 (nM) | | | | | | |
| 20 nM | 191.00 | 387.00 | 526.00 | 715.00 | 800.00 | 1284.00 | 1116.00 | 1248.00 | 1474 | 1241 | 1450 | 1790 |
| 20 nM | 250.00 | 329.00 | 483.00 | 774.00 | 767.00 | 1071.00 | 1024.00 | 968.00 | 1471 | 1118 | 1234 | 1886 |
| ave | 220.5 | 358.0 | 504.5 | 744.5 | 783.5 | 1177.5 | 1070.0 | 1108.0 | 1472.5 | 1179.5 | 1342.0 | 1838.0 |
| | | | | | | ZC1487B26 (nM) | | | | | | |
| 20 nM | 967.00 | 1190.00 | 1334.00 | 1210.00 | 1294.00 | 1462.00 | 1402.00 | 1281.00 | 1323 | 1612 | 1173 | 1952 |
| 20 nM | 962.00 | 1189.00 | 1395.00 | 1379.00 | 1612.00 | 1396.00 | 1221.00 | 1013.00 | 1326 | 1182 | 1102 | 2069 |
| ave | 964.5 | 1189.5 | 1364.5 | 1294.5 | 1453.0 | 1429.0 | 1311.5 | 1147.0 | 1324.5 | 1397.0 | 1137.5 | 2010.5 |
| | 2000 (4000) | 1000 (2000) | 500 (1000) | 250 (500) | 125 (250) | 62.5 (125) | 31.25 (62.5) | 5.625 (31.25) | 7.8125 (15.625) | 3.90625 (7.8125) | 1.95313 (3.90625) | 0 |

Example 5

Uptake Assays

Some mutants were tested for retention of uptake activity. HEK293 cells ere transfected with constructs 1479 (R37K), 1487 (R37A) or ZC-701. After harvest, culture supernatants were partially purified by HIC chromatography. All samples were treated with PNGase prior to electrophoresis.

FIG. 10 shows partially purified preparations of targeted fusion proteins containing a furin-resistant IGF-II mutein tag analyzed by SDS-PAGE and immunoblotting. As can be seen, the fusion protein encoded by construct 1487 containing R37A mutation is resistant to exogenous furin.

FIG. 11 illustrates exemplary uptake results of furin resistant GILT-tagged GAA into rat L6 myoblasts. As shown in FIG. 11, exemplary $K_{uptakes}$ for proteins 1479, 1487, ZC-701, and purified ZC-701 are 4.5 nM, 4.4 nM, 5.0 nM and 2.6 nM, respectively, which indicates that the proteins encoded by constructs 1487 (R37A) and 1479 (R37K) retain the ability for efficient uptake into rat L6 myoblasts. The efficient uptake of fusion proteins containing a furin-resistant GILT tag also indicates that the furin-resistant tag retains high affinity for the CI-MPR.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. The articles "a", "an", and "the" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses variations, combinations, and permutations in which one or more limitations, elements, clauses, descriptive terms, etc., from one or more of the claims is introduced into another claim dependent on the same base claim (or, as relevant, any other claim) unless otherwise indicated or unless it would be evident to one of ordinary skill in the art that a contradiction or inconsistency would arise. Where elements are presented as lists, e.g., in Markush group or similar format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth herein. It should also be understood that any embodiment of the invention, e.g., any embodiment found within the prior art, can be explicitly excluded from the claims, regardless of whether the specific exclusion is recited in the specification.

It should also be understood that, unless clearly indicated to the contrary, in any methods claimed herein that include more than one act, the order of the acts of the method is not necessarily limited to the order in which the acts of the method are recited, but the invention includes embodiments in which the order is so limited. Furthermore, where the claims recite a composition, the invention encompasses methods of using the composition and methods of making the composition. Where the claims recite a composition, it should be understood that the invention encompasses methods of using the composition and methods of making the composition.

INCORPORATION OF REFERENCES

All publications and patent documents cited in this application are incorporated by reference in their entirety to the same extent as if the contents of each individual publication or patent document were incorporated herein.

What is claimed is:

1. A therapeutic fusion protein comprising an amino acid sequence at least 70% identical to wild type human α-N-acetylglucosaminidase (Naglu);

a lysosomal targeting moiety; and wherein, once administered, the therapeutic fusion protein is targeted to lysosomes and is therapeutically active in vivo, wherein the lysosomal targeting moiety is an IGF-II mutein comprising an amino acid sequence at least 70% identical to mature human IGF-II (SEQ ID NO:1), with a mutation within a region corresponding to amino acids 30-40 of SEQ ID NO:1 such that said mutation abolishes at least one furin protease cleavage site, wherein said mutation comprises a deletion of amino acids 30-40 of SEQ ID NO:1 or an amino acid substitution at a position corresponding to Arg37 of SEQ ID NO: 1, and wherein the IGF-II mutein is (a) resistant to furin cleavage, (b) has diminished binding affinity for the insulin receptor relative to the affinity of naturally-occurring human IGF-II for the insulin receptor, and (c) binds to the human cation-independent mannose-6-phosphate receptor in a mannose-6-phosphate-independent manner.

2. The therapeutic fusion protein of claim 1, wherein the Naglu comprises an amino acid sequence at least 80% identical to wild-type human Naglu.

3. The therapeutic fusion protein of claim 1, wherein the fusion protein further comprises a linker between the Naglu and the lysosomal targeting moiety.

4. The therapeutic fusion protein of claim 3, wherein the linker comprises the amino acid sequence GAP (SEQ ID NO:4).

5. The therapeutic fusion protein of claim 1, wherein the lysosomal targeting moiety is fused directly or via a linker to the C-terminus of the Naglu.

6. The therapeutic fusion protein of claim 1, wherein said mutation comprises a deletion of amino acids 30-40 of SEQ ID NO:1.

7. The therapeutic fusion protein of claim 1, wherein said mutation comprises an amino acid substitution at a position corresponding to Arg37 of SEQ ID NO: 1.

8. The therapeutic fusion protein of claim 7, wherein said amino acid substitution is an Ala substitution.

9. A method of treating Sanfilippo B disease (MPS IIIB) comprising a step of administering intrathecally to a subject in need of treatment the therapeutic fusion protein of claim 1.

10. The method of claim 9, wherein the Naglu comprises an amino acid sequence at least 80% identical to wild-type human Naglu.

11. The method of claim 9, wherein the fusion protein further comprises a linker between the Naglu and the lysosomal targeting moiety.

12. The method of claim 11, wherein the linker comprises the amino acid sequence GAP (SEQ ID NO:4).

13. The method of claim 9, wherein the lysosomal targeting moiety is fused directly or via a linker to the C-terminus of the Naglu.

14. The method of claim 9, wherein the lysosomal targeting moiety is fused directly or via a linker to the N-terminus of the Naglu.

15. The method of claim 9, wherein the intrathecal administration results in reduced intensity, severity, or frequency, or delayed onset of at least one symptom or feature of MPS IIIB.

16. The method of claim 9, wherein the intrathecal administration takes place at an interval selected from once every two weeks, once every month, and once every two months.

17. The method of claim 9, wherein the intrathecal administration is used in conjunction with intravenous administration.

18. The method of claim 9, wherein the intrathecal administration is not used in conjunction with intravenous administration.

19. The method of claim 9, wherein said mutation comprises a deletion of amino acids 30-40 of SEQ ID NO:1.

20. The method of claim 9, wherein said mutation comprises an amino acid substitution at a position corresponding to Arg37 of SEQ ID NO: 1.

21. The method of claim 9, wherein said amino acid substitution is an Ala substitution.

* * * * *

SEQUENCE LISTING

```
<160> NUMBER OF SEQ ID NOS: 35

<210> SEQ ID NO 1
<211> LENGTH: 67
<212> TYPE: PRT
<213> ORGANISM: Homo sapiens

<400> SEQUENCE: 1

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
        35                  40                  45

Arg Ser Cys Asp Leu Ala Leu Leu Glu Thr Tyr Cys Ala Thr Pro Ala
    50                  55                  60

Lys Ser Glu
65


<210> SEQ ID NO 2
<211> LENGTH: 4
<212> TYPE: PRT
<213> ORGANISM: Artificial Sequence
<220> FEATURE:
<223> OTHER INFORMATION: Furin protease recognition sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 2

Arg Xaa Xaa Arg
1


<210> SEQ ID NO 3
<211> LENGTH: 6
<212> TYPE: PRT
<213> ORGANISM: Artificial Sequence
<220> FEATURE:
<223> OTHER INFORMATION: Furin protease recognition sequence
<220> FEATURE:
<221> NAME/KEY: MISC_FEATURE
<222> LOCATION: (1)..(1)
<223> OTHER INFORMATION: Xaa is Lys or Arg
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa is Lys or Arg

<400> SEQUENCE: 3

Xaa Xaa Xaa Xaa Xaa Arg
1               5


<210> SEQ ID NO 4
<211> LENGTH: 3
<212> TYPE: PRT
<213> ORGANISM: Artificial Sequence
<220> FEATURE:
<223> OTHER INFORMATION: synthetic linker sequence

<400> SEQUENCE: 4

Gly Ala Pro
```

-continued

1

<210> SEQ ID NO 5
<211> LENGTH: 6
<212> TYPE: PRT
<213> ORGANISM: Artificial Sequence
<220> FEATURE:
<223> OTHER INFORMATION: synthetic linker sequence

<400> SEQUENCE: 5

Gly Gly Gly Gly Gly Pro
1 5

<210> SEQ ID NO 6
<211> LENGTH: 8
<212> TYPE: PRT
<213> ORGANISM: Artificial Sequence
<220> FEATURE:
<223> OTHER INFORMATION: Furin cleavage site - p1463 A40

<400> SEQUENCE: 6

Arg Val Ser Arg Arg Ser Ala Gly
1 5

<210> SEQ ID NO 7
<211> LENGTH: 3
<212> TYPE: PRT
<213> ORGANISM: Artificial Sequence
<220> FEATURE:
<223> OTHER INFORMATION: synthetic linker sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa is Thr or Ser

<400> SEQUENCE: 7

Asn Xaa Xaa
1

<210> SEQ ID NO 8
<211> LENGTH: 948
<212> TYPE: PRT
<213> ORGANISM: Artificial Sequence
<220> FEATURE:
<223> OTHER INFORMATION: synthetic ZC-701 construct

<400> SEQUENCE: 8

Ala Ala Leu Cys Gly Gly Glu Leu Val Asp Thr Leu Gln Phe Val Cys
1 5 10 15

Gly Asp Arg Gly Phe Tyr Phe Ser Arg Pro Ala Ser Arg Val Ser Arg
20 25 30

Arg Ser Arg Gly Ile Val Glu Glu Cys Cys Phe Arg Ser Cys Asp Leu
35 40 45

Ala Leu Leu Glu Thr Tyr Cys Ala Thr Pro Ala Lys Ser Glu Gly Ala
50 55 60

Pro Ala His Pro Gly Arg Pro Arg Ala Val Pro Thr Gln Cys Asp Val
65 70 75 80

Pro Pro Asn Ser Arg Phe Asp Cys Ala Pro Asp Lys Ala Ile Thr Gln
85 90 95

Glu Gln Cys Glu Ala Arg Gly Cys Cys Tyr Ile Pro Ala Lys Gln Gly
100 105 110

-continued

```
Leu Gln Gly Ala Gln Met Gly Gln Pro Trp Cys Phe Phe Pro Pro Ser
        115                 120                 125

Tyr Pro Ser Tyr Lys Leu Glu Asn Leu Ser Ser Ser Glu Met Gly Tyr
    130                 135                 140

Thr Ala Thr Leu Thr Arg Thr Thr Pro Thr Phe Phe Pro Lys Asp Ile
145                 150                 155                 160

Leu Thr Leu Arg Leu Asp Val Met Met Glu Thr Glu Asn Arg Leu His
                165                 170                 175

Phe Thr Ile Lys Asp Pro Ala Asn Arg Arg Tyr Glu Val Pro Leu Glu
            180                 185                 190

Thr Pro Arg Val His Ser Arg Ala Pro Ser Pro Leu Tyr Ser Val Glu
        195                 200                 205

Phe Ser Glu Glu Pro Phe Gly Val Ile Val His Arg Gln Leu Asp Gly
    210                 215                 220

Arg Val Leu Leu Asn Thr Thr Val Ala Pro Leu Phe Phe Ala Asp Gln
225                 230                 235                 240

Phe Leu Gln Leu Ser Thr Ser Leu Pro Ser Gln Tyr Ile Thr Gly Leu
                245                 250                 255

Ala Glu His Leu Ser Pro Leu Met Leu Ser Thr Ser Trp Thr Arg Ile
            260                 265                 270

Thr Leu Trp Asn Arg Asp Leu Ala Pro Thr Pro Gly Ala Asn Leu Tyr
        275                 280                 285

Gly Ser His Pro Phe Tyr Leu Ala Leu Glu Asp Gly Gly Ser Ala His
    290                 295                 300

Gly Val Phe Leu Leu Asn Ser Asn Ala Met Asp Val Val Leu Gln Pro
305                 310                 315                 320

Ser Pro Ala Leu Ser Trp Arg Ser Thr Gly Gly Ile Leu Asp Val Tyr
                325                 330                 335

Ile Phe Leu Gly Pro Glu Pro Lys Ser Val Val Gln Gln Tyr Leu Asp
            340                 345                 350

Val Val Gly Tyr Pro Phe Met Pro Pro Tyr Trp Gly Leu Gly Phe His
        355                 360                 365

Leu Cys Arg Trp Gly Tyr Ser Ser Thr Ala Ile Thr Arg Gln Val Val
    370                 375                 380

Glu Asn Met Thr Arg Ala His Phe Pro Leu Asp Val Gln Trp Asn Asp
385                 390                 395                 400

Leu Asp Tyr Met Asp Ser Arg Arg Asp Phe Thr Phe Asn Lys Asp Gly
                405                 410                 415

Phe Arg Asp Phe Pro Ala Met Val Gln Glu Leu His Gln Gly Gly Arg
            420                 425                 430

Arg Tyr Met Met Ile Val Asp Pro Ala Ile Ser Ser Ser Gly Pro Ala
        435                 440                 445

Gly Ser Tyr Arg Pro Tyr Asp Glu Gly Leu Arg Arg Gly Val Phe Ile
    450                 455                 460

Thr Asn Glu Thr Gly Gln Pro Leu Ile Gly Lys Val Trp Pro Gly Ser
465                 470                 475                 480

Thr Ala Phe Pro Asp Phe Thr Asn Pro Thr Ala Leu Ala Trp Trp Glu
                485                 490                 495

Asp Met Val Ala Glu Phe His Asp Gln Val Pro Phe Asp Gly Met Trp
            500                 505                 510

Ile Asp Met Asn Glu Pro Ser Asn Phe Ile Arg Gly Ser Glu Asp Gly
        515                 520                 525

Cys Pro Asn Asn Glu Leu Glu Asn Pro Pro Tyr Val Pro Gly Val Val
    530                 535                 540
```

-continued

```
Gly Gly Thr Leu Gln Ala Ala Thr Ile Cys Ala Ser Ser His Gln Phe
545                 550                 555                 560

Leu Ser Thr His Tyr Asn Leu His Asn Leu Tyr Gly Leu Thr Glu Ala
                565                 570                 575

Ile Ala Ser His Arg Ala Leu Val Lys Ala Arg Gly Thr Arg Pro Phe
            580                 585                 590

Val Ile Ser Arg Ser Thr Phe Ala Gly His Gly Arg Tyr Ala Gly His
        595                 600                 605

Trp Thr Gly Asp Val Trp Ser Ser Trp Glu Gln Leu Ala Ser Ser Val
    610                 615                 620

Pro Glu Ile Leu Gln Phe Asn Leu Leu Gly Val Pro Leu Val Gly Ala
625                 630                 635                 640

Asp Val Cys Gly Phe Leu Gly Asn Thr Ser Glu Glu Leu Cys Val Arg
                645                 650                 655

Trp Thr Gln Leu Gly Ala Phe Tyr Pro Phe Met Arg Asn His Asn Ser
            660                 665                 670

Leu Leu Ser Leu Pro Gln Glu Pro Tyr Ser Phe Ser Glu Pro Ala Gln
        675                 680                 685

Gln Ala Met Arg Lys Ala Leu Thr Leu Arg Tyr Ala Leu Leu Pro His
    690                 695                 700

Leu Tyr Thr Leu Phe His Gln Ala His Val Ala Gly Glu Thr Val Ala
705                 710                 715                 720

Arg Pro Leu Phe Leu Glu Phe Pro Lys Asp Ser Ser Thr Trp Thr Val
                725                 730                 735

Asp His Gln Leu Leu Trp Gly Glu Ala Leu Leu Ile Thr Pro Val Leu
            740                 745                 750

Gln Ala Gly Lys Ala Glu Val Thr Gly Tyr Phe Pro Leu Gly Thr Trp
        755                 760                 765

Tyr Asp Leu Gln Thr Val Pro Ile Glu Ala Leu Gly Ser Leu Pro Pro
    770                 775                 780

Pro Pro Ala Ala Pro Arg Glu Pro Ala Ile His Ser Glu Gly Gln Trp
785                 790                 795                 800

Val Thr Leu Pro Ala Pro Leu Asp Thr Ile Asn Val His Leu Arg Ala
                805                 810                 815

Gly Tyr Ile Ile Pro Leu Gln Gly Pro Gly Leu Thr Thr Thr Glu Ser
            820                 825                 830

Arg Gln Gln Pro Met Ala Leu Ala Val Ala Leu Thr Lys Gly Gly Glu
        835                 840                 845

Ala Arg Gly Glu Leu Phe Trp Asp Asp Gly Glu Ser Leu Glu Val Leu
    850                 855                 860

Glu Arg Gly Ala Tyr Thr Gln Val Ile Phe Leu Ala Arg Asn Asn Thr
865                 870                 875                 880

Ile Val Asn Glu Leu Val Arg Val Thr Ser Glu Gly Ala Gly Leu Gln
                885                 890                 895

Leu Gln Lys Val Thr Val Leu Gly Val Ala Thr Ala Pro Gln Gln Val
            900                 905                 910

Leu Ser Asn Gly Val Pro Val Ser Asn Phe Thr Tyr Ser Pro Asp Thr
        915                 920                 925

Lys Val Leu Asp Ile Cys Val Ser Leu Leu Met Gly Glu Gln Phe Leu
    930                 935                 940

Val Ser Trp Cys
945
```

-continued

<210> SEQ ID NO 9
<211> LENGTH: 4
<212> TYPE: PRT
<213> ORGANISM: Artificial Sequence
<220> FEATURE:
<223> OTHER INFORMATION: sequence proximal to ZC-701 cleavage site

<400> SEQUENCE: 9

Arg Arg Ser Arg
1

<210> SEQ ID NO 10
<211> LENGTH: 4
<212> TYPE: PRT
<213> ORGANISM: Artificial Sequence
<220> FEATURE:
<223> OTHER INFORMATION: Furin protease recognition sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 10

Arg Xaa Xaa Arg
1

<210> SEQ ID NO 11
<211> LENGTH: 2970
<212> TYPE: DNA
<213> ORGANISM: Artificial Sequence
<220> FEATURE:
<223> OTHER INFORMATION: GILTd2-7-GAA70-952 cassette

<400> SEQUENCE: 11
ggtaccagct gctagcaagc taattcacac caatgggaat cccaatgggg aagtcgatgc 60
tggtgcttct caccttcttg gccttcgcct cgtgctgcat tgctgctctg tgcggcgggg 120
agctggtgga caccctccag ttcgtctgtg gggaccgcgg cttctacttc agcaggcccg 180
caagccgtgt gagccgtcgc agccgtggca tcgttgagga gtgctgtttc cgcagctgtg 240
acctggccct cctggagacg tactgtgcta cccccgccaa gtccgagggc gcgccggcac 300
accccggccg tcccagagca gtgcccacac agtgcgacgt cccccccaac agccgcttcg 360
attgcgcccc tgacaaggcc atcacccagg aacagtgcga ggcccgcggc tgctgctaca 420
tccctgcaaa gcaggggctg cagggagccc agatggggca gccctggtgc ttcttcccac 480
ccagctaccc cagctacaag ctggagaacc tgagctcctc tgaaatgggc tacacggcca 540
ccctgacccg taccaccccc accttcttcc ccaaggacat cctgaccctg cggctggacg 600
tgatgatgga gactgagaac cgcctccact tcacgatcaa agatccagct aacaggcgct 660
acgaggtgcc cttggagacc ccgcgtgtcc acagccgggc accgtcccca ctctacagcg 720
tggagttctc tgaggagccc ttcggggtga tcgtgcaccg gcagctggac ggccgcgtgc 780
tgctgaacac gacggtggcg cccctgttct ttgcggacca gttccttcag ctgtccacct 840
cgctgccctc gcagtatatc acaggcctcg ccgagcacct cagtcccctg atgctcagca 900
ccagctggac caggatcacc ctgtggaacc gggaccttgc gcccacgccc ggtgcgaacc 960
tctacgggtc tcaccctttc tacctggcgc tggaggacgg cgggtcggca cacggggtgt 1020
tcctgctaaa cagcaatgcc atggatgtgg tcctgcagcc gagccctgcc cttagctgga 1080
ggtcgacagg tgggatcctg gatgtctaca tcttcctggg cccagagccc aagagcgtgg 1140
tgcagcagta cctggacgtt gtgggatacc cgttcatgcc gccatactgg ggcctgggct 1200
tccacctgtg ccgctggggc tactcctcca ccgctatcac ccgccaggtg gtggagaaca 1260
tgaccagggc ccacttcccc ctggacgtcc aatggaacga cctggactac atggactccc 1320
ggagggactt cacgttcaac aaggatggct tccgggactt cccggccatg gtgcaggagc 1380
tgcaccaggg cggccggcgc tacatgatga tcgtggatcc tgccatcagc agctcgggcc 1440
ctgccgggag ctacaggccc tacgacgagg gtctgcggag gggggttttc atcaccaacg 1500
agaccggcca gccgctgatt gggaaggtat ggcccgggtc cactgccttc cccgacttca 1560
ccaaccccac agccctggcc tggtgggagg acatggtggc tgagttccat gaccaggtgc 1620
ccttcgacgg catgtggatt gacatgaacg agccttccaa cttcatcagg ggctctgagg 1680
acggctgccc caacaatgag ctggagaacc caccctacgt gcctggggtg gttgggggga 1740
ccctccaggc ggcaaccatc tgtgcctcca gccaccagtt tctctccaca cactacaacc 1800
tgcacaacct ctacggcctg accgaagcca tcgcctccca cagggcgctg gtgaaggctc 1860
gggggacacg cccatttgtg atctcccgct cgacctttgc tggccacggc cgatacgccg 1920
gccactggac gggggacgtg tggagctcct gggagcagct cgcctcctcc gtgccagaaa 1980
tcctgcagtt taacctgctg ggggtgcctc tggtcggggc cgacgtctgc ggcttcctgg 2040
gcaacacctc agaggagctg tgtgtgcgct ggacccagct gggggccttc taccccttca 2100
tgcggaacca caacagcctg ctcagtctgc cccaggagcc gtacagcttc agcgagccgg 2160
cccagcaggc catgaggaag gccctcaccc tgcgctacgc actcctcccc cacctctaca 2220
cgctgttcca ccaggcccac gtcgcggggg agaccgtggc ccggcccctc ttcctggagt 2280
tccccaagga ctctagcacc tggactgtgg accaccagct cctgtggggg gaggccctgc 2340
tcatcacccc agtgctccag gccgggaagg ccgaagtgac tggctacttc cccttgggca 2400
catggtacga cctgcagacg gtgccaatag aggcccttgg cagcctccca cccccacctg 2460
cagctccccg tgagccagcc atccacagcg aggggcagtg ggtgacgctg ccggcccccc 2520
tggacaccat caacgtccac ctccgggctg ggtacatcat ccccctgcag ggccctggcc 2580
tcacaaccac agagtcccgc cagcagccca tggccctggc tgtggccctg accaagggtg 2640
gagaggcccg aggggagctg ttctgggacg atggagagag cctggaagtg ctggagcgag 2700
gggcctacac acaggtcatc ttcctggcca ggaataacac gatcgtgaat gagctggtac 2760
gtgtgaccag tgagggagct ggcctgcagc tgcagaaggt gactgtcctg ggcgtggcca 2820
cggcgcccca gcaggtcctc tccaacggtg tccctgtctc caacttcacc tacagccccg 2880
acaccaaggt cctggacatc tgtgtctcgc tgttgatggg agagcagttt ctcgtcagct 2940
ggtgttagtc tagagcttgc tagcggccgc 2970

<210> SEQ ID NO 12
<211> LENGTH: 2970
<212> TYPE: DNA
<213> ORGANISM: Artificial Sequence
<220> FEATURE:
<223> OTHER INFORMATION: GILTd2-7/K37-GAA70-952 cassette

<400> SEQUENCE: 12
ggtaccagct gctagcaagc taattcacac caatgggaat cccaatgggg aagtcgatgc 60
tggtgcttct caccttcttg gccttcgcct cgtgctgcat tgctgctctg tgcggcgggg 120
agctggtgga caccctccag ttcgtctgtg gggaccgcgg cttctacttc agcaggcccg 180
caagccgtgt gagcaagcgc agccgtggca tcgttgagga gtgctgtttc cgcagctgtg 240
acctggccct cctggagacg tactgtgcta cccccgccaa gtccgagggc gcgccggcac 300
accccggccg tcccagagca gtgcccacac agtgcgacgt cccccccaac agccgcttcg 360

```
attgcgcccc tgacaaggcc atcacccagg aacagtgcga ggcccgcggc tgctgctaca    420
tccctgcaaa gcaggggctg cagggagccc agatggggca gccctggtgc ttcttcccac    480
ccagctaccc cagctacaag ctggagaacc tgagctcctc tgaaatgggc tacacggcca    540
ccctgacccg taccaccccc accttcttcc ccaaggacat cctgaccctg cggctggacg    600
tgatgatgga gactgagaac cgcctccact tcacgatcaa agatccagct aacaggcgct    660
acgaggtgcc cttggagacc ccgcgtgtcc acagccgggc accgtcccca ctctacagcg    720
tggagttctc tgaggagccc ttcggggtga tcgtgcaccg gcagctggac ggccgcgtgc    780
tgctgaacac gacggtggcg cccctgttct ttgcggacca gttccttcag ctgtccacct    840
cgctgccctc gcagtatatc acaggcctcg ccgagcacct cagtcccctg atgctcagca    900
ccagctggac caggatcacc ctgtggaacc gggaccttgc gcccacgccc ggtgcgaacc    960
tctacgggtc tcaccctttc tacctggcgc tggaggacgg cgggtcggca cacggggtgt   1020
tcctgctaaa cagcaatgcc atggatgtgg tcctgcagcc gagccctgcc cttagctgga   1080
ggtcgacagg tgggatcctg gatgtctaca tcttcctggg cccagagccc aagagcgtgg   1140
tgcagcagta cctggacgtt gtgggatacc cgttcatgcc gccatactgg ggcctgggct   1200
tccacctgtg ccgctggggc tactcctcca ccgctatcac ccgccaggtg gtggagaaca   1260
tgaccagggc ccacttcccc ctggacgtcc aatggaacga cctggactac atggactccc   1320
ggagggactt cacgttcaac aaggatggct tccgggactt cccggccatg gtgcaggagc   1380
tgcaccaggg cggccggcgc tacatgatga tcgtggatcc tgccatcagc agctcgggcc   1440
ctgccgggag ctacaggccc tacgacgagg gtctgcggag gggggttttc atcaccaacg   1500
agaccggcca gccgctgatt gggaaggtat ggcccgggtc cactgccttc cccgacttca   1560
ccaaccccac agccctggcc tggtgggagg acatggtggc tgagttccat gaccaggtgc   1620
ccttcgacgg catgtggatt gacatgaacg agccttccaa cttcatcagg ggctctgagg   1680
acggctgccc caacaatgag ctggagaacc caccctacgt gcctggggtg gttgggggga   1740
ccctccaggc ggcaaccatc tgtgcctcca gccaccagtt tctctccaca cactacaacc   1800
tgcacaacct ctacggcctg accgaagcca tcgcctccca cagggcgctg gtgaaggctc   1860
gggggacacg cccatttgtg atctcccgct cgacctttgc tggccacggc cgatacgccg   1920
gccactggac gggggacgtg tggagctcct gggagcagct cgcctcctcc gtgccagaaa   1980
tcctgcagtt taacctgctg ggggtgcctc tggtcggggc cgacgtctgc ggcttcctgg   2040
gcaacacctc agaggagctg tgtgtgcgct ggacccagct gggggccttc taccccttca   2100
tgcggaacca caacagcctg ctcagtctgc cccaggagcc gtacagcttc agcgagccgg   2160
cccagcaggc catgaggaag gccctcaccc tgcgctacgc actcctcccc cacctctaca   2220
cgctgttcca ccaggcccac gtcgcggggg agaccgtggc ccggcccctc ttcctggagt   2280
tccccaagga ctctagcacc tggactgtgg accaccagct cctgtggggg gaggccctgc   2340
tcatcacccc agtgctccag gccgggaagg ccgaagtgac tggctacttc cccttgggca   2400
catggtacga cctgcagacg gtgccaatag aggcccttgg cagcctccca cccccacctg   2460
cagctccccg tgagccagcc atccacagcg aggggcagtg ggtgacgctg ccggcccccc   2520
tggacaccat caacgtccac ctccgggctg ggtacatcat cccccctgcag ggccctggcc  2580
tcacaaccac agagtcccgc cagcagccca tggccctggc tgtggccctg accaagggtg   2640
gagaggcccg aggggagctg ttctgggacg atggagagag cctggaagtg ctggagcgag   2700
gggcctacac acaggtcatc ttcctggcca ggaataacac gatcgtgaat gagctggtac   2760
```

gtgtgaccag tgagggagct ggcctgcagc tgcagaaggt gactgtcctg ggcgtggcca 2820
cggcgcccca gcaggtcctc tccaacggtg tccctgtctc caacttcacc tacagccccg 2880
acaccaaggt cctggacatc tgtgtctcgc tgttgatggg agagcagttt ctcgtcagct 2940
ggtgttagtc tagagcttgc tagcggccgc 2970

<210> SEQ ID NO 13
<211> LENGTH: 2970
<212> TYPE: DNA
<213> ORGANISM: Artificial Sequence
<220> FEATURE:
<223> OTHER INFORMATION: GILTd2-7/K40-GAA70-952 cassette

<400> SEQUENCE: 13
ggtaccagct gctagcaagc taattcacac caatgggaat cccaatgggg aagtcgatgc 60
tggtgcttct caccttcttg gccttcgcct cgtgctgcat tgctgctctg tgcggcgggg 120
agctggtgga caccctccag ttcgtctgtg gggaccgcgg cttctacttc agcaggcccg 180
caagccgtgt gagccgtcgc agcaagggca tcgttgagga gtgctgtttc cgcagctgtg 240
acctggccct cctggagacg tactgtgcta cccccgccaa gtccgagggc gcgccggcac 300
accccggccg tcccagagca gtgcccacac agtgcgacgt cccccccaac agccgcttcg 360
attgcgcccc tgacaaggcc atcacccagg aacagtgcga ggcccgcggc tgctgctaca 420
tccctgcaaa gcaggggctg cagggagccc agatggggca gccctggtgc ttcttcccac 480
ccagctaccc cagctacaag ctggagaacc tgagctcctc tgaaatgggc tacacggcca 540
ccctgacccg taccaccccc accttcttcc ccaaggacat cctgaccctg cggctggacg 600
tgatgatgga gactgagaac cgcctccact tcacgatcaa agatccagct aacaggcgct 660
acgaggtgcc cttggagacc ccgcgtgtcc acagccgggc accgtcccca ctctacagcg 720
tggagttctc tgaggagccc ttcggggtga tcgtgcaccg gcagctggac ggccgcgtgc 780
tgctgaacac gacggtggcg cccctgttct ttgcggacca gttccttcag ctgtccacct 840
cgctgccctc gcagtatatc acaggcctcg ccgagcacct cagtcccctg atgctcagca 900
ccagctggac caggatcacc ctgtggaacc gggaccttgc gcccacgccc ggtgcgaacc 960
tctacgggtc tcaccctttc tacctggcgc tggaggacgg cgggtcggca cacggggtgt 1020
tcctgctaaa cagcaatgcc atggatgtgg tcctgcagcc gagccctgcc cttagctgga 1080
ggtcgacagg tgggatcctg gatgtctaca tcttcctggg cccagagccc aagagcgtgg 1140
tgcagcagta cctggacgtt gtgggatacc cgttcatgcc gccatactgg ggcctgggct 1200
tccacctgtg ccgctggggc tactcctcca ccgctatcac ccgccaggtg gtggagaaca 1260
tgaccagggc ccacttcccc ctggacgtcc aatggaacga cctggactac atggactccc 1320
ggagggactt cacgttcaac aaggatggct tccgggactt cccggccatg gtgcaggagc 1380
tgcaccaggg cggccggcgc tacatgatga tcgtggatcc tgccatcagc agctcgggcc 1440
ctgccgggag ctacaggccc tacgacgagg gtctgcggag gggggttttc atcaccaacg 1500
agaccggcca gccgctgatt gggaaggtat ggcccgggtc cactgccttc cccgacttca 1560
ccaaccccac agccctggcc tggtgggagg acatggtggc tgagttccat gaccaggtgc 1620
ccttcgacgg catgtggatt gacatgaacg agccttccaa cttcatcagg ggctctgagg 1680
acggctgccc caacaatgag ctggagaacc caccctacgt gcctggggtg gttgggggga 1740
ccctccaggc ggcaaccatc tgtgcctcca gccaccagtt tctctccaca cactacaacc 1800
tgcacaacct ctacggcctg accgaagcca tcgcctccca cagggcgctg gtgaaggctc 1860
gggggacacg cccatttgtg atctcccgct cgacctttgc tggccacggc cgatacgccg 1920
gccactggac gggggacgtg tggagctcct gggagcagct cgcctcctcc gtgccagaaa 1980
tcctgcagtt taacctgctg gggtgcctc tggtcggggc cgacgtctgc ggcttcctgg 2040
gcaacacctc agaggagctg tgtgtgcgct ggacccagct gggggccttc taccccttca 2100
tgcggaacca caacagcctg ctcagtctgc cccaggagcc gtacagcttc agcgagccgg 2160
cccagcaggc catgaggaag gccctcaccc tgcgctacgc actcctcccc cacctctaca 2220
cgctgttcca ccaggcccac gtcgcggggg agaccgtggc ccggcccctc ttcctggagt 2280
tccccaagga ctctagcacc tggactgtgg accaccagct cctgtggggg gaggccctgc 2340
tcatcacccc agtgctccag gccgggaagg ccgaagtgac tggctacttc cccttgggca 2400
catggtacga cctgcagacg gtgccaatag aggcccttgg cagcctccca cccccacctg 2460
cagctccccg tgagccagcc atccacagcg aggggcagtg ggtgacgctg ccggcccccc 2520
tggacaccat caacgtccac ctccgggctg ggtacatcat cccctgcag ggccctggcc 2580 tcacaaccac agagtcccgc cagcagccca tggccctggc tgtggccctg accaagggtg 2640
gagaggcccg aggggagctg ttctgggacg atggagagag cctggaagtg ctggagcgag 2700
gggcctacac acaggtcatc ttcctggcca ggaataacac gatcgtgaat gagctggtac 2760
gtgtgaccag tgagggagct ggcctgcagc tgcagaaggt gactgtcctg ggcgtggcca 2820
cggcgcccca gcaggtcctc tccaacggtg tccctgtctc caacttcacc tacagccccg 2880
acaccaaggt cctggacatc tgtgtctcgc tgttgatggg agagcagttt ctcgtcagct 2940
ggtgttagtc tagagcttgc tagcggccgc 2970

<210> SEQ ID NO 14
<211> LENGTH: 2970
<212> TYPE: DNA
<213> ORGANISM: Artificial Sequence
<220> FEATURE:
<223> OTHER INFORMATION: GILTd2-7/A37-GAA70-952 cassette

<400> SEQUENCE: 14
ggtaccagct gctagcaagc taattcacac caatgggaat cccaatgggg aagtcgatgc 60
tggtgcttct caccttcttg gccttcgcct cgtgctgcat tgctgctctg tgcggcgggg 120
agctggtgga caccctccag ttcgtctgtg gggaccgcgg cttctacttc agcaggcccg 180
caagccgtgt gagcgctcgc agccgtggca tcgttgagga gtgctgtttc cgcagctgtg 240
acctggccct cctggagacg tactgtgcta cccccgccaa gtccgagggc gcgccggcac 300
accccggccg tcccagagca gtgcccacac agtgcgacgt cccccccaac agccgcttcg 360
attgcgcccc tgacaaggcc atcacccagg aacagtgcga ggcccgcggc tgctgctaca 420
tccctgcaaa gcaggggctg cagggagccc agatggggca gccctggtgc ttcttcccac 480
ccagctaccc cagctacaag ctggagaacc tgagctcctc tgaaatgggc tacacggcca 540
ccctgacccg taccaccccc accttcttcc ccaaggacat cctgaccctg cggctggacg 600
tgatgatgga gactgagaac cgcctccact tcacgatcaa agatccagct aacaggcgct 660
acgaggtgcc cttggagacc ccgcgtgtcc acagccgggc accgtcccca ctctacagcg 720
tggagttctc tgaggagccc ttcggggtga tcgtgcaccg gcagctggac ggccgcgtgc 780
tgctgaacac gacggtggcg cccctgttct ttgcggacca gttccttcag ctgtccacct 840
cgctgccctc gcagtatatc acaggcctcg ccgagcacct cagtcccctg atgctcagca 900
ccagctggac caggatcacc ctgtggaacc gggaccttgc gcccacgccc ggtgcgaacc 960
tctacgggtc tcaccctttc tacctggcgc tggaggacgg cgggtcggca cacggggtgt 1020
tcctgctaaa cagcaatgcc atggatgtgg tcctgcagcc gagccctgcc cttagctgga 1080
ggtcgacagg tgggatcctg gatgtctaca tcttcctggg cccagagccc aagagcgtgg 1140
tgcagcagta cctggacgtt gtgggatacc cgttcatgcc gccatactgg ggcctgggct 1200
tccacctgtg ccgctggggc tactcctcca ccgctatcac ccgccaggtg gtggagaaca 1260
tgaccagggc ccacttcccc ctggacgtcc aatggaacga cctggactac atggactccc 1320
ggagggactt cacgttcaac aaggatggct tccgggactt cccggccatg gtgcaggagc 1380
tgcaccaggg cggccggcgc tacatgatga tcgtggatcc tgccatcagc agctcgggcc 1440
ctgccgggag ctacaggccc tacgacgagg gtctgcggag gggggttttc atcaccaacg 1500
agaccggcca gccgctgatt gggaaggtat ggcccgggtc cactgccttc cccgacttca 1560
ccaaccccac agccctggcc tggtgggagg acatggtggc tgagttccat gaccaggtgc 1620
ccttcgacgg catgtggatt gacatgaacg agccttccaa cttcatcagg ggctctgagg 1680
acggctgccc caacaatgag ctggagaacc caccctacgt gcctggggtg gttgggggga 1740
ccctccaggc ggcaaccatc tgtgcctcca gccaccagtt tctctccaca cactacaacc 1800
tgcacaacct ctacggcctg accgaagcca tcgcctccca cagggcgctg gtgaaggctc 1860
gggggacacg cccatttgtg atctcccgct cgacctttgc tggccacggc cgatacgccg 1920
gccactggac gggggacgtg tggagctcct gggagcagct cgcctcctcc gtgccagaaa 1980
tcctgcagtt taacctgctg gggtgcctc tggtcggggc cgacgtctgc ggcttcctgg 2040
gcaacacctc agaggagctg tgtgtgcgct ggacccagct gggggccttc taccccttca 2100
tgcggaacca caacagcctg ctcagtctgc cccaggagcc gtacagcttc agcgagccgg 2160
cccagcaggc catgaggaag gccctcaccc tgcgctacgc actcctcccc cacctctaca 2220
cgctgttcca ccaggcccac gtcgcggggg agaccgtggc ccggcccctc ttcctggagt 2280
tccccaagga ctctagcacc tggactgtgg accaccagct cctgtggggg gaggccctgc 2340
tcatcacccc agtgctccag gccgggaagg ccgaagtgac tggctacttc cccttgggca 2400
catggtacga cctgcagacg gtgccaatag aggcccttgg cagcctccca cccccacctg 2460
cagctccccg tgagccagcc atccacagcg aggggcagtg ggtgacgctg ccggcccccc 2520
tggacaccat caacgtccac ctccgggctg ggtacatcat ccccctgcag ggccctggcc 2580
tcacaaccac agagtcccgc cagcagccca tggccctggc tgtggccctg accaagggtg 2640
gagaggcccg aggggagctg ttctgggacg atggagagag cctggaagtg ctggagcgag 2700
gggcctacac acaggtcatc ttcctggcca ggaataacac gatcgtgaat gagctggtac 2760
gtgtgaccag tgagggagct ggcctgcagc tgcagaaggt gactgtcctg ggcgtggcca 2820
cggcgcccca gcaggtcctc tccaacggtg tccctgtctc caacttcacc tacagccccg 2880
acaccaaggt cctggacatc tgtgtctcgc tgttgatggg agagcagttt ctcgtcagct 2940
ggtgttagtc tagagcttgc tagcggccgc 2970

<210> SEQ ID NO 15
<211> LENGTH: 2970
<212> TYPE: DNA
<213> ORGANISM: Artificial Sequence
<220> FEATURE:
<223> OTHER INFORMATION: GILTd2-7/A40-GAA70-952 cassette

<400> SEQUENCE: 15
ggtaccagct gctagcaagc taattcacac caatgggaat cccaatgggg aagtcgatgc 60

-continued

```
tggtgcttct caccttcttg gccttcgcct cgtgctgcat tgctgctctg tgcggcgggg    120
agctggtgga caccctccag ttcgtctgtg ggaccgcggg cttctacttc agcaggcccg    180
caagccgtgt gagccgtcgc agcgctggca tcgttgagga gtgctgtttc cgcagctgtg    240
acctggccct cctggagacg tactgtgcta cccccgccaa gtccgagggc gcgccggcac    300
accccggccg tcccagagca gtgcccacac agtgcgacgt cccccccaac agccgcttcg    360
attgcgcccc tgacaaggcc atcacccagg aacagtgcga ggcccgcggc tgctgctaca    420
tccctgcaaa gcaggggctg cagggagccc agatggggca gccctggtgc ttcttcccac    480
ccagctaccc cagctacaag ctggagaacc tgagctcctc tgaaatgggc tacacggcca    540
ccctgacccg taccaccccc accttcttcc ccaaggacat cctgaccctg cggctggacg    600
tgatgatgga gactgagaac cgcctccact tcacgatcaa agatccagct aacaggcgct    660
acgaggtgcc cttggagacc ccgcgtgtcc acagccgggc accgtcccca ctctacagcg    720
tggagttctc tgaggagccc ttcggggtga tcgtgcaccg gcagctggac ggccgcgtgc    780
tgctgaacac gacggtggcg cccctgttct ttgcggacca gttccttcag ctgtccacct    840
cgctgccctc gcagtatatc acaggcctcg ccgagcacct cagtcccctg atgctcagca    900
ccagctggac caggatcacc ctgtggaacc gggaccttgc gcccacgccc ggtgcgaacc    960
tctacgggtc tcaccctttc tacctggcgc tggaggacgg cgggtcggca cacggggtgt   1020
tcctgctaaa cagcaatgcc atggatgtgg tcctgcagcc gagccctgcc cttagctgga   1080
ggtcgacagg tgggatcctg gatgtctaca tcttcctggg cccagagccc aagagcgtgg   1140
tgcagcagta cctggacgtt gtgggatacc cgttcatgcc gccatactgg ggcctgggct   1200
tccacctgtg ccgctggggc tactcctcca ccgctatcac ccgccaggtg gtggagaaca   1260
tgaccagggc ccacttcccc ctggacgtcc aatggaacga cctggactac atggactccc   1320
ggagggactt cacgttcaac aaggatggct tccgggactt cccggccatg gtgcaggagc   1380
tgcaccaggg cggccggcgc tacatgatga tcgtggatcc tgccatcagc agctcgggcc   1440
ctgccgggag ctacaggccc tacgacgagg gtctgcggag gggggttttc atcaccaacg   1500
agaccggcca gccgctgatt gggaaggtat ggcccgggtc cactgccttc cccgacttca   1560
ccaaccccac agccctggcc tggtgggagg acatggtggc tgagttccat gaccaggtgc   1620
ccttcgacgg catgtggatt gacatgaacg agccttccaa cttcatcagg ggctctgagg   1680
acggctgccc caacaatgag ctggagaacc caccctacgt gcctggggtg gttgggggga   1740
ccctccaggc ggcaaccatc tgtgcctcca gccaccagtt tctctccaca cactacaacc   1800
tgcacaacct ctacggcctg accgaagcca tcgcctccca cagggcgctg gtgaaggctc   1860
gggggacacg cccatttgtg atctcccgct cgacctttgc tggccacggc cgatacgccg   1920
gccactggac gggggacgtg tggagctcct gggagcagct cgcctcctcc gtgccagaaa   1980
tcctgcagtt taacctgctg gggggtgcctc tggtcggggc cgacgtctgc ggcttcctgg   2040
gcaacacctc agaggagctg tgtgtgcgct ggacccagct gggggccttc taccccttca   2100
tgcggaacca caacagcctg ctcagtctgc cccaggagcc gtacagcttc agcgagccgg   2160
cccagcaggc catgaggaag gccctcaccc tgcgctacgc actcctcccc cacctctaca   2220
cgctgttcca ccaggcccac gtcgcggggg agaccgtggc ccggcccctc ttcctggagt   2280
tccccaagga ctctagcacc tggactgtgg accaccagct cctgtggggg gaggccctgc   2340
tcatcacccc agtgctccag gccgggaagg ccgaagtgac tggctacttc cccttgggca   2400
catggtacga cctgcagacg gtgccaatag aggcccttgg cagcctccca cccccacctg   2460
```

```
cagctccccg tgagccagcc atccacagcg aggggcagtg ggtgacgctg ccggcccccc   2520

tggacaccat caacgtccac ctccgggctg ggtacatcat ccccctgcag ggccctggcc   2580

tcacaaccac agagtcccgc cagcagccca tggccctggc tgtggccctg accaagggtg   2640

gagaggcccg aggggagctg ttctgggacg atggagagag cctggaagtg ctggagcgag   2700

gggcctacac acaggtcatc ttcctggcca ggaataacac gatcgtgaat gagctggtac   2760

gtgtgaccag tgagggagct ggcctgcagc tgcagaaggt gactgtcctg ggcgtggcca   2820

cggcgcccca gcaggtcctc tccaacggtg tccctgtctc caacttcacc tacagccccg   2880

acaccaaggt cctggacatc tgtgtctcgc tgttgatggg agagcagttt ctcgtcagct   2940

ggtgttagtc tagagcttgc tagcggccgc                                    2970
```

<210> SEQ ID NO 16
<211> LENGTH: 2953
<212> TYPE: DNA
<213> ORGANISM: Artificial Sequence
<220> FEATURE:
<223> OTHER INFORMATION: GILTd2-7M1/K37-GAA70-952 cassette

<400> SEQUENCE: 16

```
ggtaccaagc ttgccatggg aatcccaatg ggcaagtcga tgctggtgct gctcaccttc     60

ttggcctttg cctcgtgctg cattgccgct ctgtgcggcg gggaactggt ggacaccctc    120

caattcgtct gtggggaccg gggcttctac ttcagcagac ccgcaagccg tgtgagtaag    180

cgcagccgtg gcattgttga ggagtgctgt tttcgcagct gtgacctggc tctcctggag    240

acgtactgcg ctacccccgc caagtctgag ggcgcgccgg cacaccccgg ccgtcccaga    300

gcagtgccca cacagtgcga cgtccccccc aacagccgct tcgattgcgc ccctgacaag    360

gccatcaccc aggaacagtg cgaggcccgc ggctgctgct acatccctgc aaagcagggg    420

ctgcagggag cccagatggg gcagccctgg tgcttcttcc cacccagcta ccccagctac    480

aagctggaga acctgagctc ctctgaaatg ggctacacgg ccaccctgac ccgtaccacc    540

cccaccttct tccccaagga catcctgacc ctgcggctgg acgtgatgat ggagactgag    600

aaccgcctcc acttcacgat caaagatcca gctaacaggc gctacgaggt gcccttggag    660

accccgcgtg tccacagccg ggcaccgtcc ccactctaca gcgtggagtt ctctgaggag    720

cccttcgggg tgatcgtgca ccggcagctg gacggccgcg tgctgctgaa cacgacggtg    780

gcgcccctgt tctttgcgga ccagttcctt cagctgtcca cctcgctgcc ctcgcagtat    840

atcacaggcc tcgccgagca cctcagtccc ctgatgctca gcaccagctg gaccaggatc    900

accctgtgga accgggacct tgcgcccacg cccggtgcga acctctacgg gtctcaccct    960

ttctacctgg cgctggagga cggcgggtcg gcacacgggg tgttcctgct aaacagcaat   1020

gccatggatg tggtcctgca gccgagccct gcccttagct ggaggtcgac aggtgggatc   1080

ctggatgtct acatcttcct gggcccagag cccaagagcg tggtgcagca gtacctggac   1140

gttgtgggat acccgttcat gccgccatac tggggcctgg gcttccacct gtgccgctgg   1200

ggctactcct ccaccgctat cacccgccag gtggtggaga acatgaccag ggcccacttc   1260

cccctggacg tccaatggaa cgacctggac tacatggact cccggaggga cttcacgttc   1320

aacaaggatg gcttccggga cttcccggcc atggtgcagg agctgcacca gggcggccgg   1380

cgctacatga tgatcgtgga tcctgccatc agcagctcgg gccctgccgg gagctacagg   1440

ccctacgacg agggtctgcg gagggggtt ttcatcacca acgagaccgg ccagccgctg   1500

attgggaagg tatggcccgg gtccactgcc ttccccgact tcaccaaccc cacagccctg   1560
```

```
gcctggtggg aggacatggt ggctgagttc catgaccagg tgcccttcga cggcatgtgg   1620

attgacatga acgagccttc caacttcatc aggggctctg aggacggctg ccccaacaat   1680

gagctggaga acccacccta cgtgcctggg gtggttgggg ggaccctcca ggcggcaacc   1740

atctgtgcct ccagccacca gtttctctcc acacactaca acctgcacaa cctctacggc   1800

ctgaccgaag ccatcgcctc ccacagggcg ctggtgaagg ctcgggggac acgcccattt   1860

gtgatctccc gctcgacctt tgctggccac ggccgatacg ccggccactg gacgggggac   1920

gtgtggagct cctgggagca gctcgcctcc tccgtgccag aaatcctgca gtttaacctg   1980

ctgggggtgc ctctggtcgg ggccgacgtc tgcggcttcc tgggcaacac ctcagaggag   2040

ctgtgtgtgc gctggaccca gctgggggcc ttctacccct tcatgcggaa ccacaacagc   2100

ctgctcagtc tgccccagga gccgtacagc ttcagcgagc cggcccagca ggccatgagg   2160

aaggccctca ccctgcgcta cgcactcctc ccccacctct acacgctgtt ccaccaggcc   2220

cacgtcgcgg gggagaccgt ggcccggccc ctcttcctgg agttccccaa ggactctagc   2280

acctggactg tggaccacca gctcctgtgg ggggaggccc tgctcatcac cccagtgctc   2340

caggccggga aggccgaagt gactggctac ttccccttgg gcacatggta cgacctgcag   2400

acggtgccaa tagaggccct tggcagcctc ccaccccac ctgcagctcc ccgtgagcca   2460

gccatccaca gcgaggggca gtgggtgacg ctgccggccc ccctggacac catcaacgtc   2520

cacctccggg ctgggtacat catcccctg cagggccctg gcctcacaac cacagagtcc   2580

cgccagcagc ccatggccct ggctgtggcc ctgaccaagg gtggagaggc ccgaggggag   2640

ctgttctggg acgatggaga gagcctggaa gtgctggagc gaggggccta cacacaggtc   2700

atcttcctgg ccaggaataa cacgatcgtg aatgagctgg tacgtgtgac cagtgaggga   2760

gctggcctgc agctgcagaa ggtgactgtc ctgggcgtgg ccacggcgcc ccagcaggtc   2820

ctctccaacg gtgtccctgt ctccaacttc acctacagcc ccgacaccaa ggtcctggac   2880

atctgtgtct cgctgttgat gggagagcag tttctcgtca gctggtgtta gtctagagct   2940

tgctagcggc cgc                                                      2953
```

<210> SEQ ID NO 17
<211> LENGTH: 2953
<212> TYPE: DNA
<213> ORGANISM: Artificial Sequence
<220> FEATURE:
<223> OTHER INFORMATION: GILTd2-7M1/A37-GAA70-952 cassette

<400> SEQUENCE: 17

```
ggtaccaagc ttgccatggg aatcccaatg ggcaagtcga tgctggtgct gctcaccttc     60

ttggcctttg cctcgtgctg cattgccgct ctgtgcggcg gggaactggt ggacaccctc    120

caattcgtct gtggggaccg gggcttctac ttcagcagac ccgcaagccg tgtgagtgct    180

cgcagccgtg gcattgttga ggagtgctgt tttcgcagct gtgacctggc tctcctggag    240

acgtactgcg ctacccccgc caagtctgag ggcgcgccgg cacaccccgg ccgtcccaga    300

gcagtgccca cacagtgcga cgtccccccc aacagccgct tcgattgcgc ccctgacaag    360

gccatcaccc aggaacagtg cgaggcccgc ggctgctgct acatccctgc aaagcagggg    420

ctgcagggag cccagatggg gcagccctgg tgcttcttcc cacccagcta ccccagctac    480

aagctggaga acctgagctc ctctgaaatg ggctacacgg ccaccctgac ccgtaccacc    540

cccaccttct tccccaagga catcctgacc ctgcggctgg acgtgatgat ggagactgag    600

aaccgcctcc acttcacgat caaagatcca gctaacaggc gctacgaggt gcccttggag    660
```

-continued

```
accccgcgtg tccacagccg ggcaccgtcc ccactctaca gcgtggagtt ctctgaggag    720
cccttcgggg tgatcgtgca ccggcagctg gacggccgcg tgctgctgaa cacgacggtg    780
gcgcccctgt tctttgcgga ccagttcctt cagctgtcca cctcgctgcc ctcgcagtat    840
atcacaggcc tcgccgagca cctcagtccc ctgatgctca gcaccagctg gaccaggatc    900
accctgtgga accgggacct tgcgcccacg cccggtgcga acctctacgg gtctcaccct    960
ttctacctgg cgctggagga cggcgggtcg gcacacgggg tgttcctgct aaacagcaat   1020
gccatggatg tggtcctgca gccgagccct gcccttagct ggaggtcgac aggtgggatc   1080
ctggatgtct acatcttcct gggcccagag cccaagagcg tggtgcagca gtacctggac   1140
gttgtgggat acccgttcat gccgccatac tggggcctgg gcttccacct gtgccgctgg   1200
ggctactcct ccaccgctat cacccgccag gtggtggaga acatgaccag ggcccacttc   1260
cccctggacg tccaatggaa cgacctggac tacatggact cccggaggga cttcacgttc   1320
aacaaggatg gcttccggga cttcccggcc atggtgcagg agctgcacca gggcggccgg   1380
cgctacatga tgatcgtgga tcctgccatc agcagctcgg gccctgccgg gagctacagg   1440
ccctacgacg agggtctgcg gagggggtt ttcatcacca acgagaccgg ccagccgctg    1500
attgggaagg tatggcccgg gtccactgcc ttccccgact tcaccaaccc cacagccctg   1560
gcctggtggg aggacatggt ggctgagttc catgaccagg tgcccttcga cggcatgtgg   1620
attgacatga acgagccttc caacttcatc aggggctctg aggacggctg ccccaacaat   1680
gagctggaga acccacccta cgtgcctggg gtggttgggg ggaccctcca ggcggcaacc   1740
atctgtgcct ccagccacca gtttctctcc acacactaca acctgcacaa cctctacggc   1800
ctgaccgaag ccatcgcctc ccacagggcg ctggtgaagg ctcgggggac acgcccattt   1860
gtgatctccc gctcgacctt tgctggccac ggccgatacg ccggccactg gacgggggac   1920
gtgtggagct cctgggagca gctcgcctcc tccgtgccag aaatcctgca gtttaacctg   1980
ctgggggtgc ctctggtcgg ggccgacgtc tgcggcttcc tgggcaacac ctcagaggag   2040
ctgtgtgtgc gctggaccca gctgggggcc ttctacccct tcatgcggaa ccacaacagc   2100
ctgctcagtc tgccccagga gccgtacagc ttcagcgagc cggcccagca ggccatgagg   2160
aaggccctca ccctgcgcta cgcactcctc ccccacctct acacgctgtt ccaccaggcc   2220
cacgtcgcgg gggagaccgt ggcccggccc ctcttcctgg agttccccaa ggactctagc   2280
acctggactg tggaccacca gctcctgtgg ggggaggccc tgctcatcac cccagtgctc   2340
caggccggga aggccgaagt gactggctac ttccccttgg gcacatggta cgacctgcag   2400
acggtgccaa tagaggccct tggcagcctc ccacccccac ctgcagctcc ccgtgagcca   2460
gccatccaca gcgaggggca gtgggtgacg ctgccggccc ccctggacac catcaacgtc   2520
cacctccggg ctgggtacat catcccctg cagggccctg gcctcacaac cacagagtcc    2580
cgccagcagc ccatggccct ggctgtggcc ctgaccaagg gtggagaggc ccgaggggag   2640
ctgttctggg acgatggaga gagcctggaa gtgctggagc gaggggccta cacacaggtc   2700
atcttcctgg ccaggaataa cacgatcgtg aatgagctgg tacgtgtgac cagtgaggga   2760
gctggcctgc agctgcagaa ggtgactgtc ctgggcgtgg ccacggcgcc ccagcaggtc   2820
ctctccaacg gtgtccctgt ctccaacttc acctacagcc ccgacaccaa ggtcctggac   2880
atctgtgtct cgctgttgat gggagagcag tttctcgtca gctggtgtta gtctagagct   2940
tgctagcggc cgc                                                      2953
```

-continued

<210> SEQ ID NO 18
<211> LENGTH: 2940
<212> TYPE: DNA
<213> ORGANISM: Artificial Sequence
<220> FEATURE:
<223> OTHER INFORMATION: GILTd2-7d30-39-GAA70-952 cassette

<400> SEQUENCE: 18

```
ggtaccagct gctagcaagc taattcacac caatgggaat cccaatgggg aagtcgatgc     60

tggtgcttct caccttcttg gccttcgcct cgtgctgcat tgctgctctg tgcggcgggg    120

agctggtgga caccctccag ttcgtctgtg ggaccgcgg cttctacttc agccgtggca    180

tcgttgagga gtgctgtttc cgcagctgtg acctggccct cctggagacg tactgtgcta    240

cccccgccaa gtccgagggc gcgccggcac accccggccg tcccagagca gtgcccacac    300

agtgcgacgt ccccccccaac agccgcttcg attgcgcccc tgacaaggcc atcacccagg    360

aacagtgcga ggcccgcggc tgctgctaca tccctgcaaa gcaggggctg cagggagccc    420

agatggggca gccctggtgc ttcttcccac ccagctaccc cagctacaag ctggagaacc    480

tgagctcctc tgaaatgggc tacacggcca ccctgacccg taccaccccc accttcttcc    540

ccaaggacat cctgaccctg cggctggacg tgatgatgga gactgagaac cgcctccact    600

tcacgatcaa agatccagct aacaggcgct acgaggtgcc cttggagacc ccgcgtgtcc    660

acagccgggc accgtcccca ctctacagcg tggagttctc tgaggagccc ttcggggtga    720

tcgtgcaccg gcagctggac ggccgcgtgc tgctgaacac gacggtggcg cccctgttct    780

ttgcggacca gttccttcag ctgtccacct cgctgccctc gcagtatatc acaggcctcg    840

ccgagcacct cagtcccctg atgctcagca ccagctggac caggatcacc ctgtggaacc    900

gggaccttgc gcccacgccc ggtgcgaacc tctacgggtc tcaccctttc tacctggcgc    960

tggaggacgg cgggtcggca cacggggtgt tcctgctaaa cagcaatgcc atggatgtgg   1020

tcctgcagcc gagccctgcc cttagctgga ggtcgacagg tgggatcctg gatgtctaca   1080

tcttcctggg cccagagccc aagagcgtgg tgcagcagta cctggacgtt gtgggatacc   1140

cgttcatgcc gccatactgg ggcctgggct tccacctgtg ccgctggggc tactcctcca   1200

ccgctatcac ccgccaggtg gtggagaaca tgaccagggc ccacttcccc ctggacgtcc   1260

aatggaacga cctggactac atggactccc ggagggactt cacgttcaac aaggatggct   1320

tccgggactt cccggccatg gtgcaggagc tgcaccaggg cggccggcgc tacatgatga   1380

tcgtggatcc tgccatcagc agctcgggcc ctgccgggag ctacaggccc tacgacgagg   1440

gtctgcggag gggggttttc atcaccaacg agaccggcca gccgctgatt gggaaggtat   1500

ggcccgggtc cactgccttc cccgacttca ccaaccccac agccctggcc tggtgggagg   1560

acatggtggc tgagttccat gaccaggtgc ccttcgacgg catgtggatt gacatgaacg   1620

agccttccaa cttcatcagg ggctctgagg acggctgccc caacaatgag ctggagaacc   1680

caccctacgt gcctggggtg gttgggggga ccctccaggc ggcaaccatc tgtgcctcca   1740

gccaccagtt tctctccaca cactacaacc tgcacaacct ctacggcctg accgaagcca   1800

tcgcctccca cagggcgctg gtgaaggctc gggggacacg cccatttgtg atctcccgct   1860

cgacctttgc tggccacggc cgatacgccg gccactggac gggggacgtg tggagctcct   1920

gggagcagct cgcctcctcc gtgccagaaa tcctgcagtt taacctgctg ggggtgcctc   1980

tggtcggggc cgacgtctgc ggcttcctgg gcaacacctc agaggagctg tgtgtgcgct   2040

ggacccagct gggggccttc taccccttca tgcggaacca caacagcctg ctcagtctgc   2100

cccaggagcc gtacagcttc agcgagccgg cccagcaggc catgaggaag gccctcaccc   2160
```

tgcgctacgc actcctcccc cacctctaca cgctgttcca ccaggcccac gtcgcggggg 2220
agaccgtggc ccggcccctc ttcctggagt tccccaagga ctctagcacc tggactgtgg 2280
accaccagct cctgtggggg gaggccctgc tcatcacccc agtgctccag gccgggaagg 2340
ccgaagtgac tggctacttc cccttgggca catggtacga cctgcagacg gtgccaatag 2400
aggcccttgg cagcctccca cccccacctg cagctccccg tgagccagcc atccacagcg 2460
aggggcagtg ggtgacgctg ccggccccc tggacaccat caacgtccac ctccgggctg 2520
ggtacatcat ccccctgcag ggccctggcc tcacaaccac agagtcccgc cagcagccca 2580
tggccctggc tgtggccctg accaagggtg gagaggcccg aggggagctg ttctgggacg 2640
atggagagag cctggaagtg ctggagcgag ggcctacac acaggtcatc ttcctggcca 2700
ggaataacac gatcgtgaat gagctggtac gtgtgaccag tgagggagct ggcctgcagc 2760
tgcagaaggt gactgtcctg ggcgtggcca cggcgcccca gcaggtcctc tccaacggtg 2820
tccctgtctc caacttcacc tacagccccg acaccaaggt cctggacatc tgtgtctcgc 2880
tgttgatggg agagcagttt ctcgtcagct ggtgttagtc tagagcttgc tagcggccgc 2940

<210> SEQ ID NO 19
<211> LENGTH: 2943
<212> TYPE: DNA
<213> ORGANISM: Artificial Sequence
<220> FEATURE:
<223> OTHER INFORMATION: GILTd2-7d31-39-GAA70-952 cassette

<400> SEQUENCE: 19
ggtaccagct gctagcaagc taattcacac caatgggaat cccaatgggg aagtcgatgc 60
tggtgcttct caccttcttg gccttcgcct cgtgctgcat tgctgctctg tgcggcgggg 120
agctggtgga caccctccag ttcgtctgtg gggaccgcgg cttctacttc agcaggcgtg 180
gcatcgttga ggagtgctgt ttccgcagct gtgacctggc cctcctggag acgtactgtg 240
ctacccccgc caagtccgag ggcgcgccgg cacaccccgg ccgtcccaga gcagtgccca 300
cacagtgcga cgtccccccc aacagccgct tcgattgcgc ccctgacaag gccatcaccc 360
aggaacagtg cgaggcccgc ggctgctgct acatccctgc aaagcagggg ctgcagggag 420
cccagatggg gcagccctgg tgcttcttcc cacccagcta ccccagctac aagctggaga 480
acctgagctc ctctgaaatg ggctacacgg ccaccctgac ccgtaccacc cccaccttct 540
tccccaagga catcctgacc ctgcggctgg acgtgatgat ggagactgag aaccgcctcc 600
acttcacgat caaagatcca gctaacaggc gctacgaggt gcccttggag accccgcgtg 660
tccacagccg ggcaccgtcc ccactctaca gcgtggagtt ctctgaggag cccttcgggg 720
tgatcgtgca ccggcagctg gacggccgcg tgctgctgaa cacgacggtg gcgcccctgt 780
tctttgcgga ccagttcctt cagctgtcca cctcgctgcc ctcgcagtat atcacaggcc 840
tcgccgagca cctcagtccc ctgatgctca gcaccagctg gaccaggatc accctgtgga 900
accgggacct tgcgcccacg cccggtgcga acctctacgg gtctcaccct ttctacctgg 960
cgctggagga cggcgggtcg gcacacgggg tgttcctgct aaacagcaat gccatggatg 1020
tggtcctgca gccgagccct gcccttagct ggaggtcgac aggtgggatc ctggatgtct 1080
acatcttcct gggcccagag cccaagagcg tggtgcagca gtacctggac gttgtgggat 1140
acccgttcat gccgccatac tggggcctgg gcttccacct gtgccgctgg ggctactcct 1200
ccaccgctat cacccgccag gtggtggaga acatgaccag ggcccacttc cccctggacg 1260
tccaatggaa cgacctggac tacatggact cccggaggga cttcacgttc aacaaggatg 1320
gcttccggga cttcccggcc atggtgcagg agctgcacca gggcggccgg cgctacatga 1380
tgatcgtgga tcctgccatc agcagctcgg gccctgccgg gagctacagg ccctacgacg 1440
agggtctgcg gaggggggtt ttcatcacca acgagaccgg ccagccgctg attgggaagg 1500
tatggcccgg gtccactgcc ttccccgact tcaccaaccc cacagccctg gcctggtggg 1560
aggacatggt ggctgagttc catgaccagg tgcccttcga cggcatgtgg attgacatga 1620
acgagccttc caacttcatc aggggctctg aggacggctg ccccaacaat gagctggaga 1680
acccacccta cgtgcctggg gtggttgggg ggaccctcca ggcggcaacc atctgtgcct 1740
ccagccacca gtttctctcc acacactaca acctgcacaa cctctacggc ctgaccgaag 1800
ccatcgcctc ccacagggcg ctggtgaagg ctcgggggac acgcccattt gtgatctccc 1860
gctcgacctt tgctggccac ggccgatacg ccggccactg gacgggggac gtgtggagct 1920
cctgggagca gctcgcctcc tccgtgccag aaatcctgca gtttaacctg ctgggggtgc 1980
ctctggtcgg ggccgacgtc tgcggcttcc tgggcaacac ctcagaggag ctgtgtgtgc 2040
gctggaccca gctgggggcc ttctacccct tcatgcggaa ccacaacagc ctgctcagtc 2100
tgccccagga gccgtacagc ttcagcgagc cggcccagca ggccatgagg aaggccctca 2160
ccctgcgcta cgcactcctc ccccacctct acacgctgtt ccaccaggcc cacgtcgcgg 2220
gggagaccgt ggcccggccc ctcttcctgg agttccccaa ggactctagc acctggactg 2280
tggaccacca gctcctgtgg ggggaggccc tgctcatcac cccagtgctc caggccggga 2340
aggccgaagt gactggctac ttccccttgg gcacatggta cgacctgcag acggtgccaa 2400
tagaggccct tggcagcctc ccacccccac ctgcagctcc ccgtgagcca gccatccaca 2460
gcgaggggca gtgggtgacg ctgccggccc ccctggacac catcaacgtc cacctccggg 2520
ctgggtacat catccccctg cagggccctg gcctcacaac cacagagtcc cgccagcagc 2580
ccatggccct ggctgtggcc ctgaccaagg gtggagaggc ccgaggggag ctgttctggg 2640
acgatggaga gagcctggaa gtgctggagc gaggggccta cacacaggtc atcttcctgg 2700
ccaggaataa cacgatcgtg aatgagctgg tacgtgtgac cagtgaggga gctggcctgc 2760
agctgcagaa ggtgactgtc ctgggcgtgg ccacggcgcc ccagcaggtc ctctccaacg 2820
gtgtccctgt ctccaacttc acctacagcc ccgacaccaa ggtcctggac atctgtgtct 2880
cgctgttgat gggagagcag tttctcgtca gctggtgtta gtctagagct tgctagcggc 2940
cgc 2943

<210> SEQ ID NO 20
<211> LENGTH: 2946
<212> TYPE: DNA
<213> ORGANISM: Artificial Sequence
<220> FEATURE:
<223> OTHER INFORMATION: GILTd2-7d32-39-GAA70-952 cassette

<400> SEQUENCE: 20
ggtaccagct gctagcaagc taattcacac caatgggaat cccaatgggg aagtcgatgc 60
tggtgcttct caccttcttg gccttcgcct cgtgctgcat tgctgctctg tgcggcgggg 120
agctggtgga caccctccag ttcgtctgtg gggaccgcgg cttctacttc agcaggcccc 180
gtggcatcgt tgaggagtgc tgtttccgca gctgtgacct ggccctcctg gagacgtact 240
gtgctacccc cgccaagtcc gagggcgcgc cggcacaccc cggccgtccc agagcagtgc 300
ccacacagtg cgacgtcccc cccaacagcc gcttcgattg cgcccctgac aaggccatca 360
cccaggaaca gtgcgaggcc cgcggctgct gctacatccc tgcaaagcag gggctgcagg 420

-continued

```
gagcccagat ggggcagccc tggtgcttct tcccacccag ctaccccagc tacaagctgg    480
agaacctgag ctcctctgaa atgggctaca cggccaccct gacccgtacc acccccacct    540
tcttccccaa ggacatcctg accctgcggc tggacgtgat gatggagact gagaaccgcc    600
tccacttcac gatcaaagat ccagctaaca ggcgctacga ggtgcccttg gagaccccgc    660
gtgtccacag ccgggcaccg tccccactct acagcgtgga gttctctgag gagcccttcg    720
gggtgatcgt gcaccggcag ctggacggcc gcgtgctgct gaacacgacg gtggcgcccc    780
tgttctttgc ggaccagttc cttcagctgt ccacctcgct gccctcgcag tatatcacag    840
gcctcgccga gcacctcagt cccctgatgc tcagcaccag ctggaccagg atcaccctgt    900
ggaaccggga ccttgcgccc acgcccggtg cgaacctcta cgggtctcac cctttctacc    960
tggcgctgga ggacggcggg tcggcacacg ggtgttcct gctaaacagc aatgccatgg   1020
atgtggtcct gcagccgagc cctgccctta gctggaggtc gacaggtggg atcctggatg   1080
tctacatctt cctgggccca gagcccaaga gcgtggtgca gcagtacctg gacgttgtgg   1140
gatacccgtt catgccgcca tactggggcc tgggcttcca cctgtgccgc tggggctact   1200
cctccaccgc tatcacccgc caggtggtgg agaacatgac cagggcccac ttcccccctgg  1260
acgtccaatg gaacgacctg gactacatgg actcccggag ggacttcacg ttcaacaagg   1320
atggcttccg ggacttcccg gccatggtgc aggagctgca ccagggcggc cggcgctaca   1380
tgatgatcgt ggatcctgcc atcagcagct cgggccctgc cgggagctac aggccctacg   1440
acgagggtct gcggaggggg gttttcatca ccaacgagac cggccagccg ctgattggga   1500
aggtatggcc cgggtccact gccttccccg acttcaccaa ccccacagcc ctggcctggt   1560
gggaggacat ggtggctgag ttccatgacc aggtgccctt cgacggcatg tggattgaca   1620
tgaacgagcc ttccaacttc atcaggggct ctgaggacgg ctgccccaac aatgagctgg   1680
agaacccacc ctacgtgcct ggggtggttg gggggaccct ccaggcggca accatctgtg   1740
cctccagcca ccagtttctc tccacacact acaacctgca caacctctac ggcctgaccg   1800
aagccatcgc ctcccacagg gcgctggtga aggctcgggg gacacgccca tttgtgatct   1860
cccgctcgac ctttgctggc cacggccgat acgccggcca ctggacgggg gacgtgtgga   1920
gctcctggga gcagctcgcc tcctccgtgc cagaaatcct gcagtttaac ctgctggggg   1980
tgcctctggt cggggccgac gtctgcggct tcctgggcaa cacctcagag gagctgtgtg   2040
tgcgctggac ccagctgggg gccttctacc ccttcatgcg gaaccacaac agcctgctca   2100
gtctgcccca ggagccgtac agcttcagcg agccggccca gcaggccatg aggaaggccc   2160
tcaccctgcg ctacgcactc ctcccccacc tctacacgct gttccaccag gcccacgtcg   2220
cgggggagac cgtggcccgg cccctcttcc tggagttccc caaggactct agcacctgga   2280
ctgtggacca ccagctcctg tggggggagg ccctgctcat caccccagtg ctccaggccg   2340
ggaaggccga agtgactggc tacttcccct tgggcacatg gtacgacctg cagacggtgc   2400
caatagaggc ccttggcagc ctcccacccc cacctgcagc tccccgtgag ccagccatcc   2460
acagcgaggg gcagtgggtg acgctgccgg cccccctgga caccatcaac gtccacctcc   2520
gggctgggta catcatcccc ctgcagggcc ctggcctcac aaccacagag tcccgccagc   2580
agcccatggc cctggctgtg gccctgacca agggtggaga ggcccgaggg gagctgttct   2640
gggacgatgg agagagcctg gaagtgctgg agcgaggggc ctacacacag gtcatcttcc   2700
tggccaggaa taacacgatc gtgaatgagc tggtacgtgt gaccagtgag ggagctggcc   2760
tgcagctgca gaaggtgact gtcctgggcg tggccacggc gccccagcag gtcctctcca   2820
```

acggtgtccc tgtctccaac ttcacctaca gccccgacac caaggtcctg gacatctgtg 2880
tctcgctgtt gatgggagag cagtttctcg tcagctggtg ttagtctaga gcttgctagc 2940
ggccgc 2946

<210> SEQ ID NO 21
<211> LENGTH: 2949
<212> TYPE: DNA
<213> ORGANISM: Artificial Sequence
<220> FEATURE:
<223> OTHER INFORMATION: GILTd2-7d33-39-GAA70-952 cassette

<400> SEQUENCE: 21
ggtaccagct gctagcaagc taattcacac caatgggaat cccaatgggg aagtcgatgc 60
tggtgcttct caccttcttg gccttcgcct cgtgctgcat tgctgctctg tgcggcgggg 120
agctggtgga caccctccag ttcgtctgtg gggaccgcgg cttctacttc agcaggcccg 180
cacgtggcat cgttgaggag tgctgtttcc gcagctgtga cctggccctc ctggagacgt 240
actgtgctac ccccgccaag tccgagggcg cgccggcaca ccccggccgt cccagagcag 300
tgcccacaca gtgcgacgtc ccccccaaca gccgcttcga ttgcgcccct gacaaggcca 360
tcacccagga acagtgcgag gcccgcggct gctgctacat ccctgcaaag caggggctgc 420
agggagccca gatggggcag ccctggtgct tcttcccacc cagctacccc agctacaagc 480
tggagaacct gagctcctct gaaatgggct acacggccac cctgacccgt accaccccca 540
ccttcttccc caaggacatc ctgaccctgc ggctggacgt gatgatggag actgagaacc 600
gcctccactt cacgatcaaa gatccagcta acaggcgcta cgaggtgccc ttggagaccc 660
cgcgtgtcca cagccgggca ccgtccccac tctacagcgt ggagttctct gaggagccct 720
tcggggtgat cgtgcaccgg cagctggacg gccgcgtgct gctgaacacg acggtggcgc 780
ccctgttctt tgcggaccag ttccttcagc tgtccacctc gctgccctcg cagtatatca 840
caggcctcgc cgagcacctc agtcccctga tgctcagcac cagctggacc aggatcaccc 900
tgtggaaccg ggaccttgcg cccacgcccg gtgcgaacct ctacgggtct caccctttct 960
acctggcgct ggaggacggc gggtcggcac acggggtgtt cctgctaaac agcaatgcca 1020
tggatgtggt cctgcagccg agccctgccc ttagctggag gtcgacaggt gggatcctgg 1080
atgtctacat cttcctgggc ccagagccca agagcgtggt gcagcagtac ctggacgttg 1140
tgggataccc gttcatgccg ccatactggg gcctgggctt ccacctgtgc cgctggggct 1200
actcctccac cgctatcacc cgccaggtgg tggagaacat gaccagggcc cacttccccc 1260
tggacgtcca atggaacgac ctggactaca tggactcccg gagggacttc acgttcaaca 1320
aggatggctt ccgggacttc ccggccatgg tgcaggagct gcaccagggc ggccggcgct 1380
acatgatgat cgtggatcct gccatcagca gctcgggccc tgccgggagc tacaggccct 1440
acgacgaggg tctgcggagg ggggttttca tcaccaacga gaccggccag ccgctgattg 1500
ggaaggtatg gcccgggtcc actgccttcc ccgacttcac caaccccaca gccctggcct 1560
ggtgggagga catggtggct gagttccatg accaggtgcc cttcgacggc atgtggattg 1620
acatgaacga gccttccaac ttcatcaggg gctctgagga cggctgcccc aacaatgagc 1680
tggagaaccc accctacgtg cctggggtgg ttgggggggac cctccaggcg gcaaccatct 1740
gtgcctccag ccaccagttt ctctccacac actacaacct gcacaacctc tacggcctga 1800
ccgaagccat cgcctcccac agggcgctgg tgaaggctcg gggggacacgc ccatttgtga 1860 tctcccgctc gacctttgct ggccacggcc gatacgccgg ccactggacg ggggacgtgt 1920
ggagctcctg ggagcagctc gcctcctccg tgccagaaat cctgcagttt aacctgctgg 1980
gggtgcctct ggtcggggcc gacgtctgcg gcttcctggg caacacctca gaggagctgt 2040
gtgtgcgctg gacccagctg gggccttct accccttcat gcggaaccac aacagcctgc 2100
tcagtctgcc ccaggagccg tacagcttca gcgagccggc ccagcaggcc atgaggaagg 2160
ccctcaccct gcgctacgca ctcctccccc acctctacac gctgttccac caggcccacg 2220
tcgcggggga gaccgtggcc cggcccctct tcctggagtt ccccaaggac tctagcacct 2280
ggactgtgga ccaccagctc ctgtgggggg aggccctgct catcacccca gtgctccagg 2340
ccgggaaggc cgaagtgact ggctacttcc ccttgggcac atggtacgac ctgcagacgg 2400
tgccaataga ggcccttggc agcctcccac ccccacctgc agctccccgt gagccagcca 2460
tccacagcga ggggcagtgg gtgacgctgc cggccccct ggacaccatc aacgtccacc 2520
tccgggctgg gtacatcatc cccctgcagg gccctggcct cacaaccaca gagtcccgcc 2580
agcagcccat ggccctggct gtggccctga ccaagggtgg agaggcccga ggggagctgt 2640
tctgggacga tggagagagc ctggaagtgc tggagcgagg ggcctacaca caggtcatct 2700
tcctggccag gaataacacg atcgtgaatg agctggtacg tgtgaccagt gagggagctg 2760
gcctgcagct gcagaaggtg actgtcctgg gcgtggccac ggcgccccag caggtcctct 2820
ccaacggtgt ccctgtctcc aacttcacct acagccccga caccaaggtc ctggacatct 2880
gtgtctcgct gttgatggga gagcagtttc tcgtcagctg gtgttagtct agagcttgct 2940
agcggccgc 2949

<210> SEQ ID NO 22
<211> LENGTH: 2952
<212> TYPE: DNA
<213> ORGANISM: Artificial Sequence
<220> FEATURE:
<223> OTHER INFORMATION: GILTd2-7d34-39-GAA70-952 cassette

<400> SEQUENCE: 22
ggtaccagct gctagcaagc taattcacac caatgggaat cccaatgggg aagtcgatgc 60
tggtgcttct caccttcttg gccttcgcct cgtgctgcat tgctgctctg tgcggcgggg 120
agctggtgga caccctccag ttcgtctgtg gggaccgcgg cttctacttc agcaggcccg 180
caagccgtgg catcgttgag gagtgctgtt tccgcagctg tgacctggcc ctcctggaga 240
cgtactgtgc taccccccgcc aagtccgagg gcgcgccggc acaccccggc cgtcccagag 300
cagtgcccac acagtgcgac gtccccccca acagccgctt cgattgcgcc cctgacaagg 360
ccatcaccca ggaacagtgc gaggcccgcg gctgctgcta catccctgca aagcaggggc 420
tgcagggagc ccagatgggg cagccctggt gcttcttccc acccagctac cccagctaca 480
agctggagaa cctgagctcc tctgaaatgg gctacacggc caccctgacc cgtaccaccc 540
ccaccttctt ccccaaggac atcctgaccc tgcggctgga cgtgatgatg gagactgaga 600
accgcctcca cttcacgatc aaagatccag ctaacaggcg ctacgaggtg cccttggaga 660
ccccgcgtgt ccacagccgg gcaccgtccc cactctacag cgtggagttc tctgaggagc 720
ccttcggggt gatcgtgcac cggcagctgg acggccgcgt gctgctgaac acgacggtgg 780
cgcccctgtt ctttgcggac cagttccttc agctgtccac ctcgctgccc tcgcagtata 840
tcacaggcct cgccgagcac ctcagtcccc tgatgctcag caccagctgg accaggatca 900
ccctgtggaa ccgggacctt gcgcccacgc ccggtgcgaa cctctacggg tctcacccct 960
tctacctggc gctggaggac ggcgggtcgg cacacggggt gttcctgcta aacagcaatg 1020
ccatggatgt ggtcctgcag ccgagccctg cccttagctg gaggtcgaca ggtgggatcc 1080
tggatgtcta catcttcctg ggcccagagc ccaagagcgt ggtgcagcag tacctggacg 1140
ttgtgggata cccgttcatg ccgccatact ggggcctggg cttccacctg tgccgctggg 1200
gctactcctc caccgctatc acccgccagg tggtggagaa catgaccagg gcccacttcc 1260
ccctggacgt ccaatggaac gacctggact acatggactc ccggagggac ttcacgttca 1320
acaaggatgg cttccgggac ttcccggcca tggtgcagga gctgcaccag ggcggccggc 1380
gctacatgat gatcgtggat cctgccatca gcagctcggg ccctgccggg agctacaggc 1440
cctacgacga gggtctgcgg agggggtttt tcatcaccaa cgagaccggc cagccgctga 1500
ttgggaaggt atggcccggg tccactgcct tccccgactt caccaacccc acagccctgg 1560
cctggtggga ggacatggtg gctgagttcc atgaccaggt gcccttcgac ggcatgtgga 1620
ttgacatgaa cgagccttcc aacttcatca ggggctctga ggacggctgc cccaacaatg 1680
agctggagaa cccaccctac gtgcctgggg tggttggggg gaccctccag gcggcaacca 1740
tctgtgcctc cagccaccag tttctctcca cacactacaa cctgcacaac ctctacggcc 1800
tgaccgaagc catcgcctcc cacagggcgc tggtgaaggc tcgggggaca cgcccatttg 1860
tgatctcccg ctcgaccttt gctggccacg gccgatacgc cggccactgg acgggggacg 1920
tgtggagctc ctgggagcag ctcgcctcct ccgtgccaga aatcctgcag tttaacctgc 1980
tgggggtgcc tctggtcggg gccgacgtct gcggcttcct gggcaacacc tcagaggagc 2040
tgtgtgtgcg ctggacccag ctgggggcct tctacccctt catgcggaac cacaacagcc 2100
tgctcagtct gccccaggag ccgtacagct tcagcgagcc ggcccagcag gccatgagga 2160
aggccctcac cctgcgctac gcactcctcc cccacctcta cacgctgttc caccaggccc 2220
acgtcgcggg ggagaccgtg gcccggcccc tcttcctgga gttccccaag gactctagca 2280
cctggactgt ggaccaccag ctcctgtggg gggaggccct gctcatcacc ccagtgctcc 2340
aggccgggaa ggccgaagtg actggctact tccccttggg cacatggtac gacctgcaga 2400
cggtgccaat agaggccctt ggcagcctcc cacccccacc tgcagctccc cgtgagccag 2460
ccatccacag cgaggggcag tgggtgacgc tgccggcccc cctggacacc atcaacgtcc 2520
acctccgggc tgggtacatc atcccctgc agggccctgg cctcacaacc acagagtccc 2580
gccagcagcc catggccctg gctgtggccc tgaccaaggg tggagaggcc cgaggggagc 2640
tgttctggga cgatggagag agcctggaag tgctggagcg aggggcctac acacaggtca 2700
tcttcctggc caggaataac acgatcgtga atgagctggt acgtgtgacc agtgagggag 2760
ctggcctgca gctgcagaag gtgactgtcc tgggcgtggc cacggcgccc cagcaggtcc 2820
tctccaacgg tgtccctgtc tccaacttca cctacagccc cgacaccaag gtcctggaca 2880
tctgtgtctc gctgttgatg ggagagcagt ttctcgtcag ctggtgttag tctagagctt 2940
gctagcggcc gc 2952

<210> SEQ ID NO 23
<211> LENGTH: 2955
<212> TYPE: DNA
<213> ORGANISM: Artificial Sequence
<220> FEATURE:
<223> OTHER INFORMATION: GILTd2-7d35-39-GAA70-952 cassette

<400> SEQUENCE: 23
ggtaccagct gctagcaagc taattcacac caatgggaat cccaatgggg aagtcgatgc 60
tggtgcttct caccttcttg gccttcgcct cgtgctgcat tgctgctctg tgcggcgggg 120

-continued

```
agctggtgga caccctccag ttcgtctgtg gggaccgcgg cttctacttc agcaggcccg    180
caagccgtcg tggcatcgtt gaggagtgct gtttccgcag ctgtgacctg gccctcctgg    240
agacgtactg tgctaccccc gccaagtccg agggcgcgcc ggcacacccc ggccgtccca    300
gagcagtgcc cacacagtgc gacgtccccc ccaacagccg cttcgattgc gcccctgaca    360
aggccatcac ccaggaacag tgcgaggccc gcggctgctg ctacatccct gcaaagcagg    420
ggctgcaggg agcccagatg gggcagccct ggtgcttctt cccacccagc taccccagct    480
acaagctgga gaacctgagc tcctctgaaa tgggctacac ggccaccctg acccgtacca    540
cccccacctt cttccccaag gacatcctga ccctgcggct ggacgtgatg atggagactg    600
agaaccgcct ccacttcacg atcaaagatc cagctaacag gcgctacgag gtgcccttgg    660
agaccccgcg tgtccacagc cgggcaccgt ccccactcta cagcgtggag ttctctgagg    720
agcccttcgg ggtgatcgtg caccggcagc tggacggccg cgtgctgctg aacacgacgg    780
tggcgcccct gttctttgcg gaccagttcc ttcagctgtc cacctcgctg ccctcgcagt    840
atatcacagg cctcgccgag cacctcagtc ccctgatgct cagcaccagc tggaccagga    900
tcaccctgtg gaaccgggac cttgcgccca cgcccggtgc gaacctctac gggtctcacc    960
ctttctacct ggcgctggag gacggcgggt cggcacacgg ggtgttcctg ctaaacagca   1020
atgccatgga tgtggtcctg cagccgagcc ctgcccttag ctggaggtcg acaggtggga   1080
tcctggatgt ctacatcttc ctgggcccag agcccaagag cgtggtgcag cagtacctgg   1140
acgttgtggg atacccgttc atgccgccat actggggcct gggcttccac ctgtgccgct   1200
ggggctactc ctccaccgct atcacccgcc aggtggtgga gaacatgacc agggcccact   1260
tcccccctgga cgtccaatgg aacgacctgg actacatgga ctcccggagg gacttcacgt   1320
tcaacaagga tggcttccgg gacttcccgg ccatggtgca ggagctgcac cagggcggcc   1380
ggcgctacat gatgatcgtg gatcctgcca tcagcagctc gggccctgcc gggagctaca   1440
ggccctacga cgagggtctg cggagggggg ttttcatcac caacgagacc ggccagccgc   1500
tgattgggaa ggtatggccc gggtccactg ccttccccga cttcaccaac cccacagccc   1560
tggcctggtg ggaggacatg gtggctgagt tccatgacca ggtgcccttc gacggcatgt   1620
ggattgacat gaacgagcct tccaacttca tcaggggctc tgaggacggc tgccccaaca   1680
atgagctgga gaacccaccc tacgtgcctg ggggtggttgg ggggaccctc caggcggcaa   1740
ccatctgtgc ctccagccac cagtttctct ccacacacta caacctgcac aacctctacg   1800
gcctgaccga agccatcgcc tcccacaggg cgctggtgaa ggctcggggg acacgcccat   1860
ttgtgatctc ccgctcgacc tttgctggcc acggccgata cgccggccac tggacggggg   1920
acgtgtggag ctcctgggag cagctcgcct cctccgtgcc agaaatcctg cagtttaacc   1980
tgctgggggt gcctctggtc ggggccgacg tctgcggctt cctgggcaac acctcagagg   2040
agctgtgtgt gcgctggacc cagctggggg ccttctaccc cttcatgcgg aaccacaaca   2100
gcctgctcag tctgccccag gagccgtaca gcttcagcga gccggcccag caggccatga   2160
ggaaggccct caccctgcgc tacgcactcc tcccccacct ctacacgctg ttccaccagg   2220
cccacgtcgc gggggagacc gtggcccggc ccctcttcct ggagttcccc aaggactcta   2280
gcacctggac tgtggaccac cagctcctgt ggggggaggc cctgctcatc accccagtgc   2340
tccaggccgg gaaggccgaa gtgactggct acttcccctt gggcacatgg tacgacctgc   2400
agacggtgcc aatagaggcc cttggcagcc tcccaccccc acctgcagct ccccgtgagc   2460
cagccatcca cagcgagggg cagtgggtga cgctgccggc ccccctggac accatcaacg   2520
```

tccacctccg ggctgggtac atcatccccc tgcagggccc tggcctcaca accacagagt 2580
cccgccagca gcccatggcc ctggctgtgg ccctgaccaa gggtggagag gcccgagggg 2640
agctgttctg ggacgatgga gagagcctgg aagtgctgga gcgaggggcc tacacacagg 2700
tcatcttcct ggccaggaat aacacgatcg tgaatgagct ggtacgtgtg accagtgagg 2760
gagctggcct gcagctgcag aaggtgactg tcctgggcgt ggccacggcg ccccagcagg 2820
tcctctccaa cggtgtccct gtctccaact tcacctacag ccccgacacc aaggtcctgg 2880
acatctgtgt ctcgctgttg atgggagagc agtttctcgt cagctggtgt tagtctagag 2940
cttgctagcg gccgc 2955

<210> SEQ ID NO 24
<211> LENGTH: 2958
<212> TYPE: DNA
<213> ORGANISM: Artificial Sequence
<220> FEATURE:
<223> OTHER INFORMATION: GILTd2-7d36-39-GAA70-952 cassette

<400> SEQUENCE: 24
ggtaccagct gctagcaagc taattcacac caatgggaat cccaatgggg aagtcgatgc 60
tggtgcttct caccttcttg gccttcgcct cgtgctgcat tgctgctctg tgcggcgggg 120
agctggtgga caccctccag ttcgtctgtg gggaccgcgg cttctacttc agcaggcccg 180
caagccgtgt gcgtggcatc gttgaggagt gctgtttccg cagctgtgac ctggccctcc 240
tggagacgta ctgtgctacc cccgccaagt ccgagggcgc gccggcacac cccggccgtc 300
ccagagcagt gcccacacag tgcgacgtcc cccccaacag ccgcttcgat tgcgcccctg 360
acaaggccat cacccaggaa cagtgcgagg cccgcggctg ctgctacatc cctgcaaagc 420
aggggctgca gggagcccag atggggcagc cctggtgctt cttcccaccc agctacccca 480
gctacaagct ggagaacctg agctcctctg aaatgggcta cacggccacc ctgacccgta 540
ccacccccac cttcttcccc aaggacatcc tgaccctgcg gctggacgtg atgatggaga 600
ctgagaaccg cctccacttc acgatcaaag atccagctaa caggcgctac gaggtgccct 660
tggagacccc gcgtgtccac agccgggcac cgtccccact ctacagcgtg gagttctctg 720
aggagccctt cggggtgatc gtgcaccggc agctggacgg ccgcgtgctg ctgaacacga 780
cggtggcgcc cctgttcttt gcggaccagt tccttcagct gtccacctcg ctgccctcgc 840
agtatatcac aggcctcgcc gagcacctca gtcccctgat gctcagcacc agctggacca 900
ggatcaccct gtggaaccgg gaccttgcgc ccacgcccgg tgcgaacctc tacgggtctc 960
accctttcta cctggcgctg gaggacggcg ggtcggcaca cggggtgttc ctgctaaaca 1020
gcaatgccat ggatgtggtc ctgcagccga gccctgccct tagctggagg tcgacaggtg 1080
ggatcctgga tgtctacatc ttcctgggcc cagagcccaa gagcgtggtg cagcagtacc 1140
tggacgttgt gggataccog ttcatgccgc catactgggg cctgggcttc cacctgtgcc 1200
gctggggcta ctcctccacc gctatcaccc gccaggtggt ggagaacatg accagggccc 1260
acttccccct ggacgtccaa tggaacgacc tggactacat ggactcccgg agggacttca 1320
cgttcaacaa ggatggcttc cgggacttcc cggccatggt gcaggagctg caccagggcg 1380
gccggcgcta catgatgatc gtggatcctg ccatcagcag ctcgggccct gccgggagct 1440
acaggcccta cgacgagggt ctgcggaggg gggttttcat caccaacgag accggccagc 1500
cgctgattgg gaaggtatgg cccgggtcca ctgccttccc cgacttcacc aaccccacag 1560
ccctggcctg gtgggaggac atggtggctg agttccatga ccaggtgccc ttcgacggca 1620
tgtggattga catgaacgag ccttccaact tcatcagggg ctctgaggac ggctgcccca 1680
acaatgagct ggagaaccca ccctacgtgc ctggggtggt tggggggacc ctccaggcgg 1740
caaccatctg tgcctccagc caccagtttc tctccacaca ctacaacctg cacaacctct 1800
acggcctgac cgaagccatc gcctcccaca gggcgctggt gaaggctcgg gggacacgcc 1860
catttgtgat ctcccgctcg acctttgctg gccacggccg atacgccggc cactggacgg 1920
gggacgtgtg gagctcctgg gagcagctcg cctcctccgt gccagaaatc ctgcagttta 1980
acctgctggg ggtgcctctg gtcggggccg acgtctgcgg cttcctgggc aacacctcag 2040
aggagctgtg tgtgcgctgg acccagctgg gggccttcta ccccttcatg cggaaccaca 2100
acagcctgct cagtctgccc caggagccgt acagcttcag cgagccggcc cagcaggcca 2160
tgaggaaggc cctcaccctg cgctacgcac tcctccccca cctctacacg ctgttccacc 2220
aggcccacgt cgcgggggag accgtggccc ggcccctctt cctggagttc cccaaggact 2280
ctagcacctg gactgtggac caccagctcc tgtgggggga ggccctgctc atcaccccag 2340
tgctccaggc cgggaaggcc gaagtgactg gctacttccc cttgggcaca tggtacgacc 2400
tgcagacggt gccaatagag gcccttggca gcctcccacc cccacctgca gctccccgtg 2460
agccagccat ccacagcgag gggcagtggg tgacgctgcc ggccccccctg gacaccatca 2520 acgtccacct ccgggctggg tacatcatcc ccctgcaggg ccctggcctc acaaccacag 2580
agtcccgcca gcagcccatg gccctggctg tggccctgac caagggtgga gaggcccgag 2640
gggagctgtt ctgggacgat ggagagagcc tggaagtgct ggagcgaggg gcctacacac 2700
aggtcatctt cctggccagg aataacacga tcgtgaatga gctggtacgt gtgaccagtg 2760
agggagctgg cctgcagctg cagaaggtga ctgtcctggg cgtggccacg gcgccccagc 2820
aggtcctctc caacggtgtc cctgtctcca acttcaccta cagccccgac accaaggtcc 2880
tggacatctg tgtctcgctg ttgatgggag agcagtttct cgtcagctgg tgttagtcta 2940
gagcttgcta gcggccgc 2958

<210> SEQ ID NO 25
<211> LENGTH: 2934
<212> TYPE: DNA
<213> ORGANISM: Artificial Sequence
<220> FEATURE:
<223> OTHER INFORMATION: GILTd2-7d29-40-GAA70-952 cassette

<400> SEQUENCE: 25
ggtaccagct gctagcaagc taattcacac caatgggaat cccaatgggg aagtcgatgc 60
tggtgcttct caccttcttg gccttcgcct cgtgctgcat tgctgctctg tgcggcgggg 120
agctggtgga caccctccag ttcgtctgtg gggaccgcgg cttctacttc ggcatcgttg 180
aggagtgctg tttccgcagc tgtgacctgg ccctcctgga gacgtactgt gctacccccg 240
ccaagtccga gggcgcgccg gcacaccccg gccgtcccag agcagtgccc acacagtgcg 300
acgtcccccc caacagccgc ttcgattgcg cccctgacaa ggccatcacc caggaacagt 360
gcgaggcccg cggctgctgc tacatccctg caaagcaggg gctgcaggga gcccagatgg 420
ggcagccctg gtgcttcttc ccacccagct accccagcta caagctggag aacctgagct 480
cctctgaaat gggctacacg gccaccctga cccgtaccac ccccaccttc ttccccaagg 540
acatcctgac cctgcggctg gacgtgatga tggagactga gaaccgcctc cacttcacga 600
tcaaagatcc agctaacagg cgctacgagg tgcccttgga gaccccgcgt gtccacagcc 660
gggcaccgtc cccactctac agcgtggagt tctctgagga gcccttcggg gtgatcgtgc 720
accggcagct ggacggccgc gtgctgctga acacgacggt ggcgcccctg ttctttgcgg 780
accagttcct tcagctgtcc acctcgctgc cctcgcagta tatcacaggc ctcgccgagc 840
acctcagtcc cctgatgctc agcaccagct ggaccaggat caccctgtgg aaccgggacc 900
ttgcgcccac gcccggtgcg aacctctacg ggtctcaccc tttctacctg gcgctggagg 960
acggcgggtc ggcacacggg gtgttcctgc taaacagcaa tgccatggat gtggtcctgc 1020
agccgagccc tgcccttagc tggaggtcga caggtgggat cctggatgtc tacatcttcc 1080
tgggcccaga gcccaagagc gtggtgcagc agtacctgga cgttgtggga tacccgttca 1140
tgccgccata ctggggcctg ggcttccacc tgtgccgctg ggctactcc tccaccgcta 1200 tcacccgcca ggtggtggag aacatgacca gggcccactt ccccctggac gtccaatgga 1260
acgacctgga ctacatggac tcccggaggg acttcacgtt caacaaggat ggcttccggg 1320
acttcccggc catggtgcag gagctgcacc agggcggccg gcgctacatg atgatcgtgg 1380
atcctgccat cagcagctcg ggccctgccg ggagctacag gccctacgac gagggtctgc 1440
ggaggggggt tttcatcacc aacgagaccg gccagccgct gattgggaag gtatggcccg 1500
ggtccactgc cttccccgac ttcaccaacc ccacagccct ggcctggtgg gaggacatgg 1560
tggctgagtt ccatgaccag gtgcccttcg acggcatgtg gattgacatg aacgagcctt 1620
ccaacttcat caggggctct gaggacggct gccccaacaa tgagctggag aacccaccct 1680
acgtgcctgg ggtggttggg gggaccctcc aggcggcaac catctgtgcc tccagccacc 1740
agtttctctc cacacactac aacctgcaca acctctacgg cctgaccgaa gccatcgcct 1800
cccacagggc gctggtgaag gctcggggga cacgcccatt tgtgatctcc cgctcgacct 1860
ttgctggcca cggccgatac gccggccact ggacggggga cgtgtggagc tcctgggagc 1920
agctcgcctc ctccgtgcca gaaatcctgc agtttaacct gctgggggtg cctctggtcg 1980
gggccgacgt ctgcggcttc ctgggcaaca cctcagagga gctgtgtgtg cgctggaccc 2040
agctgggggc cttctacccc ttcatgcgga accacaacag cctgctcagt ctgccccagg 2100
agccgtacag cttcagcgag ccggcccagc aggccatgag gaaggccctc accctgcgct 2160
acgcactcct cccccacctc tacacgctgt tccaccaggc ccacgtcgcg ggggagaccg 2220
tggcccggcc cctcttcctg gagttcccca aggactctag cacctggact gtggaccacc 2280
agctcctgtg gggggaggcc ctgctcatca ccccagtgct ccaggccggg aaggccgaag 2340
tgactggcta cttccccttg ggcacatggt acgacctgca gacggtgcca atagaggccc 2400
ttggcagcct cccaccccca cctgcagctc cccgtgagcc agccatccac agcgaggggc 2460
agtgggtgac gctgccggcc cccctggaca ccatcaacgt ccacctccgg gctgggtaca 2520 tcatcccct gcagggccct ggcctcacaa ccacagagtc ccgccagcag cccatggccc 2580
tggctgtggc cctgaccaag ggtggagagg cccgagggga gctgttctgg gacgatggag 2640
agagcctgga agtgctggag cgaggggcct acacacaggt catcttcctg gccaggaata 2700
acacgatcgt gaatgagctg gtacgtgtga ccagtgaggg agctggcctg cagctgcaga 2760
aggtgactgt cctgggcgtg gccacggcgc cccagcaggt cctctccaac ggtgtccctg 2820
tctccaactt cacctacagc cccgacacca aggtcctgga catctgtgtc tcgctgttga 2880
tgggagagca gtttctcgtc agctggtgtt agtctagagc ttgctagcgg ccgc 2934

<210> SEQ ID NO 26
<211> LENGTH: 2937
<212> TYPE: DNA
<213> ORGANISM: Artificial Sequence
<220> FEATURE:
<223> OTHER INFORMATION: GILTd2-7d30-40-GAA70-952 cassette

<400> SEQUENCE: 26

```
ggtaccagct gctagcaagc taattcacac caatgggaat cccaatgggg aagtcgatgc     60

tggtgcttct caccttcttg gccttcgcct cgtgctgcat tgctgctctg tgcggcgggg    120

agctggtgga caccctccag ttcgtctgtg gggaccgcgg cttctacttc agcggcatcg    180

ttgaggagtg ctgtttccgc agctgtgacc tggccctcct ggagacgtac tgtgctaccc    240

ccgccaagtc cgagggcgcg ccggcacacc ccggccgtcc cagagcagtg cccacacagt    300

gcgacgtccc ccccaacagc cgcttcgatt gcgcccctga caaggccatc acccaggaac    360

agtgcgaggc ccgcggctgc tgctacatcc ctgcaaagca ggggctgcag ggagcccaga    420

tggggcagcc ctggtgcttc ttcccaccca gctaccccag ctacaagctg gagaacctga    480

gctcctctga aatgggctac acggccaccc tgacccgtac cacccccacc ttcttcccca    540

aggacatcct gaccctgcgg ctggacgtga tgatggagac tgagaaccgc ctccacttca    600

cgatcaaaga tccagctaac aggcgctacg aggtgccctt ggagaccccg cgtgtccaca    660

gccgggcacc gtccccactc tacagcgtgg agttctctga ggagcccttc ggggtgatcg    720

tgcaccggca gctggacggc cgcgtgctgc tgaacacgac ggtggcgccc ctgttctttg    780

cggaccagtt ccttcagctg tccacctcgc tgccctcgca gtatatcaca ggcctcgccg    840

agcacctcag tcccctgatg ctcagcacca gctggaccag gatcaccctg tggaaccggg    900

accttgcgcc cacgcccggt gcgaacctct acgggtctca ccctttctac ctggcgctgg    960

aggacggcgg gtcggcacac ggggtgttcc tgctaaacag caatgccatg gatgtggtcc   1020

tgcagccgag ccctgccctt agctggaggt cgacaggtgg gatcctggat gtctacatct   1080

tcctgggccc agagcccaag agcgtggtgc agcagtacct ggacgttgtg ggatacccgt   1140

tcatgccgcc atactggggc ctgggcttcc acctgtgccg ctggggctac tcctccaccg   1200

ctatcacccg ccaggtggtg gagaacatga ccagggccca cttccccctg gacgtccaat   1260

ggaacgacct ggactacatg gactcccgga gggacttcac gttcaacaag gatggcttcc   1320

gggacttccc ggccatggtg caggagctgc accagggcgg ccggcgctac atgatgatcg   1380

tggatcctgc catcagcagc tcgggccctg ccgggagcta caggccctac gacgagggtc   1440

tgcggagggg ggttttcatc accaacgaga ccggccagcc gctgattggg aaggtatggc   1500

ccgggtccac tgccttcccc gacttcacca accccacagc cctggcctgg tgggaggaca   1560

tggtggctga gttccatgac caggtgccct tcgacggcat gtggattgac atgaacgagc   1620

cttccaactt catcaggggc tctgaggacg gctgccccaa caatgagctg gagaacccac   1680

cctacgtgcc tggggtggtt ggggggaccc tccaggcggc aaccatctgt gcctccagcc   1740

accagtttct ctccacacac tacaacctgc acaacctcta cggcctgacc gaagccatcg   1800

cctcccacag ggcgctggtg aaggctcggg ggacacgccc atttgtgatc tcccgctcga   1860

cctttgctgg ccacggccga tacgccggcc actggacggg ggacgtgtgg agctcctggg   1920

agcagctcgc ctcctccgtg ccagaaatcc tgcagtttaa cctgctgggg gtgcctctgg   1980

tcggggccga cgtctgcggc ttcctgggca acacctcaga ggagctgtgt gtgcgctgga   2040

cccagctggg ggccttctac cccttcatgc ggaaccacaa cagcctgctc agtctgcccc   2100

aggagccgta cagcttcagc gagccggccc agcaggccat gaggaaggcc ctcaccctgc   2160

gctacgcact cctcccccac ctctacacgc tgttccacca ggcccacgtc gcgggggaga   2220

ccgtggcccg gcccctcttc ctggagttcc ccaaggactc tagcacctgg actgtggacc   2280
```

accagctcct gtggggggag gccctgctca tcaccccagt gctccaggcc gggaaggccg 2340
aagtgactgg ctacttcccc ttgggcacat ggtacgacct gcagacggtg ccaatagagg 2400
cccttggcag cctcccaccc ccacctgcag ctccccgtga gccagccatc cacagcgagg 2460
ggcagtgggt gacgctgccg gccccctgg acaccatcaa cgtccacctc cgggctgggt 2520
acatcatccc cctgcagggc cctggcctca caaccacaga gtcccgccag cagcccatgg 2580
ccctggctgt ggccctgacc aagggtggag aggcccgagg ggagctgttc tgggacgatg 2640
gagagagcct ggaagtgctg gagcgagggg cctacacaca ggtcatcttc ctggccagga 2700
ataacacgat cgtgaatgag ctggtacgtg tgaccagtga gggagctggc ctgcagctgc 2760
agaaggtgac tgtcctgggc gtggccacgg cgccccagca ggtcctctcc aacggtgtcc 2820
ctgtctccaa cttcacctac agccccgaca ccaaggtcct ggacatctgt gtctcgctgt 2880
tgatgggaga gcagtttctc gtcagctggt gttagtctag agcttgctag cggccgc 2937

<210> SEQ ID NO 27
<211> LENGTH: 2940
<212> TYPE: DNA
<213> ORGANISM: Artificial Sequence
<220> FEATURE:
<223> OTHER INFORMATION: GILTd2-7d31-40-GAA70-952 cassette

<400> SEQUENCE: 27
ggtaccagct gctagcaagc taattcacac caatgggaat cccaatgggg aagtcgatgc 60
tggtgcttct caccttcttg gccttcgcct cgtgctgcat tgctgctctg tgcggcgggg 120
agctggtgga caccctccag ttcgtctgtg gggaccgcgg cttctacttc agcaggggca 180
tcgttgagga gtgctgtttc cgcagctgtg acctggccct cctggagacg tactgtgcta 240
cccccgccaa gtccgagggc gcgccggcac accccggccg tcccagagca gtgcccacac 300
agtgcgacgt cccccccaac agccgcttcg attgcgcccc tgacaaggcc atcacccagg 360
aacagtgcga ggcccgcggc tgctgctaca tccctgcaaa gcaggggctg cagggagccc 420
agatggggca gccctggtgc ttcttcccac ccagctaccc cagctacaag ctggagaacc 480
tgagctcctc tgaaatgggc tacacggcca ccctgacccg taccaccccc accttcttcc 540
ccaaggacat cctgaccctg cggctggacg tgatgatgga gactgagaac cgcctccact 600
tcacgatcaa agatccagct aacaggcgct acgaggtgcc cttggagacc ccgcgtgtcc 660
acagccgggc accgtcccca ctctacagcg tggagttctc tgaggagccc ttcggggtga 720
tcgtgcaccg gcagctggac ggccgcgtgc tgctgaacac gacggtggcg cccctgttct 780
ttgcggacca gttccttcag ctgtccacct cgctgccctc gcagtatatc acaggcctcg 840
ccgagcacct cagtcccctg atgctcagca ccagctggac caggatcacc ctgtggaacc 900
gggaccttgc gcccacgccc ggtgcgaacc tctacgggtc tcaccctttc tacctggcgc 960
tggaggacgg cgggtcggca cacggggtgt tcctgctaaa cagcaatgcc atggatgtgg 1020
tcctgcagcc gagccctgcc cttagctgga ggtcgacagg tgggatcctg gatgtctaca 1080
tcttcctggg cccagagccc aagagcgtgg tgcagcagta cctggacgtt gtgggatacc 1140
cgttcatgcc gccatactgg ggcctgggct tccacctgtg ccgctggggc tactcctcca 1200
ccgctatcac ccgccaggtg gtggagaaca tgaccagggc ccacttcccc ctggacgtcc 1260
aatggaacga cctggactac atggactccc ggagggactt cacgttcaac aaggatggct 1320
tccgggactt cccggccatg gtgcaggagc tgcaccaggg cggccggcgc tacatgatga 1380
tcgtggatcc tgccatcagc agctcgggcc ctgccgggag ctacaggccc tacgacgagg 1440
gtctgcggag gggggttttc atcaccaacg agaccggcca gccgctgatt gggaaggtat 1500
ggcccgggtc cactgccttc cccgacttca ccaaccccac agccctggcc tggtgggagg 1560
acatggtggc tgagttccat gaccaggtgc ccttcgacgg catgtggatt gacatgaacg 1620
agccttccaa cttcatcagg ggctctgagg acggctgccc caacaatgag ctggagaacc 1680
caccctacgt gcctggggtg gttgggggga ccctccaggc ggcaaccatc tgtgcctcca 1740
gccaccagtt tctctccaca cactacaacc tgcacaacct ctacggcctg accgaagcca 1800
tcgcctccca cagggcgctg gtgaaggctc gggggacacg cccatttgtg atctcccgct 1860
cgacctttgc tggccacggc cgatacgccg gccactggac gggggacgtg tggagctcct 1920
gggagcagct cgcctcctcc gtgccagaaa tcctgcagtt taacctgctg gggtgcctc 1980 tggtcggggc cgacgtctgc ggcttcctgg gcaacacctc agaggagctg tgtgtgcgct 2040
ggacccagct gggggccttc taccccttca tgcggaacca caacagcctg ctcagtctgc 2100
cccaggagcc gtacagcttc agcgagccgg cccagcaggc catgaggaag gccctcaccc 2160
tgcgctacgc actcctcccc cacctctaca cgctgttcca ccaggcccac gtcgcggggg 2220
agaccgtggc ccggcccctc ttcctggagt tccccaagga ctctagcacc tggactgtgg 2280
accaccagct cctgtggggg gaggccctgc tcatcacccc agtgctccag gccgggaagg 2340
ccgaagtgac tggctacttc cccttgggca catggtacga cctgcagacg gtgccaatag 2400
aggcccttgg cagcctccca cccccacctg cagctccccg tgagccagcc atccacagcg 2460
aggggcagtg ggtgacgctg ccggcccccc tggacaccat caacgtccac ctccgggctg 2520
ggtacatcat ccccctgcag ggccctggcc tcacaaccac agagtcccgc cagcagccca 2580
tggccctggc tgtggccctg accaagggtg gagaggcccg aggggagctg ttctgggacg 2640
atggagagag cctggaagtg ctggagcgag ggcctacac acaggtcatc ttcctggcca 2700
ggaataacac gatcgtgaat gagctggtac gtgtgaccag tgagggagct ggcctgcagc 2760
tgcagaaggt gactgtcctg ggcgtggcca cggcgcccca gcaggtcctc tccaacggtg 2820
tccctgtctc caacttcacc tacagccccg acaccaaggt cctggacatc tgtgtctcgc 2880
tgttgatggg agagcagttt ctcgtcagct ggtgttagtc tagagcttgc tagcggccgc 2940

<210> SEQ ID NO 28
<211> LENGTH: 2943
<212> TYPE: DNA
<213> ORGANISM: Artificial Sequence
<220> FEATURE:
<223> OTHER INFORMATION: GILTd2-7d32-40-GAA70-952 cassette

<400> SEQUENCE: 28
ggtaccagct gctagcaagc taattcacac caatgggaat cccaatgggg aagtcgatgc 60
tggtgcttct caccttcttg gccttcgcct cgtgctgcat tgctgctctg tgcggcgggg 120
agctggtgga caccctccag ttcgtctgtg gggaccgcgg cttctacttc agcaggcccg 180
gcatcgttga ggagtgctgt ttccgcagct gtgacctggc cctcctggag acgtactgtg 240
ctacccccgc caagtccgag ggcgcgccgg cacaccccgg ccgtcccaga gcagtgccca 300
cacagtgcga cgtccccccc aacagccgct tcgattgcgc ccctgacaag gccatcaccc 360
aggaacagtg cgaggcccgc ggctgctgct acatccctgc aaagcagggg ctgcagggag 420
cccagatggg gcagccctgg tgcttcttcc cacccagcta ccccagctac aagctggaga 480
acctgagctc ctctgaaatg ggctacacgg ccaccctgac ccgtaccacc cccaccttct 540
tccccaagga catcctgacc ctgcggctgg acgtgatgat ggagactgag aaccgcctcc 600

-continued

```
acttcacgat caaagatcca gctaacaggc gctacgaggt gcccttggag accccgcgtg    660
tccacagccg ggcaccgtcc ccactctaca gcgtggagtt ctctgaggag cccttcgggg    720
tgatcgtgca ccggcagctg gacggccgcg tgctgctgaa cacgacggtg gcgcccctgt    780
tctttgcgga ccagttcctt cagctgtcca cctcgctgcc ctcgcagtat atcacaggcc    840
tcgccgagca cctcagtccc ctgatgctca gcaccagctg gaccaggatc accctgtgga    900
accgggacct tgcgcccacg cccggtgcga acctctacgg gtctcaccct ttctacctgg    960
cgctggagga cggcgggtcg gcacacgggg tgttcctgct aaacagcaat gccatggatg   1020
tggtcctgca gccgagccct gcccttagct ggaggtcgac aggtgggatc ctggatgtct   1080
acatcttcct gggcccagag cccaagagcg tggtgcagca gtacctggac gttgtgggat   1140
acccgttcat gccgccatac tggggcctgg gcttccacct gtgccgctgg ggctactcct   1200
ccaccgctat cacccgccag gtggtggaga acatgaccag ggcccacttc cccctggacg   1260
tccaatggaa cgacctggac tacatggact cccggaggga cttcacgttc aacaaggatg   1320
gcttccggga cttcccggcc atggtgcagg agctgcacca gggcggccgg cgctacatga   1380
tgatcgtgga tcctgccatc agcagctcgg gccctgccgg gagctacagg ccctacgacg   1440
agggtctgcg gagggggggtt ttcatcacca acgagaccgg ccagccgctg attgggaagg   1500
tatggcccgg gtccactgcc ttccccgact tcaccaaccc cacagccctg gcctggtggg   1560
aggacatggt ggctgagttc catgaccagg tgcccttcga cggcatgtgg attgacatga   1620
acgagccttc caacttcatc aggggctctg aggacggctg ccccaacaat gagctggaga   1680
acccaccccta cgtgcctggg gtggttgggg ggaccctcca ggcggcaacc atctgtgcct   1740
ccagccacca gtttctctcc acacactaca acctgcacaa cctctacggc ctgaccgaag   1800
ccatcgcctc ccacagggcg ctggtgaagg ctcgggggac acgcccattt gtgatctccc   1860
gctcgacctt tgctggccac ggccgatacg ccggccactg gacgggggac gtgtggagct   1920
cctgggagca gctcgcctcc tccgtgccag aaatcctgca gtttaacctg ctgggggtgc   1980
ctctggtcgg ggccgacgtc tgcggcttcc tgggcaacac ctcagaggag ctgtgtgtgc   2040
gctggaccca gctgggggcc ttctacccct tcatgcggaa ccacaacagc ctgctcagtc   2100
tgccccagga gccgtacagc ttcagcgagc cggcccagca ggccatgagg aaggccctca   2160
ccctgcgcta cgcactcctc ccccacctct acacgctgtt ccaccaggcc cacgtcgcgg   2220
gggagaccgt ggcccggccc ctcttcctgg agttccccaa ggactctagc acctggactg   2280
tggaccacca gctcctgtgg ggggaggccc tgctcatcac cccagtgctc caggccggga   2340
aggccgaagt gactggctac ttccccttgg gcacatggta cgacctgcag acggtgccaa   2400
tagaggccct tggcagcctc ccacccccac ctgcagctcc ccgtgagcca gccatccaca   2460
gcgaggggca gtgggtgacg ctgccggccc ccctggacac catcaacgtc cacctccggg   2520
ctgggtacat catccccctg cagggccctg gcctcacaac cacagagtcc cgccagcagc   2580
ccatggccct ggctgtggcc ctgaccaagg gtggagaggc ccgaggggag ctgttctggg   2640
acgatggaga gagcctggaa gtgctggagc gaggggccta cacacaggtc atcttcctgg   2700
ccaggaataa cacgatcgtg aatgagctgg tacgtgtgac cagtgaggga gctggcctgc   2760
agctgcagaa ggtgactgtc ctgggcgtgg ccacggcgcc ccagcaggtc ctctccaacg   2820
gtgtccctgt ctccaacttc acctacagcc ccgacaccaa ggtcctggac atctgtgtct   2880
cgctgttgat gggagagcag tttctcgtca gctggtgtta gtctagagct tgctagcggc   2940
cgc                                                                 2943
```

<210> SEQ ID NO 29
<211> LENGTH: 2946
<212> TYPE: DNA
<213> ORGANISM: Artificial Sequence
<220> FEATURE:
<223> OTHER INFORMATION: GILTd2-7d33-40-GAA70-952 cassette

<400> SEQUENCE: 29
ggtaccagct gctagcaagc taattcacac caatgggaat cccaatgggg aagtcgatgc 60
tggtgcttct caccttcttg gccttcgcct cgtgctgcat tgctgctctg tgcggcgggg 120
agctggtgga caccctccag ttcgtctgtg gggaccgcgg cttctacttc agcaggcccg 180
caggcatcgt tgaggagtgc tgtttccgca gctgtgacct ggccctcctg gagacgtact 240
gtgctacccc cgccaagtcc gagggcgcgc cggcacaccc cggccgtccc agagcagtgc 300
ccacacagtg cgacgtcccc cccaacagcc gcttcgattg cgcccctgac aaggccatca 360
cccaggaaca gtgcgaggcc cgcggctgct gctacatccc tgcaaagcag gggctgcagg 420
gagcccagat ggggcagccc tggtgcttct tcccacccag ctaccccagc tacaagctgg 480
agaacctgag ctcctctgaa atgggctaca cggccaccct gacccgtacc acccccacct 540
tcttccccaa ggacatcctg accctgcggc tggacgtgat gatggagact gagaaccgcc 600
tccacttcac gatcaaagat ccagctaaca ggcgctacga ggtgcccttg gagaccccgc 660
gtgtccacag ccgggcaccg tccccactct acagcgtgga gttctctgag gagcccttcg 720 ggtgatcgt gcaccggcag ctggacggcc gcgtgctgct gaacacgacg gtggcgcccc 780
tgttctttgc ggaccagttc cttcagctgt ccacctcgct gccctcgcag tatatcacag 840
gcctcgccga gcacctcagt cccctgatgc tcagcaccag ctggaccagg atcaccctgt 900
ggaaccggga ccttgcgccc acgcccggtg cgaacctcta cggtctcac cctttctacc 960 tggcgctgga ggacggcggg tcggcacacg gggtgttcct gctaaacagc aatgccatgg 1020
atgtggtcct gcagccgagc cctgccctta gctggaggtc gacaggtggg atcctggatg 1080
tctacatctt cctgggccca gagcccaaga gcgtggtgca gcagtacctg gacgttgtgg 1140
gatacccgtt catgccgcca tactggggcc tgggcttcca cctgtgccgc tggggctact 1200
cctccaccgc tatcacccgc caggtggtgg agaacatgac cagggcccac ttcccctgg 1260 acgtccaatg gaacgacctg gactacatgg actcccggag ggacttcacg ttcaacaagg 1320
atggcttccg ggacttcccg gccatggtgc aggagctgca ccagggcggc cggcgctaca 1380
tgatgatcgt ggatcctgcc atcagcagct cgggccctgc cgggagctac aggccctacg 1440
acgagggtct gcggaggggg gttttcatca ccaacgagac cggccagccg ctgattggga 1500
aggtatggcc cgggtccact gccttccccg acttcaccaa ccccacagcc ctggcctggt 1560
gggaggacat ggtggctgag ttccatgacc aggtgccctt cgacggcatg tggattgaca 1620
tgaacgagcc ttccaacttc atcaggggct ctgaggacgg ctgccccaac aatgagctgg 1680
agaacccacc ctacgtgcct ggggtggttg gggggaccct ccaggcggca accatctgtg 1740
cctccagcca ccagtttctc tccacacact acaacctgca caacctctac ggcctgaccg 1800
aagccatcgc ctcccacagg gcgctggtga aggctcgggg gacacgccca tttgtgatct 1860
cccgctcgac ctttgctggc cacggccgat acgccggcca ctggacgggg gacgtgtgga 1920
gctcctggga gcagctcgcc tcctccgtgc cagaaatcct gcagtttaac ctgctggggg 1980
tgcctctggt cggggccgac gtctgcggct tcctgggcaa cacctcagag gagctgtgtg 2040
tgcgctggac ccagctgggg gccttctacc ccttcatgcg gaaccacaac agcctgctca 2100

-continued gtctgcccca ggagccgtac agcttcagcg agccggccca gcaggccatg aggaaggccc 2160
tcaccctgcg ctacgcactc ctcccccacc tctacacgct gttccaccag gcccacgtcg 2220
cgggggagac cgtggcccgg cccctcttcc tggagttccc caaggactct agcacctgga 2280
ctgtggacca ccagctcctg tggggggagg ccctgctcat caccccagtg ctccaggccg 2340
ggaaggccga agtgactggc tacttcccct tgggcacatg gtacgacctg cagacggtgc 2400
caatagaggc ccttggcagc ctcccacccc cacctgcagc tccccgtgag ccagccatcc 2460
acagcgaggg gcagtgggtg acgctgccgg ccccccctgga caccatcaac gtccacctcc 2520
gggctgggta catcatcccc ctgcagggcc ctggcctcac aaccacagag tcccgccagc 2580
agcccatggc cctggctgtg gccctgacca agggtggaga ggcccgaggg gagctgttct 2640
gggacgatgg agagagcctg gaagtgctgg agcgaggggc ctacacacag gtcatcttcc 2700
tggccaggaa taacacgatc gtgaatgagc tggtacgtgt gaccagtgag ggagctggcc 2760
tgcagctgca gaaggtgact gtcctgggcg tggccacggc gccccagcag gtcctctcca 2820
acggtgtccc tgtctccaac ttcacctaca gccccgacac caaggtcctg gacatctgtg 2880
tctcgctgtt gatgggagag cagtttctcg tcagctggtg ttagtctaga gcttgctagc 2940
ggccgc 2946

<210> SEQ ID NO 30
<211> LENGTH: 2949
<212> TYPE: DNA
<213> ORGANISM: Artificial Sequence
<220> FEATURE:
<223> OTHER INFORMATION: GILTd2-7d34-40-GAA70-952 cassette

<400> SEQUENCE: 30
ggtaccagct gctagcaagc taattcacac caatgggaat cccaatgggg aagtcgatgc 60
tggtgcttct caccttcttg gccttcgcct cgtgctgcat tgctgctctg tgcggcgggg 120
agctggtgga caccctccag ttcgtctgtg gggaccgcgg cttctacttc agcaggcccg 180
caagcggcat cgttgaggag tgctgtttcc gcagctgtga cctggccctc ctggagacgt 240
actgtgctac ccccgccaag tccgagggcg cgccggcaca ccccggccgt cccagagcag 300
tgcccacaca gtgcgacgtc ccccccaaca gccgcttcga ttgcgcccct gacaaggcca 360
tcacccagga acagtgcgag gcccgcggct gctgctacat ccctgcaaag caggggctgc 420
agggagccca gatggggcag ccctggtgct tcttcccacc cagctacccc agctacaagc 480
tggagaacct gagctcctct gaaatgggct acacggccac cctgacccgt accaccccca 540
ccttcttccc caaggacatc ctgaccctgc ggctggacgt gatgatggag actgagaacc 600
gcctccactt cacgatcaaa gatccagcta acaggcgcta cgaggtgccc ttggagaccc 660
cgcgtgtcca cagccgggca ccgtccccac tctacagcgt ggagttctct gaggagccct 720
tcggggtgat cgtgcaccgg cagctggacg gccgcgtgct gctgaacacg acggtggcgc 780
ccctgttctt tgcggaccag ttccttcagc tgtccacctc gctgccctcg cagtatatca 840
caggcctcgc cgagcacctc agtcccctga tgctcagcac cagctggacc aggatcaccc 900
tgtggaaccg ggaccttgcg cccacgcccg gtgcgaacct ctacgggtct caccctttct 960
acctggcgct ggaggacggc gggtcggcac acggggtgtt cctgctaaac agcaatgcca 1020
tggatgtggt cctgcagccg agccctgccc ttagctggag gtcgacaggt gggatcctgg 1080
atgtctacat cttcctgggc ccagagccca agagcgtggt gcagcagtac ctggacgttg 1140
tgggataccc gttcatgccg ccatactggg gcctgggctt ccacctgtgc cgctggggct 1200

```
actcctccac cgctatcacc cgccaggtgg tggagaacat gaccagggcc cacttccccc   1260

tggacgtcca atggaacgac ctggactaca tggactcccg gagggacttc acgttcaaca   1320

aggatggctt ccgggacttc ccggccatgg tgcaggagct gcaccagggc ggccggcgct   1380

acatgatgat cgtggatcct gccatcagca gctcgggccc tgccgggagc tacaggccct   1440

acgacgaggg tctgcggagg ggggttttca tcaccaacga gaccggccag ccgctgattg   1500

ggaaggtatg gcccgggtcc actgccttcc ccgacttcac caaccccaca gccctggcct   1560

ggtgggagga catggtggct gagttccatg accaggtgcc cttcgacggc atgtggattg   1620

acatgaacga gccttccaac ttcatcaggg gctctgagga cggctgcccc aacaatgagc   1680

tggagaaccc accctacgtg cctggggtgg ttgggggggac cctccaggcg gcaaccatct   1740

gtgcctccag ccaccagttt ctctccacac actacaacct gcacaacctc tacggcctga   1800

ccgaagccat cgcctcccac agggcgctgg tgaaggctcg gggacacgc ccatttgtga   1860

tctcccgctc gacctttgct ggccacggcc gatacgccgg ccactggacg gggacgtgt    1920

ggagctcctg ggagcagctc gcctcctccg tgccagaaat cctgcagttt aacctgctgg   1980

gggtgcctct ggtcggggcc gacgtctgcg gcttcctggg caacacctca gaggagctgt   2040

gtgtgcgctg gacccagctg gggccttct accccttcat gcggaaccac aacagcctgc    2100

tcagtctgcc ccaggagccg tacagcttca gcgagccggc ccagcaggcc atgaggaagg   2160

ccctcaccct gcgctacgca ctcctccccc acctctacac gctgttccac caggcccacg   2220

tcgcggggga gaccgtggcc cggcccctct tcctggagtt ccccaaggac tctagcacct   2280

ggactgtgga ccaccagctc ctgtgggggg aggccctgct catcacccca gtgctccagg   2340

ccgggaaggc cgaagtgact ggctacttcc ccttgggcac atggtacgac ctgcagacgg   2400

tgccaataga ggcccttggc agcctcccac ccccacctgc agctccccgt gagccagcca   2460

tccacagcga ggggcagtgg gtgacgctgc cggccccct ggacaccatc aacgtccacc    2520

tccgggctgg gtacatcatc cccctgcagg gccctggcct cacaaccaca gagtcccgcc   2580

agcagcccat ggccctggct gtggccctga ccaagggtgg agaggcccga ggggagctgt   2640

tctgggacga tggagagagc ctggaagtgc tggagcgagg ggcctacaca caggtcatct   2700

tcctggccag gaataacacg atcgtgaatg agctggtacg tgtgaccagt gagggagctg   2760

gcctgcagct gcagaaggtg actgtcctgg gcgtggccac ggcgccccag caggtcctct   2820

ccaacggtgt ccctgtctcc aacttcacct acagccccga caccaaggtc ctggacatct   2880

gtgtctcgct gttgatggga gagcagtttc tcgtcagctg gtgttagtct agagcttgct   2940

agcggccgc                                                           2949
```

<210> SEQ ID NO 31
<211> LENGTH: 2953
<212> TYPE: DNA
<213> ORGANISM: Artificial Sequence
<220> FEATURE:
<223> OTHER INFORMATION: GILTd2-7M1/L27A37-GAA70-952 cassette

<400> SEQUENCE: 31

```
ggtaccaagc ttgccatggg aatcccaatg ggcaagtcga tgctggtgct gctcaccttc     60

ttggcctttg cctcgtgctg cattgccgct ctgtgcggcg gggaactggt ggacaccctc    120

caattcgtct gtggggaccg gggcttcctg ttcagcagac ccgcaagccg tgtgagtgct    180

cgcagccgtg gcattgttga ggagtgctgt tttcgcagct gtgacctggc tctcctggag    240

acgtactgcg ctacccccgc caagtctgag ggcgcgccgg cacaccccgg ccgtcccaga    300
```

-continued

```
gcagtgccca cacagtgcga cgtccccccc aacagccgct tcgattgcgc ccctgacaag    360
gccatcaccc aggaacagtg cgaggcccgc ggctgctgct acatccctgc aaagcagggg    420
ctgcagggag cccagatggg gcagccctgg tgcttcttcc cacccagcta ccccagctac    480
aagctggaga acctgagctc ctctgaaatg ggctacacgg ccaccctgac ccgtaccacc    540
cccaccttct tccccaagga catcctgacc ctgcggctgg acgtgatgat ggagactgag    600
aaccgcctcc acttcacgat caaagatcca gctaacaggc gctacgaggt gcccttggag    660
accccgcgtg tccacagccg ggcaccgtcc ccactctaca gcgtggagtt ctctgaggag    720
cccttcgggg tgatcgtgca ccggcagctg gacggccgcg tgctgctgaa cacgacggtg    780
gcgcccctgt tctttgcgga ccagttcctt cagctgtcca cctcgctgcc ctcgcagtat    840
atcacaggcc tcgccgagca cctcagtccc ctgatgctca gcaccagctg gaccaggatc    900
accctgtgga accgggacct tgcgcccacg cccggtgcga acctctacgg gtctcaccct    960
ttctacctgg cgctggagga cggcgggtcg gcacacgggg tgttcctgct aaacagcaat   1020
gccatggatg tggtcctgca gccgagccct gcccttagct ggaggtcgac aggtgggatc   1080
ctggatgtct acatcttcct gggcccagag cccaagagcg tggtgcagca gtacctggac   1140
gttgtgggat acccgttcat gccgccatac tggggcctgg gcttccacct gtgccgctgg   1200
ggctactcct ccaccgctat cacccgccag gtggtggaga acatgaccag ggcccacttc   1260
cccctggacg tccaatggaa cgacctggac tacatggact cccggaggga cttcacgttc   1320
aacaaggatg gcttccggga cttcccggcc atggtgcagg agctgcacca gggcggccgg   1380
cgctacatga tgatcgtgga tcctgccatc agcagctcgg gccctgccgg gagctacagg   1440
ccctacgacg agggtctgcg gagggggggtt ttcatcacca acgagaccgg ccagccgctg   1500
attgggaagg tatggcccgg gtccactgcc ttccccgact tcaccaaccc cacagccctg   1560
gcctggtggg aggacatggt ggctgagttc catgaccagg tgcccttcga cggcatgtgg   1620
attgacatga acgagccttc caacttcatc aggggctctg aggacggctg ccccaacaat   1680
gagctggaga acccacccta cgtgcctggg gtggttgggg ggaccctcca ggcggcaacc   1740
atctgtgcct ccagccacca gtttctctcc acacactaca acctgcacaa cctctacggc   1800
ctgaccgaag ccatcgcctc ccacagggcg ctggtgaagg ctcgggggac acgcccattt   1860
gtgatctccc gctcgacctt tgctggccac ggccgatacg ccggccactg gacgggggac   1920
gtgtggagct cctgggagca gctcgcctcc tccgtgccag aaatcctgca gtttaacctg   1980
ctgggggtgc ctctggtcgg ggccgacgtc tgcggcttcc tgggcaacac ctcagaggag   2040
ctgtgtgtgc gctggaccca gctgggggcc ttctacccct tcatgcggaa ccacaacagc   2100
ctgctcagtc tgccccagga gccgtacagc ttcagcgagc cggcccagca ggccatgagg   2160
aaggccctca ccctgcgcta cgcactcctc ccccacctct acacgctgtt ccaccaggcc   2220
cacgtcgcgg gggagaccgt ggcccggccc ctcttcctgg agttccccaa ggactctagc   2280
acctggactg tggaccacca gctcctgtgg ggggaggccc tgctcatcac cccagtgctc   2340
caggccggga aggccgaagt gactggctac ttccccttgg gcacatggta cgacctgcag   2400
acggtgccaa tagaggccct tggcagcctc ccaccccccac ctgcagctcc ccgtgagcca   2460
gccatccaca gcgagggggca gtgggtgacg ctgccggccc ccctggacac catcaacgtc   2520
cacctccggg ctgggtacat catcccccctg cagggccctg gcctcacaac cacagagtcc   2580
cgccagcagc ccatggccct ggctgtggcc ctgaccaagg gtggagaggc ccgaggggag   2640
ctgttctggg acgatggaga gagcctggaa gtgctggagc gaggggccta cacacaggtc   2700
```

-continued atcttcctgg ccaggaataa cacgatcgtg aatgagctgg tacgtgtgac cagtgaggga 2760
gctggcctgc agctgcagaa ggtgactgtc ctgggcgtgg ccacggcgcc ccagcaggtc 2820
ctctccaacg gtgtccctgt ctccaacttc acctacagcc ccgacaccaa ggtcctggac 2880
atctgtgtct cgctgttgat gggagagcag tttctcgtca gctggtgtta gtctagagct 2940
tgctagcggc cgc 2953

<210> SEQ ID NO 32
<211> LENGTH: 8
<212> TYPE: PRT
<213> ORGANISM: Artificial Sequence
<220> FEATURE:
<223> OTHER INFORMATION: Furin cleavage site - ZC-701

<400> SEQUENCE: 32

Arg Val Ser Arg Arg Ser Arg Gly
1 5

<210> SEQ ID NO 33
<211> LENGTH: 8
<212> TYPE: PRT
<213> ORGANISM: Artificial Sequence
<220> FEATURE:
<223> OTHER INFORMATION: Furin cleavage site - p1459 K37

<400> SEQUENCE: 33

Arg Val Ser Lys Arg Ser Arg Gly
1 5

<210> SEQ ID NO 34
<211> LENGTH: 8
<212> TYPE: PRT
<213> ORGANISM: Artificial Sequence
<220> FEATURE:
<223> OTHER INFORMATION: Furin cleavage site - p1460 K40

<400> SEQUENCE: 34

Arg Val Ser Arg Arg Ser Lys Gly
1 5

<210> SEQ ID NO 35
<211> LENGTH: 8
<212> TYPE: PRT
<213> ORGANISM: Artificial Sequence
<220> FEATURE:
<223> OTHER INFORMATION: Furin cleavage site - p1461 A37

<400> SEQUENCE: 35

Arg Val Ser Ala Arg Ser Arg Gly
1 5